US009989448B2

(12) United States Patent
Dyson-Holland et al.

(10) Patent No.: US 9,989,448 B2
(45) Date of Patent: Jun. 5, 2018

(54) SPECIMEN PROCESSING SYSTEMS AND METHODS FOR HOLDING SLIDES

(71) Applicant: Ventana Medical Systems, Inc., Tucson, AZ (US)

(72) Inventors: Luke Dyson-Holland, Hawthorn East (AU); Daniel C. Malberg, Hawthorn East (AU); Timothy B. McDonald, Hawthorn (AU); Donald M. Barnett, Tucson, AZ (US); Kevin D. Marshall, Tucson, AZ (US); John Willems, Tucson, AZ (US); Timothy Durrant, Camberwell (AU); Simon Spence, Hawthorn (AU); Benjamin James, St. Kilda (AU); Joshua David Kenneth Harrison, Tucson, AZ (US); Matthew Ketterer, Oro Valley, AZ (US); Brian Kram, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 264 days.

(21) Appl. No.: 14/737,320

(22) Filed: Jun. 11, 2015

(65) Prior Publication Data
US 2015/0323776 A1 Nov. 12, 2015

Related U.S. Application Data

(63) Continuation of application No. PCT/US2013/077162, filed on Dec. 20, 2013, and a
(Continued)

(51) Int. Cl.
*G02B 21/36* (2006.01)
*G01N 1/31* (2006.01)
(Continued)

(52) U.S. Cl.
CPC .......... *G01N 1/312* (2013.01); *G02B 21/362* (2013.01); *B01L 9/52* (2013.01); *G02B 21/34* (2013.01)

(58) Field of Classification Search
CPC ...... G01N 1/312; G02B 21/362; G02B 21/34; B01L 9/52
(Continued)

(56) References Cited

U.S. PATENT DOCUMENTS

| 4,336,765 A | 6/1982 | Coughlin |
| 5,948,358 A | 9/1999 | Saito |

(Continued)

FOREIGN PATENT DOCUMENTS

| CN | 1726386 A | 1/2006 |
| CN | 1976868 A | 6/2007 |

(Continued)

OTHER PUBLICATIONS

International Application No. PCT/US2010/056752, Ventana Medical Systems, Inc.
(Continued)

*Primary Examiner* — Thai Tran
*Assistant Examiner* — Nien-Ru Yang
(74) *Attorney, Agent, or Firm* — Eric Grant Lee; Aden A. Rehms

(57) ABSTRACT

At least some embodiments of the technology are directed to an automated slide processing apparatus configured to apply at least one reagent to a specimen carried by a microscope slide. The slide processing station can include a support element with a support surface, at least one vacuum port, and a sealing member having a non-round shape. In an uncompressed state, the sealing member can extend upwardly beyond the support surface. In a compressed state, the sealing member can be configured to maintain an airtight
(Continued)

seal with a backside of the microscope slide as the microscope slide is pulled against the support surface by a vacuum drawn via the at least one vacuum port.

10 Claims, 52 Drawing Sheets

Related U.S. Application Data continuation of application No. PCT/US2013/077192, filed on Dec. 20, 2013, and a continuation of application No. PCT/US2013/007717, filed on Dec. 20, 2013.

(60) Provisional application No. 61/799,098, filed on Mar. 15, 2013, provisional application No. 61/746,085, filed on Dec. 26, 2012, provisional application No. 61/798,238, filed on Mar. 15, 2013, provisional application No. 61/746,091, filed on Dec. 26, 2012, provisional application No. 61/799,497, filed on Mar. 15, 2013, provisional application No. 61/746,089, filed on Dec. 26, 2012.

(51) Int. Cl.
*G02B 21/34* (2006.01)
*B01L 9/00* (2006.01)

(58) Field of Classification Search
USPC .......................................................... 348/79
See application file for complete search history.

(56) References Cited

U.S. PATENT DOCUMENTS

| | | | |
|---|---|---|---|
| 5,985,669 A | 11/1999 | Palander | |
| 6,146,591 A | 11/2000 | Miller | |
| 6,146,592 A | 11/2000 | Kawashima et al. | |
| 6,403,931 B1 | 6/2002 | Showalter et al. | |
| 6,703,247 B1 | 3/2004 | Chu | |
| 6,847,481 B1 | 1/2005 | Ludl et al. | |
| 7,338,803 B2 | 3/2008 | Mizzer et al. | |
| 7,425,306 B1 | 9/2008 | Kram | |
| 7,468,161 B2 | 12/2008 | Reinhardt et al. | |
| 8,296,809 B2 | 10/2012 | Hirota | |
| 8,459,509 B2 | 6/2013 | Bui | |
| 8,911,815 B2 | 12/2014 | Kram et al. | |
| 2003/0211630 A1 | 11/2003 | Richards et al. | |
| 2004/0023371 A1 | 2/2004 | Fawcett | |
| 2004/0114227 A1* | 6/2004 | Henderson | B01L 9/52 359/391 |
| 2005/0089949 A1 | 4/2005 | Baer et al. | |
| 2005/0186114 A1* | 8/2005 | Reinhardt | B01L 9/52 422/65 |
| 2006/0148063 A1 | 7/2006 | Fauzzi et al. | |
| 2008/0193333 A1 | 8/2008 | Takahashi et al. | |
| 2008/0214378 A1* | 9/2008 | Stokes | B01L 3/502 494/37 |
| 2010/0031757 A1 | 2/2010 | Hoyer | |
| 2011/0305842 A1 | 12/2011 | Kram | |
| 2012/0189412 A1 | 7/2012 | Hoffmann et al. | |
| 2013/0223771 A1 | 8/2013 | Tanaka | |

FOREIGN PATENT DOCUMENTS

| | | |
|---|---|---|
| CN | 102518808 A | 6/2012 |
| CN | 102713319 A | 10/2012 |
| CN | 2025608369 U | 11/2012 |
| JP | 6-207944 A | 7/1994 |
| JP | 9-21799 A | 1/1997 |
| JP | 9-243647 A | 9/1997 |
| JP | 10-62429 | 3/1998 |
| JP | 10-62431 A | 3/1998 |
| JP | 2001-021813 A | 1/2001 |
| JP | 2002-504694 A | 2/2002 |
| JP | 2002-507738 A | 3/2002 |
| JP | 2002-267942 A | 9/2002 |
| JP | 2007-225339 A | 9/2007 |
| JP | 2009-538426 A | 11/2009 |
| JP | 2011-99807 A | 5/2011 |
| JP | 2013-511048 A | 3/2013 |
| KR | 10-2006-0058682 A | 5/2006 |
| WO | 91/15826 A1 | 10/1991 |
| WO | 97/26541 A1 | 7/1997 |
| WO | 99/44030 A1 | 9/1999 |
| WO | 99/44032 A1 | 9/1999 |
| WO | 9943434 A1 | 9/1999 |
| WO | 9949295 A1 | 9/1999 |
| WO | 2010074915 A2 | 11/1999 |
| WO | 01/22086 A1 | 3/2001 |
| WO | 02/13967 A2 | 2/2002 |
| WO | 2004057307 A1 | 7/2004 |
| WO | 2005019092 A2 | 3/2005 |
| WO | 2005/053827 A1 | 6/2005 |
| WO | 2006/098442 A1 | 9/2006 |
| WO | 2007012400 A1 | 2/2007 |
| WO | 2010/074917 A1 | 7/2010 |
| WO | 2011/060387 A1 | 5/2011 |
| WO | 2011060387 A1 | 5/2011 |
| WO | 2014105739 A1 | 7/2014 |
| WO | 2014105744 A2 | 7/2014 |
| WO | 2014105747 A2 | 7/2014 |

OTHER PUBLICATIONS

International Application No. PCT/US2013/077177, International Search Report and Written Opinion, dated Jul. 4, 2014.
International Application No. PCT/US2012/077162, International Search Report and Written Opinion, dated Aug. 5, 2014.
International Application No. PCT/US2013/077649, International Search Report and Written Opinion, dated Jun. 27, 2014.
Qiu, K, et al., Development and calibration of crop pollen auto-acquisition sensor, Transactions of Atmospheric Sciences, (2011), pp. 497-503, vol. 34.

* cited by examiner

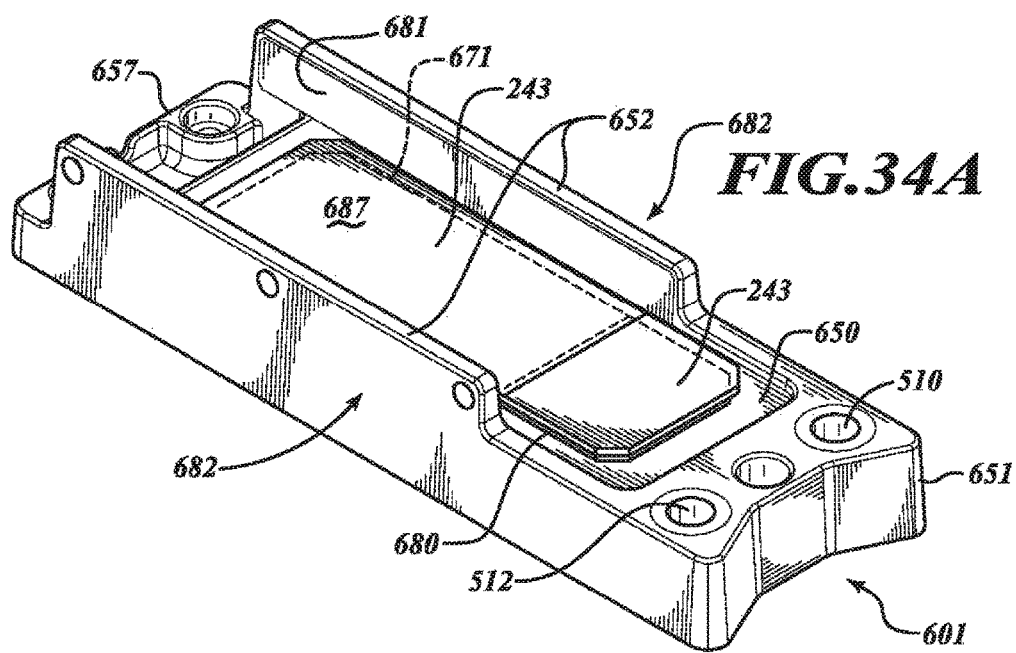
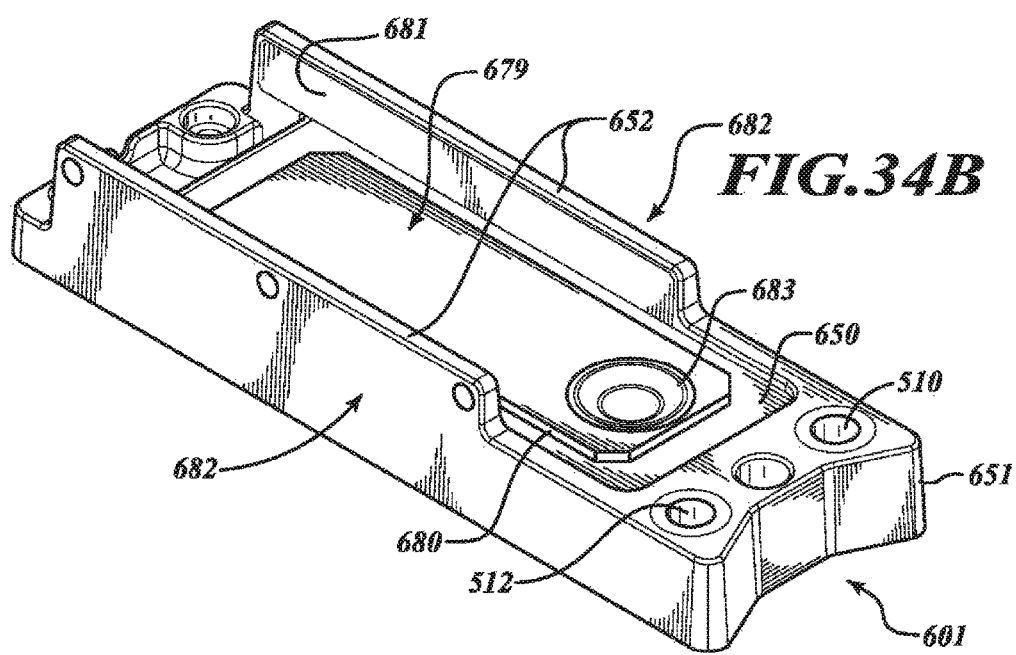

SPECIMEN PROCESSING SYSTEMS AND METHODS FOR HOLDING SLIDES

CROSS-REFERENCE TO RELATED APPLICATIONS

This application is a Continuation application of PCT/US13/77162, PCT/US13/77192, and PCT/US13/77177, each filed on Dec. 20, 2014 and which claim benefit of and priority to U.S. Provisional Patent Application Nos. 61/746,089, 61/746,085, and 61/746,091 filed Dec. 26, 2012, and U.S. Provisional Patent Application Nos. 61/799,497, 61/799,098 and 61/798,238 filed Mar. 15, 2013, respectively, and which are all herein incorporated by reference in their entireties.

TECHNICAL FIELD

This disclosure relates to systems for preparing specimens for analysis. In particular, the disclosure relates to specimen processing systems and methods of processing specimens.

BACKGROUND

A wide variety of techniques have been developed to prepare and analyze biological specimens. Example techniques include microscopy, microarray analyses (e.g., protein and nucleic acid microarray analyses), and mass spectrometric methods. Specimens are prepared for analysis by applying one or more liquids to the specimens. If a specimen is treated with multiple liquids, both the application and the subsequent removal of each of the liquids can be important for producing samples suitable for analysis.

Microscope slides bearing biological specimens, e.g., tissue sections or cells, are often treated with one or more dyes or reagents to add color and contrast to otherwise transparent or invisible cells or cell components. Specimens can be prepared for analysis by manually applying dyes or other reagents to specimen-bearing slides. This labor-intensive process often results in inconsistent processing due to individual techniques among laboratory technicians.

"Dip and dunk" automated machines immerse specimens in liquids by a technique similar to manual immersing techniques. These automated machines can process specimens in batches by submerging racks carrying microscope slides in open baths. Unfortunately, carryover of liquids between containers leads to contamination and degradation of the processing liquids. Worse, cells sloughing off the specimen carrying slides can cause contamination of other slides in the liquid baths. These types of processes also utilize excessive volumes of liquids, resulting in relatively high processing costs when the reagents must be changed to reduce the possibility of specimen cross-contamination. Open containers are also prone to evaporative losses and reagent oxidative degradation that may significantly alter the concentration and effectiveness of the reagents, resulting in inconsistent processing. It may be difficult to process samples without producing significant volumes of waste that may require special handling and disposal.

Immunohistochemical and in situ hybridization staining processes are often used to prepare tissue specimens. The rate of immunohistochemical and in situ hybridization staining of sectioned fixed tissue on a microscope slide is limited by the speed at which molecules (e.g., conjugating biomolecules) can diffuse into the fixed tissue from an aqueous solution placed in direct contact with the tissue section. Tissue is often "fixed" immediately after excision by placing it in a 10% solution of formaldehyde, which preserves the tissue from autocatalytic destruction by cross-linking much of the protein via methylene bridges. This cross-linked tissue may present many additional barriers to diffusion, including the lipid bilayer membranes that enclose individual cells and organelles. Conjugate biomolecules (antibody or DNA probe molecules) can be relatively large, ranging in size from a few kilodaltons to several hundred kilodaltons, which constrains them to diffuse slowly into solid tissue with typical times for sufficient diffusion being in the range of several minutes to a few hours. Typical incubation conditions are 30 minutes at 37 degrees centigrade. The stain rate is often driven by a concentration gradient so the stain rate can be increased by increasing the concentration of the conjugate in the reagent to compensate for slow diffusion. Unfortunately, conjugates are often very expensive, so increasing their concentration is wasteful and often not economically viable. Additionally, the excessive amount of conjugate that is driven into the tissue, when high concentrations are used, is entrapped in the tissue, is difficult to rinse out, and causes high levels of non-specific background staining. In order to reduce the noise due to non-specific background staining and increase the signal of specific staining, low concentrations of conjugate with long incubation times are often used to allow the conjugate to bind only to the specific sites.

Histology staining instruments often use relatively large volumes of reagent (100 µL) in a puddle of typically 300 µL of buffer. Some conventional instruments mix the reagent by alternating tangential air jets onto an overlaying oil layer that rotates and counter-rotates when contacted by the alternating air jets, thereby imparting motion into the underlying aqueous puddle. This mixing is slow and not particularly vigorous, and it can create significant evaporation losses, especially at the elevated temperatures that are often necessary. Large volumes of rinse liquid are used to physically displace the large puddles of reagents, which are covered with oil. This rinsing procedure produces large volumes of waste liquid, which may be hazardous waste.

OVERVIEW OF TECHNOLOGY

At least some embodiments of the technology are directed to an automated slide processing apparatus configured to apply at least one reagent to a specimen carried by a microscope slide. A slide processing station can include a support element with a support surface, at least one port, and a sealing member having a non-round shape (e.g., as viewed from above). The sealing member can be moveable between an uncompressed state and a compressed state. In the uncompressed state, the sealing member can extend upwardly beyond the support surface. In the compressed state, the sealing member can be configured to maintain a seal with a backside of the microscope slide as the microscope slide is urged against the support surface by a vacuum drawn via the at least one port. The sealing member, in some embodiments, can have a rounded-corner rectangular shape (e.g., a shape with rounded corners with radii less than the lengths of straight sides) or a rectangular shape as viewed from above. In one embodiment, the sealing member has a rounded-corner polygonal shape or a polygonal shape as viewed along an axis generally perpendicular to the support surface.

In some embodiments, at least a portion of the support element can have a non-round shape and can extend between the sealing member and the at least one vacuum port. In one embodiment, the support element includes a trench, and the sealing member includes a compliant gasket having a main body and a lip. The main body can be positioned in the trench, and the lip can extend radially outward from the main body. In some embodiments, the lip can be moveable between a compressed configuration and a uncompressed configuration. In the uncompressed configuration, the lip can extend upwardly from the trench. In the compressed configuration, the lip can extend toward a sidewall of the trench. In one embodiment, the lip is movable between the uncompressed configuration and the compressed configuration without contacting the sidewall of the trench. When the microscope slide is drawn against the support surface, the lip can be spaced apart from a sidewall of the trench but capable of physically contacting the sidewall of the trench to inhibit movement of the microscope slide relative to the support element. In one embodiment, the lip is sufficiently stiff to prevent any rotation of the slide about a vertical axis. As such, the slide is rotationally fixed relative to the support surface. In one embodiment, the lip is configured to physically contact the sidewall when the microscope slide is rotated at least about 2 degrees about a vertical axis.

The sealing member in the compressed configuration can be positioned on one side of a plane in which a backside surface of the microscope slide is located when the microscope slide is pulled against the support surface. In the uncompressed configuration, the sealing member can be located on both sides of the plane. The support element can include a vacuum surface surrounded by at least one vacuum port. The vacuum surface can be spaced apart from and positioned below the plane such that the vacuum surface and the microscope slide at least partially define a vacuum chamber with a height less than a height of the sealing member.

In some embodiments, the sealing member can include a lip configured to deflect primarily in a direction perpendicular to a backside surface of the microscope slide during use. The lip can be movable between an uncompressed configuration for contacting the slide moving toward the support surface and a compressed configuration for maintaining an airtight seal. In the uncompressed position, the lip can extend upwardly beyond the support surface. In the compressed position, the lip can be positioned at or below the support surface. In some embodiments, the lip can be configured to be deflected as the microscope slide moves toward the support surface to form the airtight seal with the slide. The sealing member, in some embodiments, can be positioned to be located under a label of the microscope slide during use.

At least some embodiments of the automated slide processing system include a vacuum source in communication with at least one vacuum inlet and configured to draw a sufficient vacuum to maintain the airtight seal. In some embodiments, the slide processing system can include a heater configured to heat the support element such that the support element conductively heats the microscope slide while the sealing member maintains the airtight seal.

Some of the embodiments of the technology are directed to methods of holding a microscope slide. In one embodiment, the method comprises positioning a microscope slide on a support element that has a first portion that surrounds a second portion and aligning a label-bearing portion of the slide with the second portion and a specimen-bearing portion of the slide with the first portion. The method can also include drawing a vacuum through the second portion and sealing the slide to a sealing member. In some embodiments, the method further includes inhibiting at least one of translational or rotational movement of the slide with respect to the support element. The method can also include creating a vacuum chamber between the second portion and a backside of the microscope slide. In some embodiments, positioning the microscope slide includes contacting a top portion of the sealing member and deflecting the top portion of the sealing member in a direction that is generally perpendicular to the path of travel of the slide.

Some embodiments of the technology are directed to an automated slide processing apparatus for dispensing liquids onto one or more microscope slides. The automated slide processing apparatus can comprise, in one embodiment, a carousel that includes a plurality of reservoir wells and a reagent pipette assembly that includes a reagent pipette movable between at least one loading position for obtaining reagent from one of the reservoir wells and at least one dispense position for dispensing reagent onto one of the microscope slides. In some arrangements, the automated slide processing apparatus can also include a wash pipette assembly configured to wash the plurality of reservoir wells and a drive mechanism coupled to the carousel and configured to rotate the carousel to position the reservoir wells relative to the reagent pipette assembly and/or the wash pipette assembly.

At least some of the embodiments of the automated slide processing apparatus can include a filling station including a plurality of containers holding reagents and a plurality of slide processing stations. The reagent pipette assembly, for example, can be movable through an internal chamber of the automated slide processing apparatus to transport reagents obtained at the filling station to the carousel and to dispense reagent mixtures from the carousel onto one of the microscope slides. In another embodiment, the reagent pipette assembly is movable between a filling position for obtaining reagent from the containers at the filling station and a dispensing position for filling one or more of the reservoir wells with reagent from the filling station. In some embodiments, the automated slide processing apparatus has a mixing mode in which the reagent pipette assembly mixes reagents within one or more of the reservoir wells and dispenses the reagent mixtures onto the microscope slides. In other embodiments, the wash pipette assembly mixes reagents within one of the reservoir wells.

The drive mechanism, for example, can be configured to sequentially rotate the reservoir wells underneath a wash pipette of the wash pipette assembly and/or the reagent pipette of het reagent pipette assembly. In one embodiment, the reagent pipette assembly has a reagent load state for obtaining reagent from the reservoir wells while the wash pipette assembly, for example, delivers wash liquid to another one of the reagent wells. In some embodiments, the wash pipette assembly includes a pipette movable into each of the reservoir wells. In a further embodiment, the wash pipette assembly is fluidically coupled to a vacuum source, and the wash pipette assembly draws liquid from one of the reservoir wells when the vacuum source draws a vacuum. In some embodiments, the reagent pipette assembly accesses the reservoir well at the same location, and the carousel can rotate the reservoir wells to the location accessible by the reagent pipette assembly. In other embodiments, the carousel rotates to position reagent wells such that the reagent pipette assembly accesses reservoir wells at different locations.

In some embodiments, the carousel has dedicated waste pathways to direct liquid into a drain without risk of contamination to other adjacent wells. In at least some embodiments of the technology, the carousel includes spillways configured to allow fluid (e.g., cleaning liquid, reagent, etc.)

to flow from the reservoirs wells to prevent cross-contamination (e.g., flow of fluid between adjacent reservoir wells). The spillways can have the same radial length to inhibit or prevent recirculation of the waste stream into an adjacent well. In one embodiment, the carousel can include a plurality of overflow partitions that are individually positioned circumferentially between adjacent reservoir wells. In one example, the overflow partitions extend upwardly and radially inward from the reservoir wells. The carousel, in further embodiments, can include a drain and the spillways that allow an overflow of reagent to flow from the reservoir wells toward the drain.

In one embodiment, the automated slide processing apparatus includes a controller communicatively coupled to the drive mechanism and configured to command the drive mechanism such that the drive mechanism sequentially moves each of the reservoir wells to a washing position for washing by the wash pipette assembly. The controller, in some embodiments, stores and executes instructions for commanding the reagent pipette to sequentially fill the reservoir wells with reagent from reagent containers. In another embodiment, the automated slide processing apparatus includes a controller having mixing instructions that are executable to command the reagent pipette assembly such that the reagent pipette assembly delivers at least two reagents to one or more of the reservoir wells to produce a reagent mixture. In one arrangement of such an embodiment, the controller has mixed reagent dispense instructions that are executable to command the reagent pipette assembly to dispense reagent mixtures onto specimens.

Further embodiments of the technology are directed to methods of sequentially delivering reagents to a plurality of reservoir wells of a carousel to produce reagent mixtures. The carousel can be rotatable to sequentially position the reservoir wells at one or more wash positions. The method can also include at least partially filling a reagent pipette with the reagent mixture from one of the reservoir wells while at least one of the reservoir wells is located at the wash position(s). The reagent pipette assembly can partially aspirate multiple reagents from either one of the reservoir wells (pre-mixed) or multiple wells for a single or multiple shot dispense onto one or more slides. After at least partially filling the reagent pipette with reagent, the method can further include robotically moving the reagent pipette toward the microscope slide and dispensing the reagent onto the microscope slide. In yet further embodiments, the method can include rotating the carousel such that one of the reservoir wells containing reagent (e.g., excess or residual reagent) is located at the wash position, and washing the reservoir well at the wash position to remove the reagent.

At least some embodiments of the technology are directed to automated specimen processing systems capable of processing specimens carried on slides. At least some embodiments include an automated specimen processing system comprising a slide ejector assembly. The slide ejector assembly can include a slide staging device configured to receive a slide. The slide ejector assembly can also include a slide alignment device configured to engage the slide at a plurality of contact points to move the slide from a misaligned position to an aligned position. In one embodiment, the slide alignment device can include a first aligning member and a second aligning member positioned opposite the first aligning member. The first and second aligning members can be movable between an open position for receiving a slide and a closed position for aligning and/or holding the slide.

The first aligning member, in some embodiments, can include a first contact region and a second contact region for engaging a first edge of the slide. The second aligning member, in some embodiments, can include a third contact region for engaging a second edge of the slide opposite the first edge. In various embodiments, the slide alignment device is configured to engage the slide at three points of contact. In one example, a point of contact can be a small discrete area of the slide contacted by one of the first, second, or third contact regions. In one embodiment, the slide can be moved from the misaligned position to the aligned position on a standby platform by pivoting the slide about a point (e.g., a midpoint) between the three points of contact. In another embodiment, moving the slide from the misaligned position to the aligned position includes aligning a slide longitudinal axis with a standby platform longitudinal axis.

In some embodiments, an over-travel inhibitor and a slide holding region positioned between the over-travel inhibitor and slide ejector. The over-travel inhibitor can be positioned, for example, to inhibit movement of the slide past the slide holding region. In one embodiment, the over-travel inhibitor includes a vacuum port positioned to draw a vacuum between a slide and the standby platform as the slide is moved across at least a portion of the standby platform. In another embodiment, the over-travel inhibitor can include a sensor for detecting a presence of the slide on the standby platform.

At least some embodiments of the automated specimen processing system include at least one specimen processing station and a transfer head configured to transport slides from a standby platform to specimen processing station. The transfer head, in one embodiment, can include a head alignment feature receivable by at least one of a corresponding alignment feature of the slide staging device and/or an alignment feature of the specimen processing station. In one embodiment, the head alignment feature includes a first alignment pin and a second alignment pin and the corresponding alignment feature of the slide staging device includes a first opening and a second opening positioned to receive the first alignment pin and the second alignment pin, respectively. The transfer head, in further embodiments, can include a capture feature configured to engage the slide and transport the slide in the aligned position. For example, the capture feature can include a vacuum port positioned to draw a vacuum between an upper surface of the slide and the transfer head as the slide is transported.

At least some embodiments of an automated specimen processing system include a controller communicatively coupled to the slide ejector assembly. The controller, for example, can be programmed to command the slide alignment device to move the first aligning feature in a first direction toward a standby platform and to move a second aligning feature in a second direction opposite the first direction toward the standby platform to engage a slide at a plurality of contact points to move the slide. The controller can also be programmed to command the slide alignment device to move the first aligning feature in the second direction and the second aligning feature in the first direction to release the slide in the aligned position. In another embodiment, the controller can be programmed to control a transfer head to align with the slide staging device and to transport the slide from the standby to a specimen processing station.

At least some of the embodiments of the technology are directed to an automated specimen processing system comprising a slide staging device and a transfer head. In one embodiment, the slide staging device can include a standby platform configured to receive a microscope slide and an alignment device having a first aligning member and a second aligning member positioned opposite the first aligning member. The alignment device, in some embodiments, is configured to engage the microscope slide at a plurality of contact points for moving the slide from a misaligned position to an aligned position. In some arrangements, the transfer head can be configured to transport microscopes slides from the standby platform to a specimen processing station. The transfer head, for example, can have a head alignment feature receivable by at least one of a corresponding alignment feature of the slide staging device and/or an alignment feature of the specimen processing station. In various embodiments, the first aligning member can have a first contact region and a second contact region for engaging a first edge of the microscope slide, and the second aligning member can have a third contact region for engaging a second edge of the microscope slide opposite the first edge.

Some of the embodiments of the technology are directed to methods of transporting specimen-bearing microscope slides in an automated processing system. In one embodiment, the method comprises sequentially moving a plurality of specimen-bearing microscope slides from a carrier to a slide staging device. The individual specimen-bearing microscope slides can be aligned with a longitudinal axis at the slide staging device by engaging the individual specimen-bearing microscope slides at a plurality of contact points. Optionally, after moving individual specimen-bearing microscope slides from the carrier to the slide staging device, a vacuum is drawn through an over-travel inhibitor to capture the specimen-bearing microscope slide on a standby platform of the slide staging device, and detecting the presence of the slide on the standby platform. In some embodiments, the method further includes transporting the individual specimen-bearing microscope slides from the slide staging device to one or more specimen processing stations.

In some embodiments, transporting individual specimen-bearing microscope slides includes aligning a transfer head of a transport assembly with the slide staging device and picking up the individual specimen-bearing microscope slides from the slide staging device while maintaining the aligned position. In other embodiments, prior to transporting the individual specimen-bearing microscope slides, alignment features of a transport assembly can be aligned with corresponding alignment features at the slide staging device. In further embodiments, transporting the individual specimen-bearing microscope slides includes drawing a vacuum between the individual specimen-bearing slides and a transport assembly configured to transport the specimen-bearing slides to the one or more specimen processing stations.

At least some embodiments of the technology are directed to biological specimen processing systems capable of processing specimens carried on slides. The specimen processing systems can sequentially deliver slides and opposables to specimen processing stations. The specimen processing stations can use opposables to manipulate and direct a series of liquids to the specimens. The liquids can be manipulated over and/or across the slide surfaces in conjunction with capillary action while the specimen processing stations control the processing temperatures for histology staining, immunohistochemical staining, in situ hybridization staining, or other specimen processing protocols. In some embodiments, the opposables are surfaces or opposable elements capable of manipulating one or more substances on a slide. Manipulating a substance in the form of a fluid can include spreading the fluid, displacing a thin film of fluid, or otherwise altering a bolus of fluid, a band of fluid, or a thin film.

At least some embodiments of the technology are directed to a system that contacts a biological specimen with a liquid by moving an opposable in contact with the liquid. A distance separating a non-planar (e.g., curved), wetted surface of the opposable and a slide carrying the specimen is sufficient to form a liquid meniscus layer between the wetted surface and the slide. The meniscus layer contacts at least a portion of the biological specimen and is moved across the slide using capillary and other manipulative action.

The meniscus layer, in some embodiments, can be a relatively thin fluid film, a band of fluid, or the like. The opposable is movable to different positions relative to the slide and can accommodate different volumes of liquid forming the meniscus layer. The capillary action can include, without limitation, movement of the meniscus layer due to the phenomenon of the liquid spontaneously creeping through the gap between the curved, wetted opposable surface and the slide due to adhesive forces, cohesive forces, and/or surface tension. The opposable can manipulate (e.g., agitate, displace, etc.) the liquid to process the specimen using relatively small volumes of a liquid to help manage waste and provide consistent processing. Evaporative losses, if any, can be managed to maintain a desired volume of liquid, reagent concentration, or the like. Relatively low volumes of liquids can be used to process the specimens for a reduced liquid waste.

In some embodiments, a system includes one or more automated slide holders that can heat individual slides via conduction to produce temperature profiles across slides that compensate for heat losses. The heat losses can be caused by evaporation of liquid in a gap between a slide and an opposable disposed proximate to the slide. In one embodiment, the slide holder has a slide support surface and produces a non-uniform temperature profile along the slide support surface contacting the slide such that a specimen-bearing surface of the slide has a substantially uniform temperature profile when the slide is located on the slide support surface. In some embodiments, a non-uniform temperature profile is produced across the slide support surface while a substantially uniform temperature profile is produced along the mounting surface of the slide. Another feature of at least some embodiments of the present technology is that the slide holder can be configured to produce a low temperature heating zone and a high temperature heating zone surrounding the low temperature heating zone. The high temperature zone can compensate for relative high evaporative heat losses to keep the specimen at a generally uniform temperature.

At least some embodiments include a specimen processing system comprising a slide ejector assembly for removing slides from a slide carrier. The slide ejector assembly includes a carrier handler, a slide staging device, and an actuator assembly. The carrier handler is configured to receive and hold a slide carrier holding a plurality of slides. The slide staging device includes a standby platform and a slide alignment device configured to move a slide at the standby platform from a misaligned position to an aligned position. The actuator assembly includes a slide ejector positioned to move relative to the slide carrier to transfer individual slides from the slide carrier to the standby platform. The slides can thus be transferred to the standby platform without the use of, for example, mechanical gripper or suction cup devices that pull slides from one location to another location.

The carrier handler, in some embodiments, is configured to move the slide carrier relative to the slide ejector so as to sequentially stage one of the slides for delivery to the standby platform. In some embodiments, the carrier handler includes a carrier receiver and a receiver rotator. The receiver rotator is capable of rotating the slide carrier from a vertical slide orientation to a horizontal slide orientation. In one embodiment, the carrier handler includes a carrier receiver movable between a load position for loading a slide carrier and a slide unload position. The carrier handler can comprise a receiver rotator and a transport device. The receiver rotator is coupled to the carrier receiver and is operable to move the slide carrier held by the carrier receiver from a vertical slide orientation to a horizontal slide orientation. The transport device is configured to vertically move the slide carrier, which is in the horizontal slide orientation, between the slide ejector and the standby platform.

The slide staging device, in some embodiments, includes an ejector stop positioned to prevent movement of the slide ejector past an end of a slide holding region of the standby platform. The slide ejector can be movable from a first position to a second position. In some embodiments, the slide ejector moves through the slide carrier to push slides out of the slide carrier.

The standby platform can include a slide holding region and an over-travel inhibitor. The slide holding region is positioned between the over-travel inhibitor and the slide ejector. The slide ejector is positioned to move slides one at a time from the slide carrier toward the over-travel inhibitor. In some embodiments, the over-travel inhibitor includes a vacuum port positioned to draw a vacuum between a slide and the standby platform as the slide is moved by the slide ejector across at least a portion of the standby platform.

The slide alignment device, in some embodiments, includes a pair of jaws movable between an open position for receiving a slide and a closed position for aligning the slide. In one embodiment, the jaws center the slide relative to a raised slide holding region of the standby platform when the jaws move from the open position to the closed position.

The actuator assembly includes a reciprocating drive mechanism coupled to the slide ejector and configured to move the slide ejector so as to push a slide out of the slide carrier and onto the standby platform. In some embodiments, the slide ejector is moveable across a slide carrier receiving gap that is between the actuator assembly and the slide staging device.

The specimen processing system, in some embodiments, can further include one or more specimen processing stations and one or more transfer heads. The transfer heads can be configured to transport slides from the standby platform to one of the specimen processing stations. In some embodiments, at least one of the transfer heads can have a head alignment feature receivable by at least one of an alignment feature of the slide staging device and/or an alignment feature of the specimen processing station. In some embodiments, the head alignment feature includes a first alignment pin and a second alignment pin. The alignment feature of the slide staging device can include a first opening and a second opening. The first opening and the second opening are positioned to receive the first alignment pin and the second alignment pin, respectively. In some embodiments, the alignment feature of the specimen processing station can include a first opening and a second opening, and the first opening and the second opening are positioned to receive the first alignment pin and the second alignment pin, respectively, of the head alignment feature.

The specimen processing system, in some embodiments, can further include a controller communicatively coupled to the slide ejector assembly. The controller can be programmed to command the actuator assembly to move a first slide that is positioned below a second slide from the slide carrier to the standby platform and being programmed to move the second slide to the standby platform after moving the first slide to the standby platform.

In some embodiments, a method of transporting specimen-bearing microscope slides includes delivering a carrier containing a plurality of specimen-bearing microscope slides to an ejector assembly. The carrier moves toward a slide staging device of the ejector assembly. The specimen-bearing microscope slides are sequentially moved from the carrier to the slide staging device. The slide staging device moves from a receive slide configuration to an align slide configuration to move the individual specimen-bearing microscope slides at the slide staging device to an aligned position. The individual specimen-bearing microscope slides are transported from the slide staging device of the ejector assembly to one or more specimen processing stations.

The carrier, in some embodiments, can be rotated to move the plurality of specimen-bearing microscope slides from a first orientation to a second orientation. In some embodiments, the first orientation is a substantially vertical orientation and the second orientation is a substantially horizontal orientation.

The specimen-bearing microscope slides, in some embodiments, can be sequentially moved from the carrier to the slide staging device by pushing the specimen-bearing microscope slides onto and along the slide staging device. Additionally or alternatively, a lowermost specimen-bearing microscope slide held by the carrier to the slide staging device. This process can be repeated until most or all of the slides have been removed from the slide carrier.

In certain embodiments, individual specimen-bearing microscope slides can be carried from the slide staging device to the specimen processing stations which are configured to individually process the specimen-bearing microscope slides. Additionally or alternatively, the specimen-bearing microscope slides can be sequentially moved from the carrier to the slide staging device by moving a first specimen-bearing microscope slide from the carrier to the slide staging device. After transporting the first specimen-bearing microscope slide away from the slide staging device, a second specimen-bearing microscope slide is transported from the carrier to the slide staging device.

The slide staging device, in some embodiments, can be moved from the receive slide configuration to the align slide configuration by moving a pair of jaws from an open position to a closed position to contact and move a specimen-bearing microscope slide positioned between the jaws from a misaligned position to an aligned position. In certain embodiments, the jaws can center the slide relative to a raised portion of the slide stage device upon which the slide rests.

The specimen-bearing microscope slides, in some embodiments, are sequentially moved from the carrier by (a) pushing the specimen-bearing microscope slide at the slide ejection position such that the specimen-bearing microscope slide moves onto the slide staging device and (b) repeating process (a) until the carrier is empty. In one embodiment, an elongated ejector is moved through the carrier (e.g., a basket) to push the slides onto the slide staging device.

A vacuum can be drawn between the individual specimen-bearing microscope slides and the slide staging device. For example, a sufficient vacuum can be drawn to inhibit or limit movement of the slide along the slide staging device. The vacuum can be reduced or eliminated to remove the slide from the slide staging device.

The carrier, in some embodiments, is a slide rack that includes shelves that hold specimen-bearing microscope slides in a spaced apart arrangement. The specimen-bearing microscope slides can be sequentially moved from the carrier to the slide staging device by indexing the shelves at a slide removal position adjacent to a platform of the slide staging device. In some embodiments, a slide at the slide removal position is slightly higher than the slide staging device.

The specimen-bearing microscope slides can be sequentially moved from the carrier by (a) reciprocating a slide ejector between an initial position and an eject position to move at least one of the specimen-bearing microscope slides from the carrier to the slide staging device and (b) repeating process (a) to remove at least most of the specimen-bearing microscope slides from the carrier. In some embodiments, all the specimen-bearing microscope slides are removed from the carrier using the slide ejector.

In some embodiments, a slide processing apparatus for processing a specimen carried by a slide includes a staining module. The staining module includes a slide holder platen, an opposable element, and an opposable actuator. The slide holder platen has a first sidewall, a second sidewall, and a slide receiving region between the first sidewall and the second sidewall. A slide is positioned on the slide receiving region. The slide includes a first edge and an opposing second edge. The opposable element is disposed proximate to the slide and includes a first edge portion and an opposing second edge portion. The opposable actuator holds the opposable element to form a capillary gap between the opposable element and the slide. The first edge portion of the opposable element is closer to the first sidewall than the first edge of the slide. The second edge portion of the opposable element is closer to the second sidewall than the second edge of the slide.

The slide processing apparatus, in some embodiments, includes a dispenser positioned to deliver a supplemental liquid between the opposable element and the slide while a liquid is held in the gap there between. Additionally, the slide processing apparatus can include a controller communicatively coupled to the dispenser and programmed to command the dispenser such that the dispenser delivers the supplemental liquid to keep a volume of liquid between the opposable element and the slide within an equilibrium volume range. In some embodiments, the controller is programmed to deliver supplemental liquid at a predetermined rate. In one embodiment, the predetermined rate is equal to or less than about 110 μL per minute at a temperature of about 37° C. for bulk liquids. In some embodiments, the predetermined rate is equal to or less than about 7 μL per minute at a temperature of about 37° C. for non-bulk reagents. The rate can be selected based on the specimen staining protocol being processed.

The slide processing apparatus, in some embodiments, further comprises a plurality of additional staining modules and a controller configured to independently control each of the staining modules. The staining modules can use disposable or reusable opposable elements to spread and move reagents across the specimens.

The first edge portion of the opposable element can extend past the first edge of the slide toward the first sidewall. The second edge portion of the opposable element can extend past the second edge of the slide toward the second sidewall. The opposable element can include a mounting end having at least one slot dimensioned to be received and retained by at least a portion of the opposable actuator. In some embodiments, the opposable element has a captivation end and an arcuate main body extending from the captivation end. The arcuate main body is configured to roll along the slide to move a liquid across the surface of the slide. The captivation end has a radius of curvature equal to or less than about 0.08 inch. Other dimensions can also be used.

The staining module can include at least one heating element positioned to conductively heat the first sidewall, the second sidewall, or both. The opposable actuator is moveable to roll a curved portion of the opposable element along the slide to move a band of a liquid across at least a portion of the slide carrying a specimen. The first and second sidewalls can be used to heat the slide, specimen, and/or liquid while the band of liquid is manipulated across the specimen.

The slide processing apparatus, in some embodiments, can include a contact surface of the slide receiving region that supports a slide such that the edge portions of the slide extend outwardly from edges of the opposable.

In some embodiments, a system for processing a specimen carried by a slide comprises a specimen processing station and a controller. The specimen processing station includes an opposable actuator and a slide holder platen. The slide holder platen includes a slide support region and a liquid replenishment device. The slide holder platen is configured to heat a liquid on a slide at the slide support region while an opposable element held by the opposable actuator contacts and moves the liquid across the slide surface. The replenishment device is configured to deliver a supplemental liquid between the opposable element and the slide. The controller is programmed to control the specimen processing station such that the replenishment device delivers the supplemental liquid at a replenishing rate to compensate for evaporative losses of the liquid.

The controller, in some embodiments, includes one or more memories and a programmable processor. The memory stores a first sequence of program instructions and a second sequence of program instructions. The programmable processor is configured to execute the first sequence of program instructions in order to process a specimen on the slide with a first liquid and configured to execute the second sequence of program instructions to process the specimen with a second liquid that is different from the first liquid. In some embodiments, the programmable processor is configured to execute the first sequence of program instructions in order to heat the slide to a first temperature using the slide holder platen, and the controller is configured to execute the second sequence of program instructions in order to heat the slide to a second temperature using the slide platen, the second temperature is different from the first temperature.

The controller, in some embodiments, is configured to execute a first sequence of program instructions to command the replenishment device to deliver a first liquid to the slide at a first rate. The controller is further configured to execute a second sequence of program instructions to command the replenishment device to deliver a second liquid to the slide at a second rate that is different from the first rate. In certain embodiments, the first rate corresponds to an evaporation rate of the first liquid, and the second rate corresponds to an evaporation rate of the second liquid. The controller can help moderate evaporative losses.

The controller, in some embodiments, includes a memory that stores a replenishment program executable by the controller in order to keep a volume of the liquid on the slide within an equilibrium volume range. In certain embodiments, the equilibrium volume range is about 70 µL to about 260 µL. In certain embodiments, the controller is programmed to command the specimen processing station to keep a volume of the liquid between a maximum equilibrium volume corresponding to an over-wetting condition and a minimum equilibrium volume corresponding to an under-wetting condition. The controller, in some embodiments, is programmed to command the specimen processing station to move a volume of the liquid across a specimen held on the slide by moving an opposable element held by the opposable actuator relative to the slide and can also be programmed to deliver the supplemental liquid from the replenishment device to generally compensate for a decrease in the volume of the liquid due to evaporation.

The controller, in some embodiments, is configured to receive reference evaporation rate information (e.g., evaporation rate information for the liquid) from a memory and to control the specimen processing station based on the reference evaporation rate information. Additionally or alternatively, the controller can be programmed to command the specimen processing station such that the replenishment device provides the supplemental liquid at a rate selected based on an evaporation rate of the liquid.

The system for processing a specimen, in some embodiments, further comprises an opposable element and a controller. The opposable element is held by the opposable actuator and can extend outwardly past edges of the slide. The controller is programmed to control the specimen processing station to move the opposable element while the opposable element manipulates the liquid across the slide while an evaporation rate of the liquid is kept equal to or less than about a predetermined rate (e.g., 7 µL per minute, 5 µL per minute, or the like at about 37° C.).

The slide holder platen, in some embodiments, includes a heating element that receives electrical energy and outputs thermal energy to heat the slide via conduction. The heating element can include one or more resistive heating elements.

In some embodiments, a method of processing a specimen carried by a slide comprises heating a liquid on a slide held by a slide holder. The opposable element is rolled to contact the liquid on the slide and to move the liquid across a biological specimen on the slide. A replenishing rate is determined based on an evaporation rate of the liquid. A supplemental liquid is delivered based on the replenishing rate to substantially compensate for evaporative losses of the liquid. The opposable element, which contacts the liquid comprising the supplemental liquid, is rolled so as to repeatedly contact the specimen with the liquid.

The volume of the supplemental liquid delivered onto the slide can be equal to or greater than a decrease in the volume of the liquid via evaporation. Additionally or alternatively, the supplemental liquid can be delivered onto the slide by delivering the supplemental liquid to keep a volume of the liquid on the slide equal to or greater than a minimum equilibrium volume and at or below a maximum equilibrium volume. Additionally or alternatively, the supplemental liquid can be delivered onto the slide while the opposable element rolls along the slide.

In some embodiments, a method of processing a specimen on a slide includes moving a liquid along a slide using an opposable element contacting the liquid. The temperature of the liquid on the slide is controlled while moving the liquid. At least one of a volume of the liquid and/or a total evaporation rate of the liquid is evaluated, and a supplemental liquid is delivered onto the slide based on the evaluation to keep the volume of the liquid on the slide within an equilibrium volume range. In certain embodiments, the volume of the liquid and the total evaporation rate of the liquid and be received from a memory to evaluate the volume of the liquid and the total evaporation rate of the liquid from a memory evaluating the at least one of the volume of the liquid and/or the total evaporation rate of the liquid includes receiving. The equilibrium volume range can be about 125 µL to about 175 µL.

In some embodiments, a slide processing apparatus comprises a slide holder platen and an opposable actuator. The slide holder platen has a receiving region configured to receive a slide with a first side of the slide facing the receiving region and a second side facing away from the receiving region. The opposable actuator is positioned to hold an opposable element to define a capillary gap between the opposable element and a slide surface located at the receiving region. The opposable actuator is configured to advance the capillary gap in a first direction along the slide to move a band of liquid across the length and width of the second side of the slide from a first position to a second position and to narrow the band of liquid (e.g., decrease a width of the band of liquid in a direction substantially parallel to the first direction).

The opposable actuator, in some embodiments, is configured to alternatingly roll the opposable element along the slide in the first direction and a second direction opposite the first direction to manipulate the band of liquid across the surface of the slide between the first position and the second position. The band of liquid at the first position is between an end of the opposable element and the slide, and the band of liquid at the second position is between the opposable element and an end of the slide. The band of liquid can be narrowed at each of the first position and the second position prior to moving the band of liquid to the other of the first position and second position. The opposable actuator, in some embodiments, is a variable bandwidth compression opposable actuator configured to decrease the width of the band a predetermined amount. The predetermined amount can be selected by a controller or an operator.

The opposable actuator, in some embodiments, is configured to move the opposable element relative to the slide to reduce the width of the band of liquid at an end of an opening defined by an end of at least one of the slide and/or the opposable element by at least 50%, 40%, or 25%. Additionally or alternatively, the opposable actuator can be configured to move the opposable element to displace the band of liquid between the first position and the second position while maintaining the latitudinal width of the band of liquid. The opposable actuator, in some embodiments, is moveable between a first configuration in which the band of liquid is narrowed at a first end of an opening between the opposable element and an end of the slide and a second configuration in which the band of liquid is narrowed at a second end of the opening. The opposable actuator, in some embodiments, is movable to an over-roll configuration to move a first side of the band of liquid toward a second side of the band of liquid to decrease the width of the band of liquid while the second side of the band of liquid is held substantially stationary at an end of one of the opposable element and the slide.

The slide processing apparatus, in some embodiments, further comprises a staining module and a controller. The staining module comprises the slide holder platen and the opposable actuator. The controller is communicatively coupled to the staining module. The controller is programmed to command the staining module to move the opposable element to move the capillary gap.

The slide processing apparatus, in some embodiments, further comprises an opposable element including a mounting end held by an opposable receiver of the opposable actuator, a captivating end opposite the mounting end, and a main body. The main body is between the mounting end and the captivating end. The captivating end cooperates with the slide to accumulate the liquid at an end of a mounting surface of the slide proximate to a label on the slide as the mounting end is moved away from the slide.

The slide processing apparatus, in some embodiments, further comprises an opposable element having a tapered end facing the receiving region. The tapered end is positioned to contact and captivate the band of liquid. In certain embodiments, the tapered end includes a rounded region extending between opposite longitudinally extending edges of the opposable element.

The opposable actuator, in some embodiments, has a rolling state to roll the opposable element along the slide to move the band of liquid from a location at an end of an opening defined by an end of the slide and the opposable element to a location at an opposing end of the opening. The opposable actuator can have a static state to keep the opposable element stationary relative to the slide to perform, for example, incubation.

The slide processing apparatus, in some embodiments, further comprises a slide supported by a contact surface of the receiving region such that the slide extends laterally outward past opposing edges of the contact surface. The slide can carry one or more specimens.

The slide processing apparatus, in some embodiments, further comprises an opposable element held by the opposable actuator. The opposable element has a curved captivation end. The captivation end can have a radius of curvature equal to or less than about 0.08 inch. In certain embodiments, the opposable element has an arcuate body for rolling along the slide at the receiving region.

In some embodiments, a slide processing apparatus comprises a slide holder platen and an opposable actuator. The opposable actuator includes an opposable receiver and a drive mechanism. The opposable receiver is positioned to hold an opposable element to form a capillary gap between the opposable element and a slide held by the slide holder platen. The drive mechanism has a rolling state for rolling the opposable element in a first direction along the slide to move a band of liquid to an end of a space between the opposable element and the slide. The drive mechanism has an over-rolling state for rolling the opposable element in the first direction to decrease a width of the band of liquid captivated at the end of the space.

The opposable actuator, in some embodiments, is configured to move the opposable element to move the band of liquid across at least most of a mounting surface of the slide. The width of the band of liquid can be decreased by moving at least a portion of the opposable element away from the slide. The width of the band of liquid is in a direction substantially parallel to a longitudinal axis of the slide.

In some embodiments, a method for processing a specimen carried by a slide comprises delivering a slide and an opposable element to a staining module. The opposable element held by the staining module is positioned relative to the slide held by the staining module to hold a liquid in a capillary gap between the slide and the opposable element. The opposable element is moved relative to the slide to displace the liquid in a first direction that is substantially parallel to the longitudinal axis of the slide and toward an end of an opening between the slide and the opposable element. The opposable element is moved relative to the slide to reduce a width of a band of the liquid in the first direction while the band of liquid is captivated at the end of the opening.

The band of liquid, in some embodiments, is alternatingly moved between the end of the opening and an opposing end of the opening by rolling the opposable element along the slide in the first direction and a second direction opposite the first direction. The opposable element can include one or more gapping elements for maintaining spacing between a main body of the opposable element and the slide.

The band of liquid, in some embodiments, is spread to increase the width of the band of liquid. The spread band of liquid can be moved across a specimen on the slide. In certain embodiments, the width of the band of liquid is reduced at one end of the capillary gap prior to moving the band of liquid to the other end of the gap.

The method for processing the specimen, in some embodiments, further comprises captivating substantially all of the liquid at the end of the gap while reducing the width of the band of liquid.

The method for processing the specimen, in some embodiments, further comprises displacing the band of liquid across a specimen on the slide while maintaining the width of the band of liquid.

The method for processing the specimen, in some embodiments, further comprises reducing the width of the band of liquid by at least 50% by moving the opposable element relative to the slide. A volume of the liquid can be equal to or greater than about 75 µL.

The width of the band of liquid, in some embodiments, is less than a length of the band of the liquid. The width of the band of liquid is substantially parallel to the longitudinal axis of the slide. The length of the band of liquid is substantially perpendicular to the longitudinal axis of the slide.

In some embodiments, a slide heating apparatus comprises a support element and a heater. The support element has a support surface configured to support a slide with a back side of the slide facing the support surface and a specimen-bearing surface of the slide opposite the back side of the slide. The heater is coupled to the support element. The slide heating apparatus is configured to deliver thermal energy non-uniformly across the support surface to the back side of the slide via conduction to substantially compensate for non-uniform heat losses associated with evaporation of a liquid on the specimen-bearing surface.

The heater, in some embodiments, is positioned to deliver heat to the slide via the support element to produce a substantially uniform temperature profile along a specimen-bearing portion of the specimen-bearing surface. In some embodiments, the substantially uniform temperature profile has less than a 5% temperature variation across the specimen-bearing portion of the specimen-bearing surface. In some embodiments, the substantially uniform temperature profile has less than a 4° C. temperature variation across the specimen-bearing surface. Other temperature profiles can also be achieved.

The heater, in some embodiments, includes at least two spaced apart elongate portions for conductively heating side portions of the support surface and two end heating portions of the support surface extending between the elongate portions. The two end heating portions are positioned to heat both a portion of the support surface for contacting an end of the slide and a portion of the support surface for contacting a region of the slide adjacent to a label of the slide.

The slide heating apparatus, in some embodiments, is configured to produce a low heating zone along a central region of the support surface and a high heating zone along the support surface. The high heating zone can surround (e.g., circumferentially surround) the low heating zone.

The slide heating apparatus, in some embodiments, further comprises a convection assembly positioned to produce a convective flow that passes through a pocket defined by the heater to cool the support element. In some embodiments, the convection assembly includes one or more fans. The convective flow can cool the support element without flowing across the specimen on the slide.

The slide heating apparatus, in some embodiments, further comprises a pair of sidewalls each having a thermally conductive portion and an insulating portion. The thermally conductive portion facing the slide to heat the slide.

The slide heating apparatus, in some embodiments, further comprises an overmolded holder comprising an insulating material. The support element is positioned between and supported by sidewalls of the overmolded holder. The insulating material can have a thermal conductivity that is less than a thermal conductivity of a material of the support element. In some embodiments, the insulating material comprises a non-metal material (e.g., plastic) and the support element comprises metal.

In some embodiments, at least one of the heater and the support element comprises mostly stainless steel by weight. In some embodiments, the support surface comprises stainless steel. In some embodiments, most of the support element between the support surface and the heater is stainless steel. The portion of the support element between the slide and the heater can have a thermal conductivity equal to or less than about 20 W/m*K.

In some embodiments, a method for heating a biological specimen carried on a slide includes positioning a slide on a support element of a conductive slide heating apparatus such that a back side surface of the slide faces the support element and a specimen-bearing surface of the slide faces away from the support element. Heat can be delivered non-uniformly across the back side surface of the slide via the support element to substantially compensate for evaporative heat losses associated with evaporation of a liquid on the specimen-bearing surface. The evaporative heat losses are non-uniform across the specimen-bearing surface of the slide.

A non-uniform temperature profile, in some embodiments, can be produced along a support surface of the support element contacting the back side surface of the slide such that the specimen-bearing surface has a temperature profile that is more uniform than the non-uniform temperature profile. In some embodiments, a temperature variation (e.g., a temperature variation maintained across a portion of the specimen-bearing surface contacting a biological specimen) can be equal to or less than about 5° temperature variation while a support surface of the support element contacting the back side surface of the slide has more than a 5° temperature variation.

A support surface of the support element can contact the back side surface of the slide and can be heated to produce a low heating zone at a central region of the support surface and a high heating zone at a region of the support surface surrounding the central region. Additionally or alternatively, the support surface can be heated to produce the high heating zone along a perimeter of a staining area along the specimen-bearing surface and a low heating zone at a central region of the staining area.

The slide can be conductively heated using thermal energy produced by a heating element of the conductive slide heating apparatus. The heating element includes at least two spaced apart elongate heating portions and two end heating portions extending between the elongate heating portions. The elongate heating portions and the end heating portions define a convection cooling pocket for cooling the support element.

In some embodiments, a system for heating a specimen-bearing slide including a slide platen including a support element, a conductive heater, and a controller. The support element has a support surface. The conductive heater is positioned to heat the support element. The controller is programmed to control the system to produce a non-uniform heating profile along the support element so as to transfer thermal energy to a slide to produce a substantially uniform temperature profile along a specimen-bearing area of a specimen-bearing surface of the slide when a back side of the slide contacts the support surface.

The conductive heater, in some embodiments, is configured to heat the support element to produce the non-uniform temperature heating profile across most of the support surface supporting the slide such that the substantially uniform temperature heating profile is produced along most of the specimen-bearing surface of the slide. The substantially uniform temperature profile has less than a 5° temperature variation across the specimen-bearing area of the slide. Additionally or alternatively, the conductive heater can be configured to produce a central low temperature heating zone along the support element and a peripheral high temperature heating zone along the support element. Additionally or alternatively, the conductive heater is positioned underneath the support element and defines an opening through which a convective flow is capable of passing to cool the support element.

The system for heating a specimen-bearing slide, in some embodiments, includes a convection cooling device coupled to the controller and configured to deliver a convective flow into the opening based on a signal from the controller. In certain embodiments, the convection cooling device includes at least one fan capable of producing the convective flow. In some embodiments, compressed air or motive air can be used.

The support element, in some embodiments, comprises stainless steel. In some embodiments, a portion of the support element between the support surface for carrying the slide and the conductive heater has a thermal conductivity equal to or less than about 20 W/m*K.

In another embodiment the method can further comprise detecting a presence of the individual specimen-bearing microscope slides at the slide staging device.

In another embodiment, prior to transporting the individual specimen-bearing microscope slides, the method further comprises aligning alignment features of a transport assembly with corresponding alignment features at the slide staging device.

In another embodiment the method can further comprise transporting the individual specimen-bearing microscope slides includes drawing a vacuum between the individual specimen-bearing slide and a transport assembly configured to transport the specimen-bearing slides to the one or more specimen processing stations while in the aligned position.

In one embodiment an automated slide processing apparatus is configured to apply at least one reagent to a specimen carried by a microscope slide, the automated slide processing apparatus comprising a support element having a support surface; at least one vacuum port; and a sealing member having a non-round shape as viewed from above, wherein the sealing member in an uncompressed state extends upwardly beyond the support surface and in a compressed state is configured to maintain an airtight seal with a backside of the microscope slide when the microscope slide is pulled against the support surface by a vacuum drawn via the at least one vacuum port.

In another embodiment the sealing member has a rounded-corner rectangular shape or a rectangular shape as viewed from above.

In another embodiment the sealing member has a rounded-corner polygonal shape or a polygonal shape as viewed along an axis generally perpendicular to the support surface.

In another embodiment at least a portion of the support element extends between the sealing member and the at least one vacuum port, wherein the portion has a non-round shape as viewed from above.

In another embodiment the support element includes a trench, and the sealing member includes a compliant gasket having a main body and a lip, wherein the main body is positioned in the trench, and wherein the lip extends radially outward from the main body.

In another embodiment when the microscope slide is drawn against the support surface, the lip is configured to be spaced apart from a sidewall of the trench but capable of physically contacting the sidewall of the trench to inhibit movement of the microscope slide relative to the support element.

In another embodiment the lip is configured to physically contact the sidewall when the microscope slide is rotated at least about 2 degrees about a vertical axis surrounded by the sealing member.

In another embodiment the lip in an uncompressed configuration extends upwardly from the trench, wherein the lip in a compressed configuration extends toward a sidewall of the trench, and wherein the lip is movable between the uncompressed configuration and the compressed configuration without contacting the sidewall of the trench.

In another embodiment the sealing member in a compressed configuration is positioned on one side of a plane in which a backside surface of the microscope slide is located when the microscope slide is pulled against the support surface, and the sealing member in an uncompressed configuration is located on both sides of the plane.

In another embodiment the support element includes a vacuum surface surrounded by the at least one vacuum port, wherein the vacuum surface is spaced apart from and positioned below the plane such that the vacuum surface and the microscope slide at least partially define a vacuum chamber with a height less than a height of the sealing member.

In yet another embodiment the sealing member includes a lip configured to deflect primarily in a direction perpendicular to a backside surface of the microscope slide during use.

In another embodiment the lip is movable between an uncompressed configuration for contacting the slide that is moving toward the support surface and a compressed configuration for maintaining the airtight seal, wherein the lip in the uncompressed position extends upwardly beyond the upper surface, and wherein the lip in the compressed position is positioned at or below the upper surface.

In another embodiment the lip is configured to be deflected as the microscope slide moves toward the support surface to form the airtight seal.

In another embodiment the sealing member is positioned to be located under a label of the microscope slide.

In another embodiment the automated slide processing apparatus can further comprise a vacuum source in fluid communication with the at least one vacuum port and configured to draw a sufficient vacuum to maintain the airtight seal. It may also comprise a heater configured to heat the support element such that the support element conductively heats the microscope slide while the sealing member maintains the airtight seal.

One embodiment is a method for holding a microscope slide, comprising positioning a microscope slide on a support element such that a specimen-bearing portion of the slide is supported by a first portion of the support element and a label-bearing portion of the slide is supported by a second portion of the support element, wherein the first portion surrounds the second portion and a sealing member is positioned between the first and the second portions; and drawing a vacuum through the second portion while a sealing member contacts the slide.

Another embodiment includes drawing a sufficient vacuum to form an airtight seal between the sealing member and the slide to inhibit at least one of translational or rotational movement of the slide relative to the support element.

Another embodiment includes forming a vacuum chamber between the second portion and a backside of the microscope slide.

Another embodiment includes contacting a top portion of the sealing member such that the top portion of the sealing member deflects in a direction that is generally perpendicular to a backside surface of the slide.

In one embodiment an automated slide processing apparatus for dispensing liquids onto one or more microscope slides comprises a carousel including a plurality of reservoir wells; a reagent pipette assembly including a reagent pipette movable between at least one loading position for obtaining reagent from one of the reservoir wells and at least one dispense position for dispensing reagent onto one of the microscope slides; a wash pipette assembly configured to wash the plurality of reservoir wells; and a drive mechanism coupled to the carousel and configured to rotate the carousel to position the reservoir wells relative to the reagent pipette assembly and/or the wash pipette assembly.

In another embodiment the automated slide processing apparatus further comprises a filling station including a plurality of containers holding reagents; and a plurality of slide processing stations; wherein the reagent pipette assembly is movable through an internal chamber of the automated slide processing apparatus to transport reagent obtained at the filling station to the carousel and to dispense reagent mixtures from the carousel onto one of microscope slides which are at the slide processing stations.

In another embodiment automated slide processing apparatus the drive mechanism is configured to sequentially rotate the reservoir wells underneath a wash pipette of the wash pipette assembly.

In another embodiment the reagent pipette assembly has a reagent load state for obtaining reagent from the one of the reservoir wells while the wash pipette assembly delivers wash liquid to another one of the reagent wells.

In another embodiment the reagent pipette assembly is configured to fill the reagent pipette with reagent from any one of the reservoir wells.

In another embodiment a controller is communicatively coupled to the drive mechanism and configured to command the drive mechanism such that the drive mechanism sequentially moves each of the reservoir wells to a washing position for washing by the wash pipette assembly.

In another embodiment the controller stores and executes instructions for commanding the reagent pipette assembly to fill the reservoir wells with reagent from reagent containers.

In another embodiment further comprises a controller having mixing instructions that are executable to command the reagent pipette assembly such that the reagent pipette assembly delivers at least two reagents to one of the reservoir wells to produce a reagent mixture.

In another embodiment the controller has mixed reagent dispense instructions that are executable to command the reagent pipette assembly to dispense the reagent mixture onto a specimen.

In another embodiment the reagent pipette assembly is movable between a filling position for obtaining reagent from a container at a filling station and a dispensing position for filling one or more of the reservoir wells with reagent from the filling station.

In another embodiment the wash pipette assembly is fluidically coupled to a vacuum source, and the wash pipette assembly draws liquid from one of the reservoir wells when the vacuum source draws a vacuum.

In another embodiment the automated slide processing apparatus has a mixing mode in which the reagent pipette assembly mixes reagents within one of the reservoir wells and dispenses the reagent mixture onto one of the microscope slides.

In another embodiment the wash pipette assembly includes a pipette movable into each of the reservoir wells.

In another embodiment the carousel includes spillways configured to allow reagent to flow from the reservoirs wells while preventing flow of reagent between adjacent reservoir wells.

In another embodiment the carousel includes a plurality of overflow partitions, wherein each overflow partition is positioned circumferentially between adjacent reservoir wells.

In another embodiment the overflow partitions extend upwardly and radially inward from the reservoir wells.

In another embodiment the carousel includes a drain and a plurality of spillways that allow an overflow of reagent to flow from the reservoir wells toward the drain.

In another embodiment the reservoir wells are angularly spaced apart from one another with respect to an axis of rotation of the carousel.

In another embodiment the reservoir wells include one or more groups of reservoir wells with uniform radial spacing relative to a center of the carousel.

In another embodiment the automated slide processing apparatus further comprises a filling station including a plurality of containers holding reagents; and a slide processing station including a slide holder platen having a receiving region configured to receive a slide with a first side of the slide facing the receiving region and a second side facing away from the receiving region; and an opposable actuator positioned to hold an opposable element to define a capillary gap between the opposable element and a slide located at the receiving region, the opposable actuator being configured to move the capillary gap in a first direction along the slide to move a band of liquid along the second side of the slide from a first position to a second position and to decrease a width of the band of liquid in a direction substantially parallel to the first direction, wherein the reagent pipette assembly is movable through an internal chamber of the automated slide processing apparatus to transport reagent obtained at the filling station to the carousel and to dispense reagent mixtures from the carousel onto a microscope slide at the slide processing station.

In one embodiment a method of dispensing liquid onto a microscope slide comprises sequentially delivering reagents to a plurality of reservoir wells of a carousel to produce reagent mixtures, wherein the carousel is rotatable to sequentially position the reservoir wells at a wash position; at least partially filling a reagent pipette with one of the reagent mixtures from one of the reservoir wells while at least one of the reservoir wells is located at the wash position; after at least partially filling the reagent pipette with reagent, robotically moving the reagent pipette toward the microscope slide and dispensing the reagent onto the microscope slide; and washing at least one of the reservoir wells when the at least one reservoir well is located at the wash position.

Another embodiment further comprises rotating the carousel to position one of the reservoir wells containing reagent at the wash position; and washing the reservoir well at the wash position to remove the reagent.

BRIEF DESCRIPTION OF THE DRAWINGS

Non-limiting and non-exhaustive embodiments are described with reference to the following drawings. The same reference numerals refer to like parts or acts throughout the various views, unless otherwise specified.

FIG. 34A is a front, top, left side isometric view of a slide holder platen holding a slide in accordance with an embodiment of the disclosed technology.

FIG. 34B is a front, top, left side isometric view of the slide holder platen of FIG. 34A ready to hold a slide in accordance with an embodiment of the disclosed technology.

DETAILED DESCRIPTION OF DRAWINGS

Figure 1:
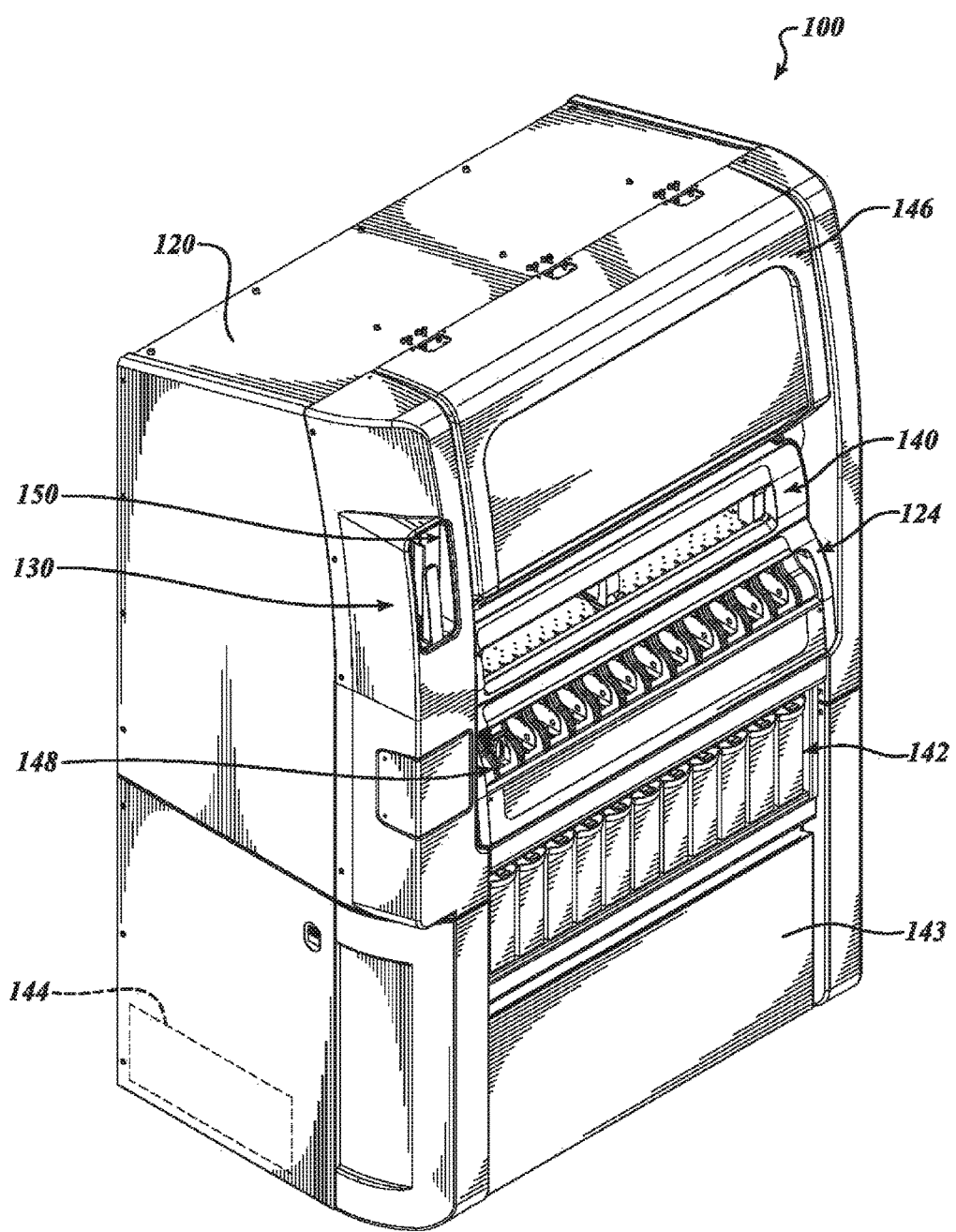
FIG. 1 is an isometric view of a specimen processing system in accordance with an embodiment of the disclosed technology.

FIG. 1 shows a specimen processing system 100 ("system 100") including a protective housing 120, a slide carrier parking station 124 ("parking station 124"), an opposable carrier loading station 130 ("loading station 130"), and reagent parking stations 140, 142. The system 100 can automatically process specimen-bearing slides using opposables loaded via the loading station 130 to perform, for example, specimen conditioning (e.g., cell conditioning, washing, deparaffinizing, etc.), antigen retrieval, staining (e.g., H&E staining), or other types of protocols (e.g., immunohistochemistry protocols, in situ hybridization protocols, etc.) for preparing specimens for visual inspection, fluorescent visualization, microscopy, microanalyses, mass spectrometric methods, imaging (e.g., digital imaging), or other analytical or imaging methods. The system 100 can simultaneously process 20 specimen-bearing slides using the same or different protocols to provide processing flexibility and a relatively high throughput. The specimens can remain on the slides throughout processing (e.g., baking through staining) for convenient handling and preventing cross-contamination.

The protective housing 120 inhibits, limits, or substantially prevents contaminants from entering an internal processing environment. The protective housing 120 can include a cover 146 that can be opened to access internal components, including, without limitation, robotic components (e.g., robotic arms), transport devices (e.g., conveyors, actuators, etc.), fluidic components, specimen processing stations, slide platens, mixing components (e.g., mixing wells, reagent trays, etc.), slide carrier handling components, opposable carrier handling components, dryers, pressurization devices (e.g., pumps, vacuum devices, etc.), or the like.

The parking station 124 includes a row of bays. A slide carrier in the form of a basket is positioned in a left bay 148. Each bay can be configured to receive other types of slide carriers, such as racks, baskets, trays, or other types of carriers suitable for carrying slides before, during, or after specimen processing. The illustrated parking station 124 includes 12 bays separated by dividers. The number of bays, positions of bays, bay orientations, and bay configurations can be selected based on the types of slide carriers to be used.

The loading station 130 includes a receiving opening 150 through which a user can load an opposable carrier. The opposable carrier can be a magazine that holds a stack of opposable elements. In other embodiments, the opposable carriers can be cartridges, or other portable structures for carrying opposables.

The parking stations 140, 142 each includes a row of bays. Each bay can hold one or more containers, including bulk reagent containers, bottles, bag-in-box reagent containers, or the like. The parking station 142 can hold bulk liquid containers that provide liquids used in larger volumes, such as wash solutions. Empty containers in the parking stations 140, 142 can be conveniently replaced with full containers.

Figure 2:
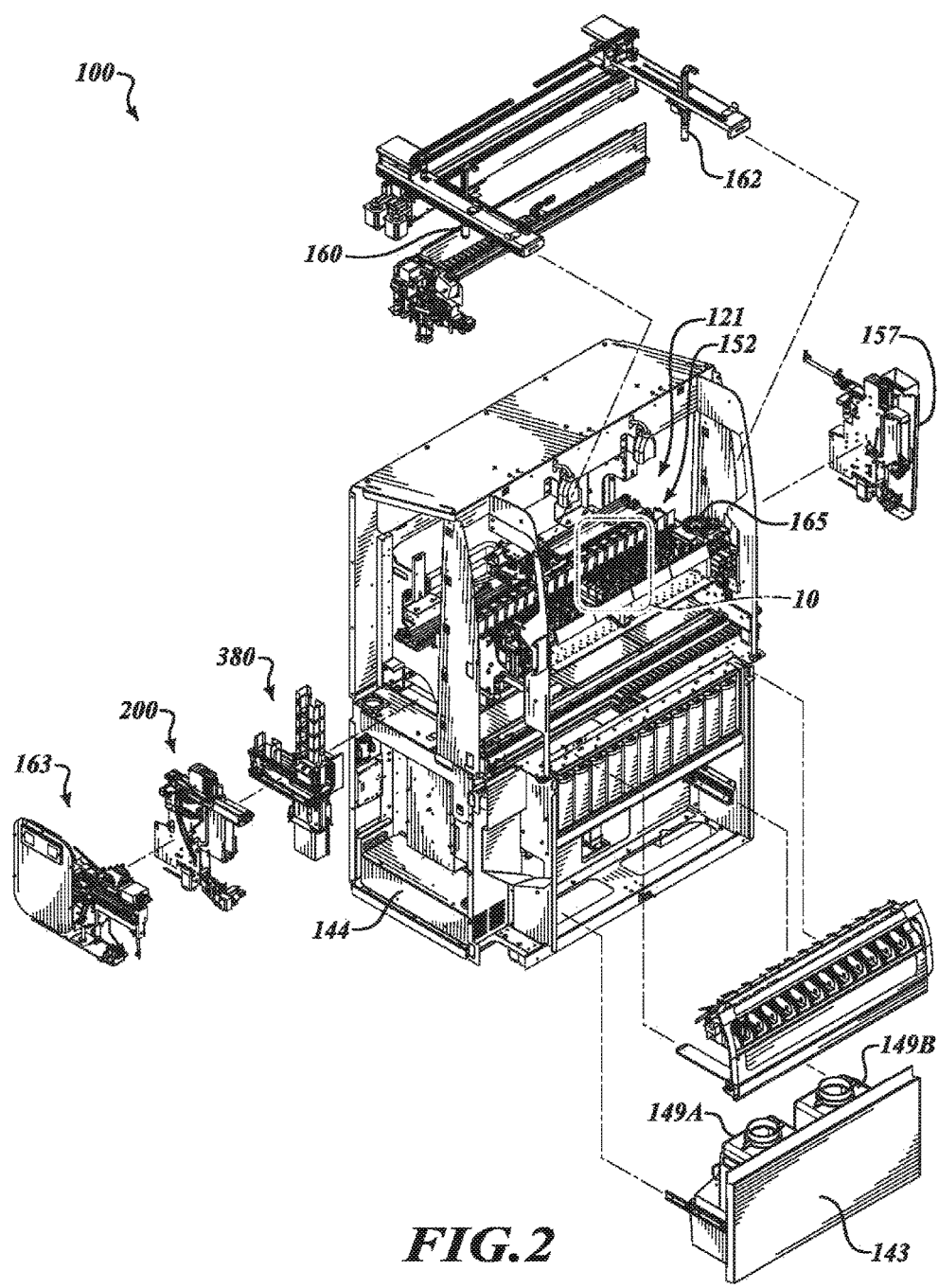
FIG. 2 is an exploded isometric view of the specimen processing system of FIG. 1. Portions of a protective housing are shown removed.

Fluid movement into, out of, and within specimen processing stations can be controlled by a fluidics module that includes, for example, pumps, valves, and filters. A pneumatics module can supply pressurized air and generate vacuums to perform various slide processing operations and to move fluids throughout the system 100. Waste can be delivered to a waste drawer 143. FIG. 2 shows the waste drawer 143 holding waste containers 149A, 149B. The pneumatics module can deliver waste from the specimen processing stations to the containers 149A, 149B, which can be emptied periodically.

A controller 144 can command system components and can generally include, without limitation, one or more computers, central processing units, processing devices, microprocessors, digital signal processors (DSPs), application-specific integrated circuits (ASICs), readers, and the like. To store information, the controller 144 can include, without limitation, one or more storage elements, such as volatile memory, non-volatile memory, read-only memory (ROM), random access memory (RAM), or the like. The stored information can include heating programs, optimization programs, tissue preparation programs, calibration programs, indexing programs, mixing programs, or other executable programs. Optimization programs can be executed to optimize performance (e.g., enhance heating, reduce excess reagent consumption, increase productivity, enhance processing consistency, or the like). The processing may be optimized by determining, for example, an optimum schedule to (1) increase processing speeds, (2) reduce the time of heating or cooling cycles, (3) increase throughput (e.g., increase the number of slides processed in a certain length of time), and/or (4) reduce reagent waste. In some embodiments, the controller 144 determines loading sequences for loading the specimen processing stations to reduce processing times and to determine loading sequences of the dispensers. This saves time because fluids can be dispensed onto the next specimen-bearing slide as soon as a specimen-bearing slide is removed from the specimen processing station. In some embodiments, the controller 144 determines sequences for mixing and dispensing reagent using the mixing station 165.

FIG. 2 is an isometric exploded view of the specimen processing system 100 including a processing station 163, a slide ejector assembly 200, an opposable dispenser 380, and a specimen return mechanism 157. The processing station 163, the slide ejector assembly 200, and the opposable dispenser 380 are positioned at the left side of an internal environment 121. The specimen return mechanism 157 is positioned at the right side of the internal environment 121. A mixing station 165 is positioned generally below the specimen return mechanism 157 and can include reservoirs (e.g., reservoir wells). Reagents can be mixed in the mixing station 165. In other embodiments, the mixing station 165 can hold containers (e.g., vials, beakers, etc.) in which substances are stored and/or mixed. A row 152 of 20 specimen processing stations can independently process biological specimens.

In operation, a user can load slide carriers carrying specimen-bearing slides into the empty bays of the parking station 124 of FIG. 1 and can load opposable carriers carrying opposables into the loading station 130. The slide carriers can be transferred to a reader (e.g., a label reader, a barcode reader, etc.), not shown that reads labels, if any, on the slides. The slide carriers can be delivered to the processing station 163 which can include, without limitation, a dryer (e.g., a dehydration unit), a heating unit (e.g., a baking module), or other component capable of removing water from the slides, heating specimens (e.g., heating specimens to adhere the specimens to the slides), or the like. In some embodiments, the processing station 163 blows hot air over slides to dry the slides, and if the specimens contain paraffin, the hot air can soften the paraffin to promote adhesion of the specimens to the slides. An air system can partially recirculate air to control the humidity in the processing station 163. Slide carriers can be picked up and transported from the processing station 163 to another module (e.g., a specimen processing station, a label reader, etc.) or returned to one of the bays of the parking station 124.

The specimen return mechanism 157 can load specimen-bearing slides into a slide carrier. The loaded slide carriers can be transported to the parking station 124. If the slide carriers are compatible with an automated coverslipper, a user can transport the slide carriers from the parking station 124 to an automated coverslipper for coverslipping. Alternatively, the slides can be manually coverslipped. The coverslipped slides can be analyzed using optical equipment, e.g., a microscope or other optical devices.

Figure 3:
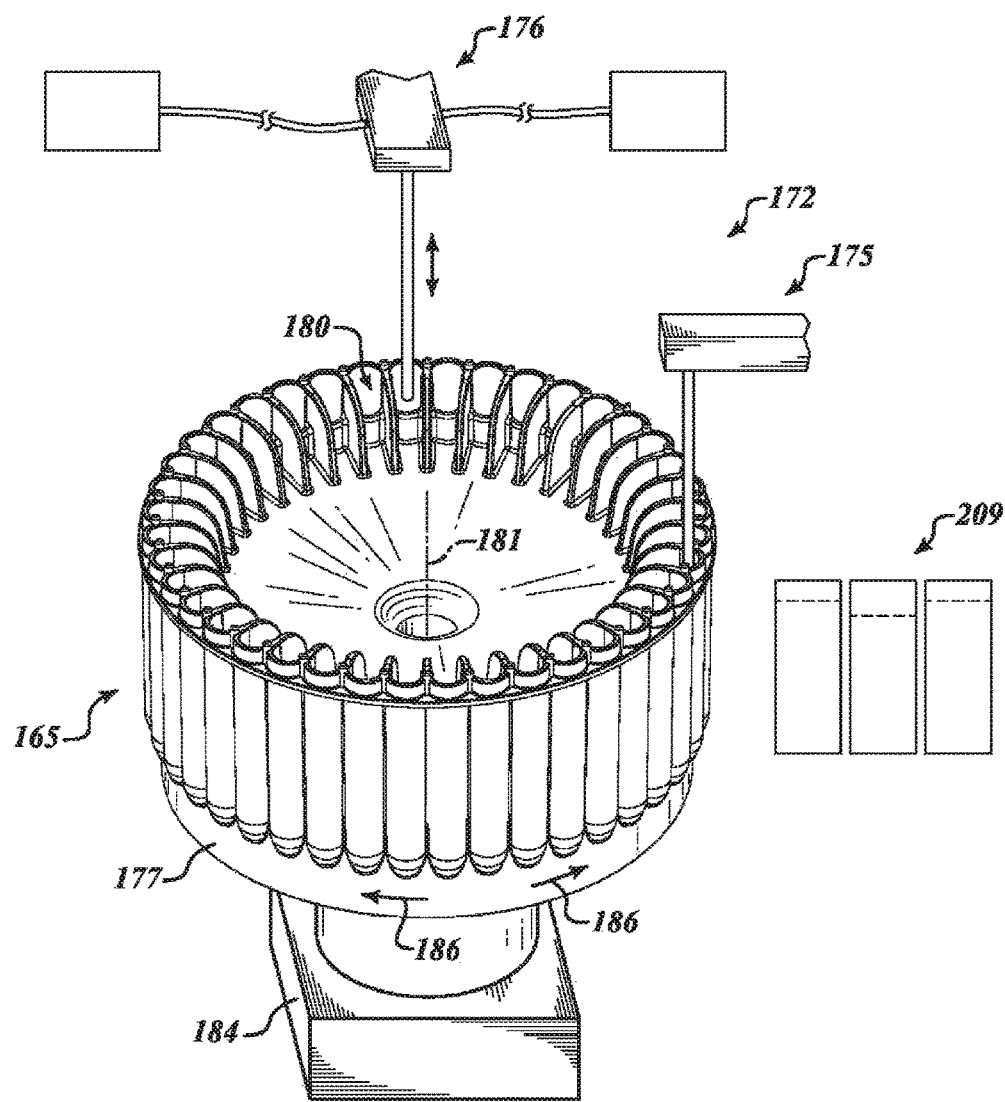
FIG. 3 is an elevational view of a pipette apparatus with a mixing station in accordance with an embodiment of the disclosed technology.

FIG. 3 is an elevational view of a pipette apparatus 172 in accordance with an embodiment of the disclosed technology. The pipette apparatus 172 can serve as a staging area to provide improved stain characteristics, significantly increase processing capacity, or otherwise enhance processing. The pipette apparatus 172 can prepare and hold volumes of reagent (e.g., individual reagents and/or reagent mixtures). Reactive reagents can be mixed immediately before dispensing to enhance stain consistency and quality, especially for reagents that react immediately upon mixing. Because reagents can be staged well before they are needed, the pipette apparatus 172 can increase slide processing capabilities and is well suited for use with high-volume automated slide processing systems. Additionally, the pipette apparatus 172 can occupy a relative small space and provide mix and wash functionality independent of slide processing.

Generally, the pipette apparatus 172 can include a mixing station 165, a reagent pipette assembly 175, and a wash pipette assembly 176. The mixing station 165 can include a carousel 177 and a drive mechanism 184 for rotating the carousel 177 about an axis of rotation 181. The carousel 177 can include a circular array of reservoir wells 180 (one identified) configured to hold volumes of reagent. The drive mechanism 184 can rotate (indicated by arrows 186) the carousel 177 to position the reservoir wells 180 relative to the reagent pipette assembly 175 and/or wash pipette assembly 176. The reagent pipette assembly 175 can partially or completely fill the reservoir wells 180 with fresh reagent from a filling station 209 (e.g., a reagent bay) and can also dispense reagent from the reservoir wells 180 onto microscope slides. The reagent pipette assembly 175 can also wash and/or rinse the reservoir wells or perform other operations. The wash pipette assembly 176 can wash the reservoir wells 180 by, for example, rinsing the reservoir wells 180 with wash liquid and vacuuming liquid (e.g., wash liquid, reagent, etc.) out of the reservoir wells 180. Fresh reagents can be mixed in the washed reservoir wells 180.

Figure 4:
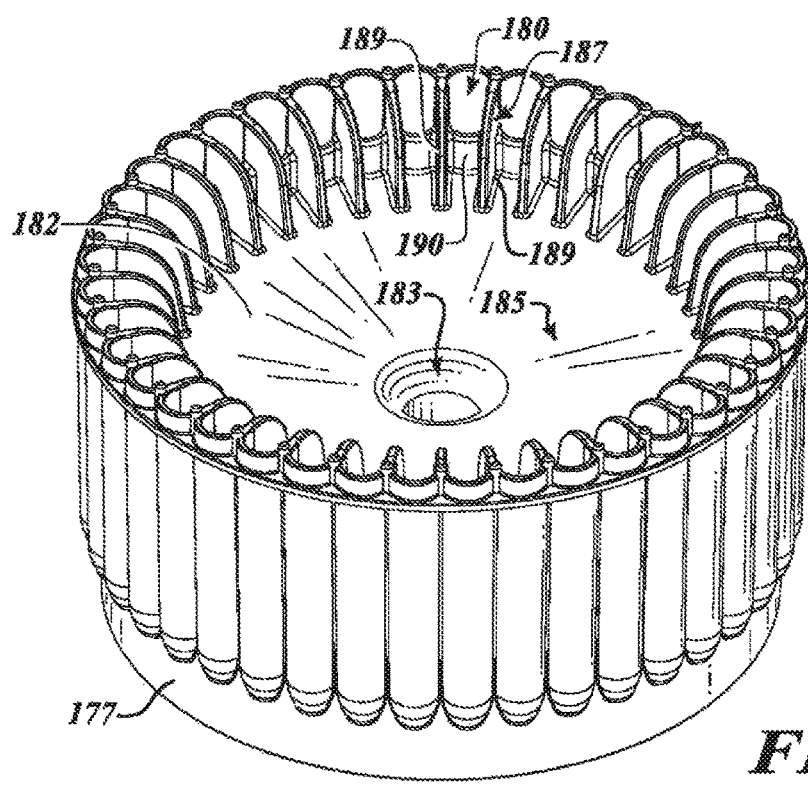
FIG. 4 is an isometric view of a carousel in accordance with an embodiment of the disclosed technology.
Figure 5:
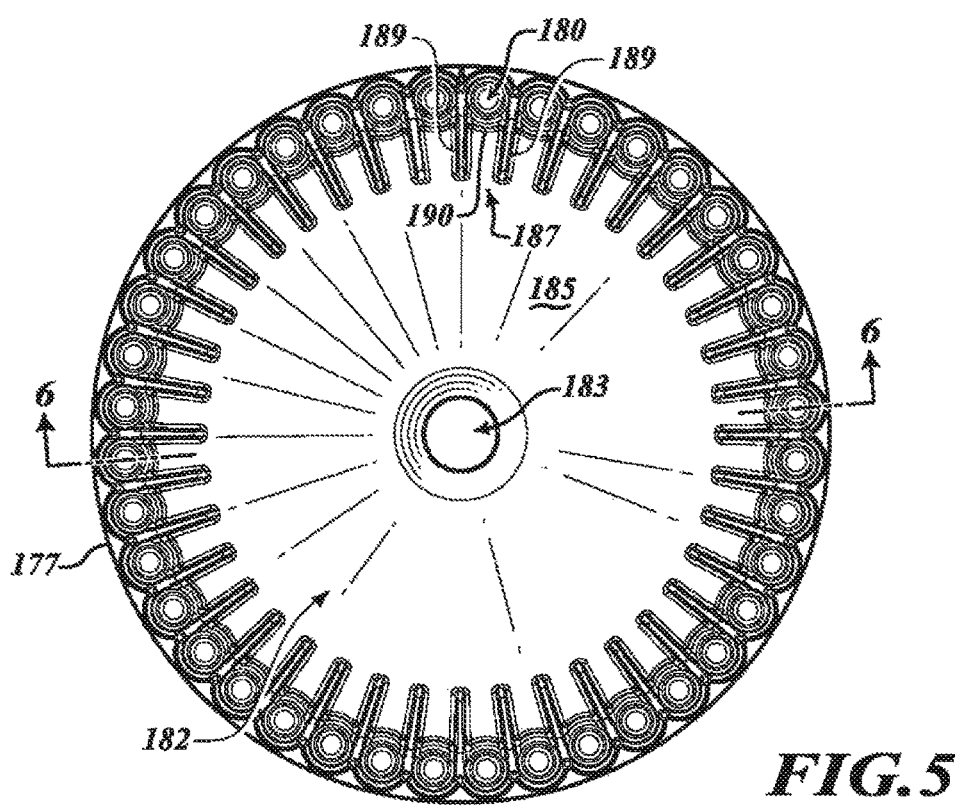
FIG. 5 is a top plan view of the carousel of FIG. 4.

FIG. 4 is a front top isometric view of the carousel 177 in accordance with an embodiment of the disclosed technology. FIG. 5 is a top plan view of the carousel 177. Referring to FIGS. 4 and 5 together, the carousel 177 can include reservoir wells 180 (one identified), a ramp 182, and a drain 183. The reservoir wells 180 can be angularly spaced (evenly or unevenly) about the drain 183, and each reservoir well 180 can hold a sufficient volume of liquid for one or multiple dispense steps in a staining protocol. In some embodiments, each reservoir well 180 has a holding capacity in a range of about 200 μL to about 450 μL. In one embodiment, each reservoir well 180 has a holding capacity of about 350 μL. In other embodiments, different reservoir wells 180 can have different holding capacities to prepare different volumes of reagent mixtures. The holding capacities of the reservoir wells 180 can be selected based on the desired volume of reagent mixtures to be dispensed. A group of reservoir wells 180 (e.g., four reservoir wells) can correspond to a particular slide and/or slide processing station to prevent cross-contamination. In a staining protocol utilizing a set number of reagent mixtures, reservoir wells (e.g., adjacent reservoir wells 180) can be used to prepare and hold the reagent mixtures. In some embodiments, the carousel 177 can include multiple arrays of wells positioned at different locations relative to the drain 183. For example, multiple circular arrays of reservoir wells can be positioned at different radii from the center drain radii of the center drain 183.

The reservoir wells 180 can be in generally vertical orientations (e.g., longitudinal axes of the reservoir wells can be oriented vertically) to access to the bottoms of the reservoir wells 180 using vertically-oriented pipettes. The reservoir wells 180 may be circular (FIG. 5), oval, elliptical, combinations thereof, or other shapes without sharp corners for convenient rinsing/cleaning. The illustrated carousel 177 has multiple reservoir wells 180 (e.g., forty reservoir wells 180) to allow rapid processing of a relatively large number of slides (e.g., up to about one hundred slides or more), but the carousel 177 can have a greater or a lesser number of reservoir wells 180 to increase or decrease the number of slides serviced by the carousel 177. The geometry (e.g., circular, elliptical, etc.), pattern (e.g., circular array, elliptical array, etc.), number, and orientations of the reservoir wells 180 can be selected based on the number of slides, staining protocols, and operation of the reagent pipette assembly 175 and/or wash pipette assembly 176.

The ramp 182 can extend between the reservoir wells 180 and the drain 183. Overflow liquid (e.g., reagent, wash liquid, or mixtures thereof) escaping the reservoir wells 180 can flow along an upper surface 185 of the ramp 182 and through the drain 183. In some embodiments, the upper surface 185 slopes downwardly toward the drain 183 and has a shape (e.g., a generally frusto-conical shape) for promoting radially inward flow. The upper surface 185 can help keep the flows from two or more reservoir wells 180 separate to inhibit or limit mixing of the flows to avoid or mitigate unintended chemical reactions. In some embodiments, the ramp 182 has flow channels, grooves, or other features that help overflow liquid flow toward the drain 183.

Referring now to FIG. 4, the carousel 177 can include spillways 187 (one identified) configured to allow overflow liquid to automatically drain from the reservoir wells 180. The spillways 187 can prevent cross-contamination by preventing well to well flooding. During a wash cycle, the reservoir wells 180 can be flooded with wash liquid (e.g., water, deionized water, washing solution, etc.) without affecting adjacent reservoir wells 180. In some embodiments, the spillway 187 includes overflow partitions 189 (two identified in FIGS. 4 and 5) and an overflow wall 190. Each partition 189 can be positioned between adjacent reservoir wells 180.

Figure 6:
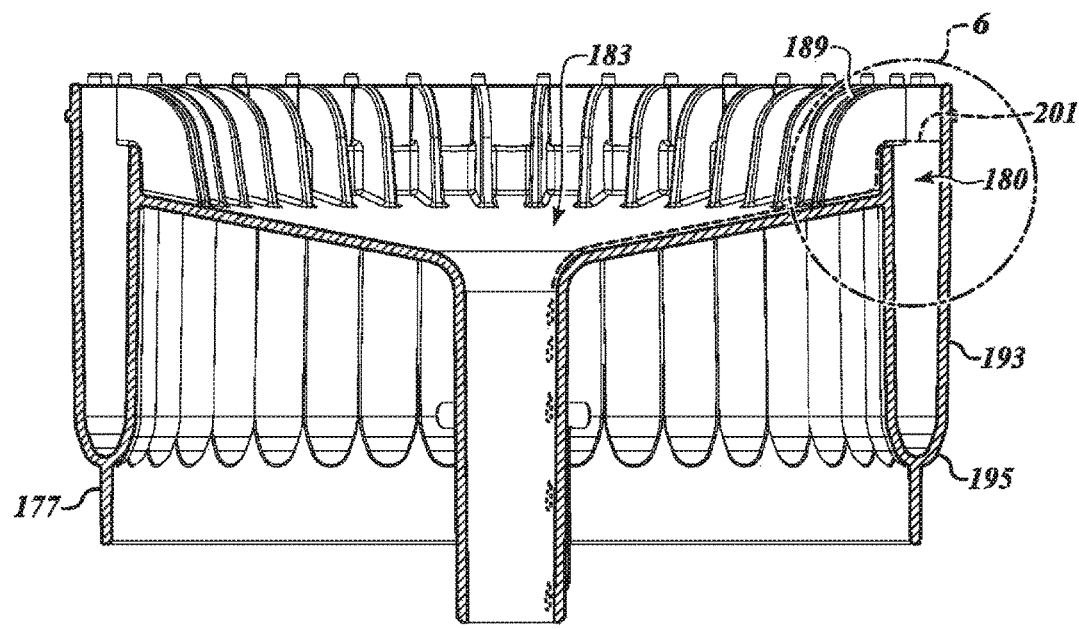
FIG. 6 is a cross-sectional view of the carousel taken along line 6-6 of FIG. 5.
Figure 7:
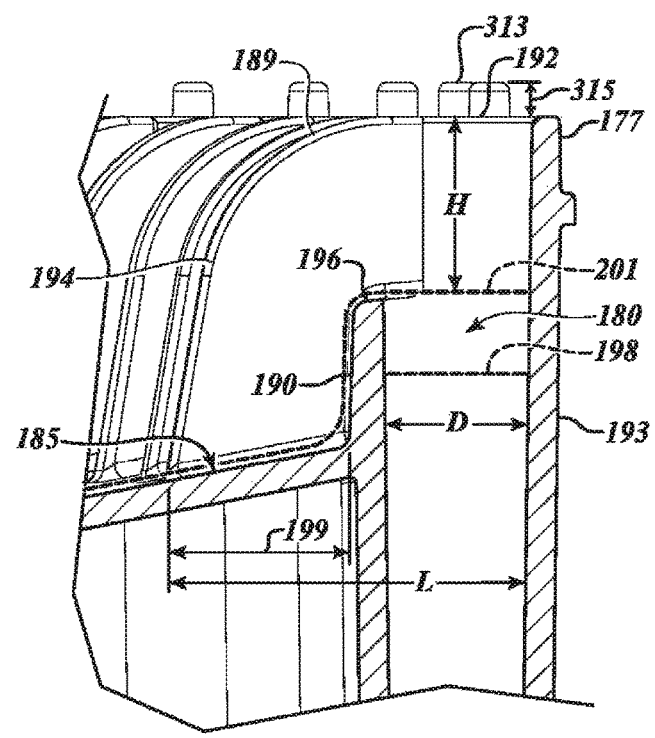
FIG. 7 is a detailed view of a portion of the carousel of FIG. 6.

FIG. 6 is a cross-sectional view of the carousel 177 taken along line 6-6 of FIG. 5. FIG. 7 is a detailed view of a portion of the carousel 177. Referring now to FIG. 7, the partition 189 can prevent splattering liquid from reaching nearby reservoir wells and can include an outer portion 192 and an inner portion 194. In some embodiments, the partition 189 can be positioned between the center of an adjacent reservoir well 180 and other reservoir wells (e.g., ⅕, ¼, of ⅓ of the total number of reservoir wells 180). During a wash cycle, wash liquid may tend to spray and/or splatter, and the partition 189 can block such spray/splatter, thereby preventing cross-contamination between wells. The dimensions and configurations of the partitions 189 can be selected to keep the reservoir wells fluidically isolated from one another.

The outer portion 192 can be positioned directly between two reservoir wells and can extend upwardly past a spillway entrance in the form of a rim 196 of the wall 190. In some embodiments, the outer portion 192 extends upwardly past the rim 196 a sufficient distance to prevent well to well flooding. For example, the height H of the outer portion 192 can be in a range of about 3 mm to about 7 mm. Other heights can be used, if needed or desired. The inner portion 194 can be a generally vertically-oriented wall that extends inward (e.g., toward the center of the carousel 177). A length 199 of the inner portion 194 can be generally equal to the height H to prevent directing liquid (e.g., rinse liquid or reagent) toward an unintended well at the risk of cross contamination. The length L of the partition 189 can be equal to or greater than the diameter D of the reservoir well 180. For example, a ratio of the length L to the diameter D can be equal to or greater than 1.25, 1.5, 2, or 2.5.

The reservoir well 180 has a generally smooth sidewall 193 (e.g., a cylindrical sidewall or other shaped sidewall without sharp corners) and a bottom 195 (FIG. 6) that define a chamber capable of holding a desired a volume, for example, 250 μL, 350 μL, or 450 μL. FIG. 7 shows a fluid level line 198 (illustrated in phantom line) of a desired volume of reagent. When excess liquid is delivered to the reservoir well 180, the liquid can rise above the entrance 196 of the spillway 180 and cause flooding. As shown in FIG. 7, the liquid 201 (illustrated in phantom line) can flow over the wall 190 and along the upper surface 185. Referring now to FIG. 6, the liquid 201 can exit the carousel 177 via the drain 183, which can be sufficiently large to accommodate fluid draining from multiple reservoir wells. Flooding can intentionally occur to rinse the reservoir wells and may unintentionally occur, for example, if excess reagent is dispensed into one of the reservoir wells.

FIG. 7 shows stops 313 (one identified) that limit the maximum depth of plunge of pipettes to prevent damage to the carousel 177 that could be caused by, for example, an over-insertion of the pipette. The stops 313 can be circumferentially spaced apart from each other and can extend upwardly a sufficient distance 315 to prevent the wash pipette 213 and/or reagent pipette 204 from contacting the reservoir well bottom 195. For example, a head assembly carrying the pipette can strike the stop 313 before the pipette carried by the head assembly damages the carousel 177. Other types of stops can be used to position or limit movement of the pipettes.

Figure 8:
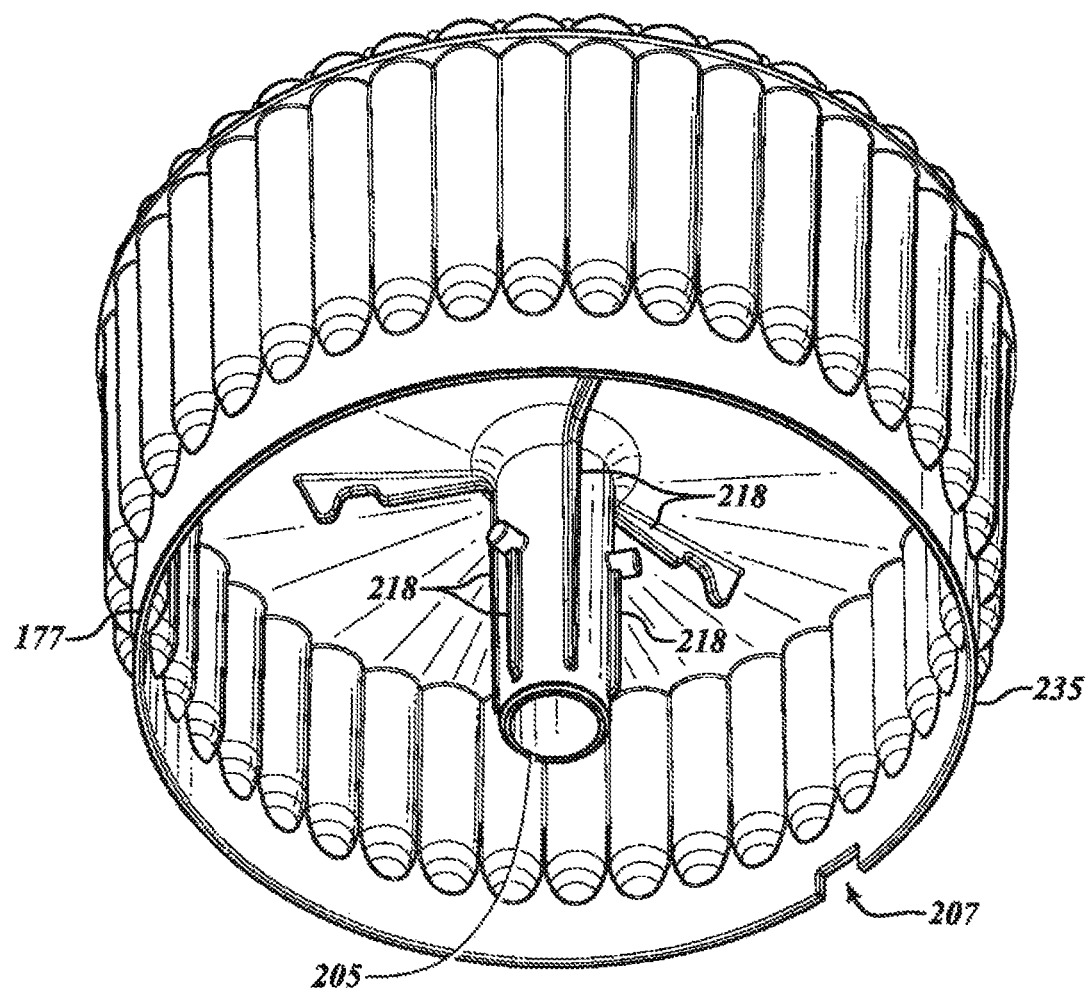
FIG. 8 is a bottom perspective view of the carousel in accordance with an embodiment of the disclosed technology.

FIG. 8 is a bottom perspective view of the carousel 177 that includes a mounting bayonet 205 and an alignment feature 207. The mounting bayonet 205 can be coupled to a drive shaft of a drive mechanism (e.g., drive mechanism 184 of FIG. 4) and can include one or more positioners 218. In other embodiments, the outer surface of the carousel 177 can be used to rotate the carousel 177. For example, a drive wheel can engage the outer surface of the carousel 177 such that rotation of the drive wheel causes rotation of the carousel 177. The positioners 218 can be flanges, ribs, or other features matable with the drive shaft of the drive mechanism. The alignment feature 207 can be used to visually, mechanically, electro-mechanically, and/or opto-mechanically align the carousel 177. In some embodiments, the alignment feature 207 is a notch or a cutout that receives an alignment protrusion of the drive mechanism. In other embodiments, the alignment feature 207 can be a protrusion or other visually (including optically) identifiable feature for convenient identification and orientation of the carousel 177. In some embodiments, the alignment feature 207 can be used to clock the carousel 177 such that individual reservoir well 180 positions are known by the control system (e.g., controller 144). A top edge or surface 231 can be located at a critical distance from the bottom of a skirt 235 in which it resides, such that if a sensor (e.g., an optical sensor) does not identify the alignment feature 207, then the user will be immediately notified that the carousel 177 is improperly installed. The carousels described herein can be conveniently removed from drive mechanism 184 to wash it or replace it, and the alignment feature 207 can be used to reinstall the carousel 177 on the drive mechanism 164. One side of the alignment feature 207 can be detected and used to notify the operator if the carousel 177 is not properly installed.

A one-piece carousel can have a unitary construction and can be formed by a molding process, machining process, or other suitable process. For example, the carousel 177 can be monolithically formed by an injection molding process. In multi-piece embodiments, the carousel 177 can have a carousel main body and separate spillways and reservoir wells that are installed in the carousel main body. The configuration of the carousel 177 can be selected based on the desired functionality of the carousel 177.

FIGS. 9A-9D show operation of the pipette apparatus 172. Generally, the reagent pipette assembly 175 can sequentially deliver fresh reagents to the reservoir wells 180 to produce reagent mixtures. The reagent pipette assembly 175 can deliver such reagent mixtures onto slides at slide processing stations. The carousel 177 can be rotated to sequentially position the reservoir wells 180 at a wash position for washing by the wash pipette assembly 176. In some embodiments, the reagent pipette assembly 175 can mix reagents while the wash pipette assembly 176 washes reservoir wells 180 to reduce overall processing times. In other embodiments, reagent mixing and reservoir well washing are performed at different times. A pipette cleaner 251 can wash (e.g., using wash liquid), vacuum, blow off, or otherwise clean the pipette 204 between each trip to the filling station 209 to prevent cross contamination of the reagents. The pipette cleaner 251 can also clean the pipette 213 between wash operations. Operation of the reagent pipette assembly 175, wash pipette assembly 176, and mixing station 165 are detailed below.

Figure 9A:
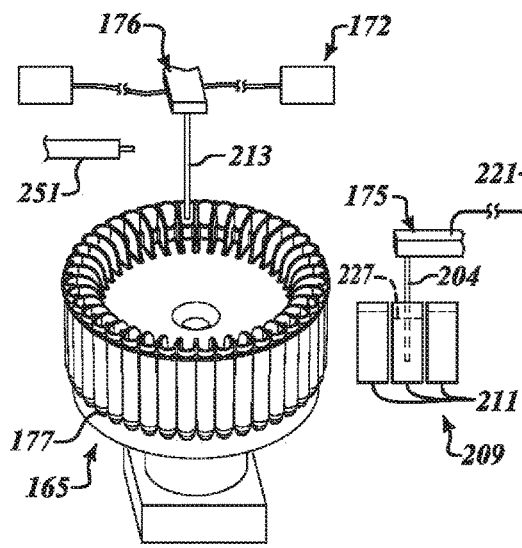
FIGS. 9A-9D illustrate stages of operation of the pipette apparatus.
Figure 9B:
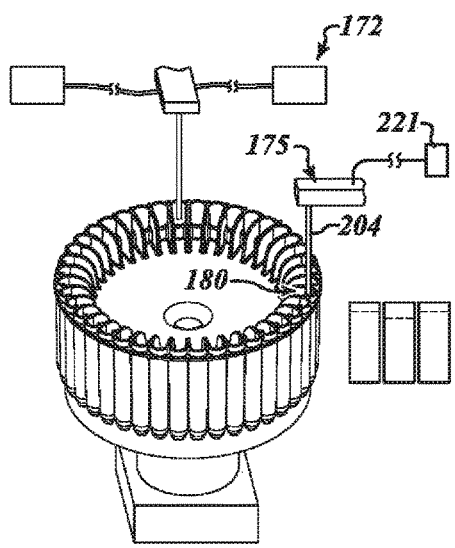
Figure 9C:
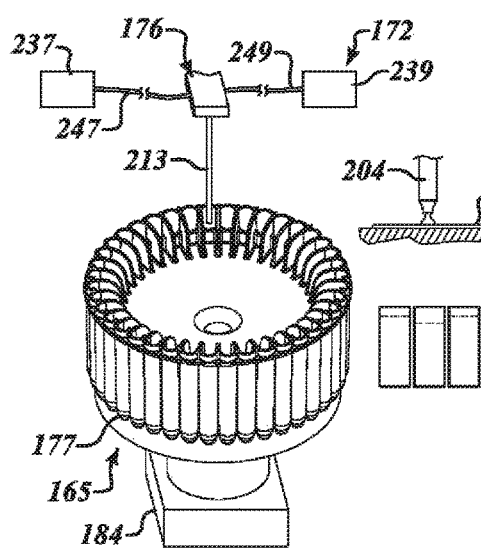

FIGS. 9A-9C show one method of utilizing the reagent pipette assembly 175. The reagent pipette assembly 175 can have different types of pipettes, valves, and sensors, and in some embodiments, can be similar or identical to the pipette dispensers 160, 162 depicted in FIG. 2. In various embodiments, the reagent pipette assembly 175 can include a positioning mechanism with one or more rail/carriage assemblies, motors (e.g., drive motors, stepper motors, etc.), drive elements (e.g., chains, belts, etc.), or other features for providing motion. The reagent pipette assembly 175 can obtain fresh reagents, stage reagents, and dispense reagents onto microscope slides. In some embodiments, the reagent pipette assembly 175 can move the reagent pipette 204 to, for example, a filling position (see FIG. 9A) at the filling station 209, an unload/load position (FIG. 9B) for either dispensing reagent into one of the reservoir wells 180 or loading the pipette 204 with reagent from one of the reservoir wells, and a dispense position (FIG. 9C) for dispensing reagent onto a slide at a slide processing system.

Referring now to FIG. 9A, the reagent pipette assembly 175 in a reagent load state of operation can insert the pipette 204 into one of the containers 211 at the filling station 209 and can draw a desired volume of fresh reagent 227. In some embodiments, the reagent pipette assembly 175 can draw a vacuum provided by a pressurization device 221. The pressurization device 221 can include one or more vacuum sources, pumps, or other devices capable of providing a desired vacuum level or positive pressure. The containers 211 can be, without limitation, vials, bottles, jars, or other containers suitable for holding substances used to process specimens. The illustrated filling station 209 has three containers 211, but a greater or lesser number of containers can be used, and the filling station 209 can be part of a parking station, such as the parking stations 140, 142 of FIG. 1. For example, the containers 211 can be installed in the bays of the parking stations 140, 142 of FIG. 1 and can be accessed by the reagent pipette assembly 175, which is movable through the internal environment 121 of FIG. 2.

FIG. 9B shows the reagent pipette assembly 175 after the reagent pipette 204 has been filled with reagent. The pipette 204 is positioned to deliver the reagent into the reservoir well 180 identified in FIG. 9B. The pressurization device 221 can provide positive pressure to dispense the reagent. The reagent pipette assembly 175 can obtain additional reagent from the filling station 209 and dispense it into the same reservoir well 180 to produce a reagent mixture.

Referring to FIGS. 9B and 9C, to dispense a reagent mixture held by the carousel 177, the reagent pipette 204 can be inserted into the reagent well 180 and filled with a desired volume of the reagent mixture. FIG. 9C shows the loaded reagent pipette 204 dispensing the reagent mixture onto a microscope slide 156 at a processing station 245. The reagent pipette assembly 175 can repeatedly obtain reagent from the mixing station 165 and dispense the reagent onto the slide 156 or other slides at other processing stations.

Figure 9D:
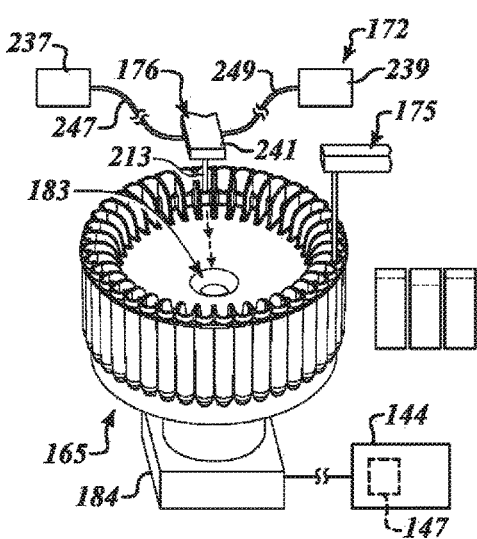

FIGS. 9C and 9D illustrate stages of a washing process performed by the wash pipette assembly 176. Generally, the reservoir wells 180 can be washed by, for example, dispensing wash liquid so as to flood the reservoir wells 180 and removing (e.g., sucking out) wash liquid, as well as any residual reagent, left in the reservoir wells 180. The wash pipette assembly 176 can include a vacuum source 237 and a pressurization device 239 connected to a wash head assembly 241 by lines 247, 249, respectively. The drive assembly 184 can rotate the carousel 177 to position the reservoir well 180 at a wash position under the wash pipette 233.

FIG. 9D shows the wash pipette 233 after it has been lowered into one of the reservoir wells. Wash liquid can be delivered through the wash pipette 213 to dilute reagent, if any, in the reservoir well, flush the reservoir well, and/or otherwise rinse or wash the reservoir well. In some embodiments, the vacuum source 237 can be activated and the wash pipette 213 can suck out most or substantially all of the reagent in the reservoir well 180. The reservoir well 180 can then be flooded with wash liquid that flows (indicated by arrows) in a controlled manner to the drain 183. The flooding process can remove most or substantially all of the volume of residual reagent within the reservoir well 180. After flushing the reservoir well 180, the vacuum source 237 can be activated again to clear the reservoir well. In other embodiments, prior to aspirating, the reservoir well can be flooded with wash liquid that flows (indicated by arrows) in a controlled manner to the drain 183. The flooding process can remove most or substantially all of the volume of reagent within the reservoir well. After flushing the reservoir well, the vacuum source 237 can be activated and the wash pipette 213 can suck out most or substantially all of the liquid (e.g., wash liquid, a mixture of wash liquid and reagent, etc.) left in the reservoir well 180. The pipette 213 can then be raised, and the drive mechanism 184 can rotate the carousel 177 to position another reservoir well at the wash position (e.g., underneath the wash pipette 213). The pipette cleaner 251 (FIG. 9A) can periodically clean the outside of pipette 213. In other embodiments, two or more pipettes can be used in the wash process. For example, one wash pipette can be used to dispense wash liquid and another wash pipette can suck residual liquid from the reservoir wells. In yet other embodiments, the reagent pipette assembly 175 can be used to perform wash cycles by rinsing out the reservoir wells 180.

The controller 144 of FIG. 9D can be configured to command the drive mechanism 184 to sequentially move each of the reservoir wells 180 to the washing position for washing by the wash pipette assembly 176. In some embodiments, the controller 144 stores instructions in memory 147 (illustrated in phantom line) and executes the instructions to command the pipette apparatus 172 to sequentially fill the reservoir wells 180 with reagent from the containers 211. Additionally or alternatively, memory 147 can store mixing instructions (e.g., a mixing program) that are executable by the controller 144 to command the wash pipette assembly 176 to deliver at least two reagents (e.g., two reagents, three reagents, etc.) to one of the reservoir wells. The mixing instructions can be selected based on information obtained from the slide to be processed. The controller 144 can be communicatively coupled to any or all of the components of the pipette apparatus 172.

The system 100 of FIGS. 1 and 2 can include one or more pipette apparatuses 172 discussed in connection with FIGS. 3-9D. The system 100 can have mixing stations 165 at opposite sides of the internal environment 121 (FIG. 2). The wash pipette assemblies can be stationary with vertically movable wash pipettes to avoid collisions between the wash pipettes and the reagent pipettes, which can be moved about the mixing stations. The mixing stations 165 can be serviced by a single reagent pipette assembly and a single wash pipette assembly. In other embodiments, each mixing station 165 is served by respective reagent pipette assemblies and wash pipette assemblies. The number of mixing stations, positions of the mixing stations, and sequence of operation of the reagent pipette assembly and wash pipette assembly can be selected based on the processes to be performed.

Figure 10:
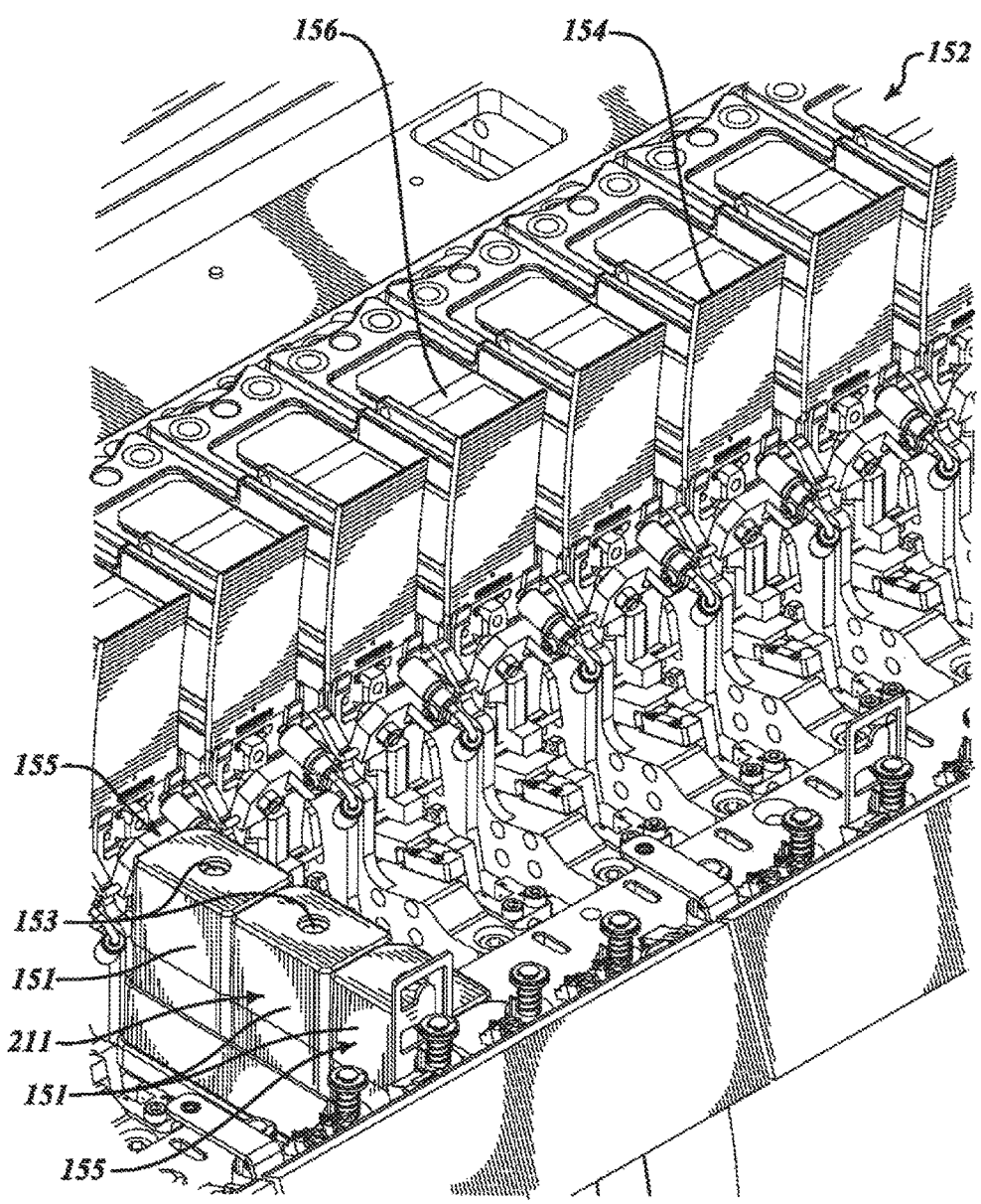
FIG. 10 is a detailed view of a portion of the specimen processing system of FIG. 2.

FIG. 10 is a detailed view of a section of the row 152. An opposable element 154 ("opposable 154") can move substance along a slide 156 to contact a specimen on the slide 156. In some embodiments, including the illustrated embodiment, 20 slides can be processed independently using a series of substances.

If a specimen is a biological sample embedded in paraffin, the sample can be deparaffinized using appropriate deparaffinizing fluid(s). After removing the deparaffinizing fluid(s), any number of substances can be successively applied to the specimen using the opposable 154. Fluids can also be applied for pretreatment (e.g., protein-crosslinking, exposing nucleic acids, etc.), denaturation, hybridization, washing (e.g., stringency washing), detection (e.g., linking a visual or marker molecule to a probe), amplifying (e.g., amplifying proteins, genes, etc.), counterstaining, or the like. In various embodiments, the substances include, without limitation, stains (e.g., hematoxylin solutions, eosin solutions, or the like), wetting agents, probes, antibodies (e.g., monoclonal antibodies, polyclonal antibodies, etc.), antigen recovering fluids (e.g., aqueous- or non-aqueous-based antigen retrieval solutions, antigen recovering buffers, etc.), solvents (e.g., alcohol, limonene, or the like), or the like. Stains include, without limitation, dyes, hematoxylin stains, eosin stains, conjugates of antibodies or nucleic acids with detectable labels such as haptens, enzymes or fluorescent moieties, or other types of substances for imparting color and/or for enhancing contrast. In some embodiments, the applied substance is a liquid reagent applied via dispensers, such as pipette dispensers 160, 162 depicted in FIG. 2 or reagent pipette assembly 175 depicted in FIGS. 3-9D.

A biological specimen can include one or more biological samples. Biological samples can be a tissue sample or samples (e.g., any collection of cells) removed from a subject. The tissue sample can be a collection of interconnected cells that perform a similar function within an organism. A biological sample can also be any solid or fluid sample obtained from, excreted by, or secreted by any living organism, including, without limitation, single-celled organisms, such as bacteria, yeast, protozoans, and amebas, multicellular organisms (such as plants or animals, including samples from a healthy or apparently healthy human subject or a human patient affected by a condition or disease to be diagnosed or investigated, such as cancer). In some embodiments, a biological sample is mountable on a microscope slide and includes, without limitation, a section of tissue, an organ, a tumor section, a smear, a frozen section, a cytology prep, or cell lines. An incisional biopsy, a core biopsy, an excisional biopsy, a needle aspiration biopsy, a core needle biopsy, a stereotactic biopsy, an open biopsy, or a surgical biopsy can be used to obtain the sample.

FIG. 10 shows a rack carrying a set of sealed containers 211 each holding about 10 mL to about 30 mL of reagent. The sealed containers 211 have caps 151 with seal elements in the form of septums 153 that can minimize, limit, or substantially prevent evaporation losses. The septums 153 can be broken (e.g., pierced, torn, etc.) to access the contents of the containers 211. When the user installs the containers 211, septums 153 can be broken to establish fluid communication with a pump or pipette (e.g., the reagent pipette 204 of FIGS. 9A-9D), which in turn delivers the fluid to an appropriate specimen processing station. The containers 211 can include, without limitation, one or more human readable labels, machine readable labels (e.g., a barcode to be read by the system 100), or other types of labels. The parking station 140, in some embodiments, provides fluids and solutions that are used in smaller volumes (e.g., dye solutions, such as hematoxylin and eosin solutions).

Figure 11:
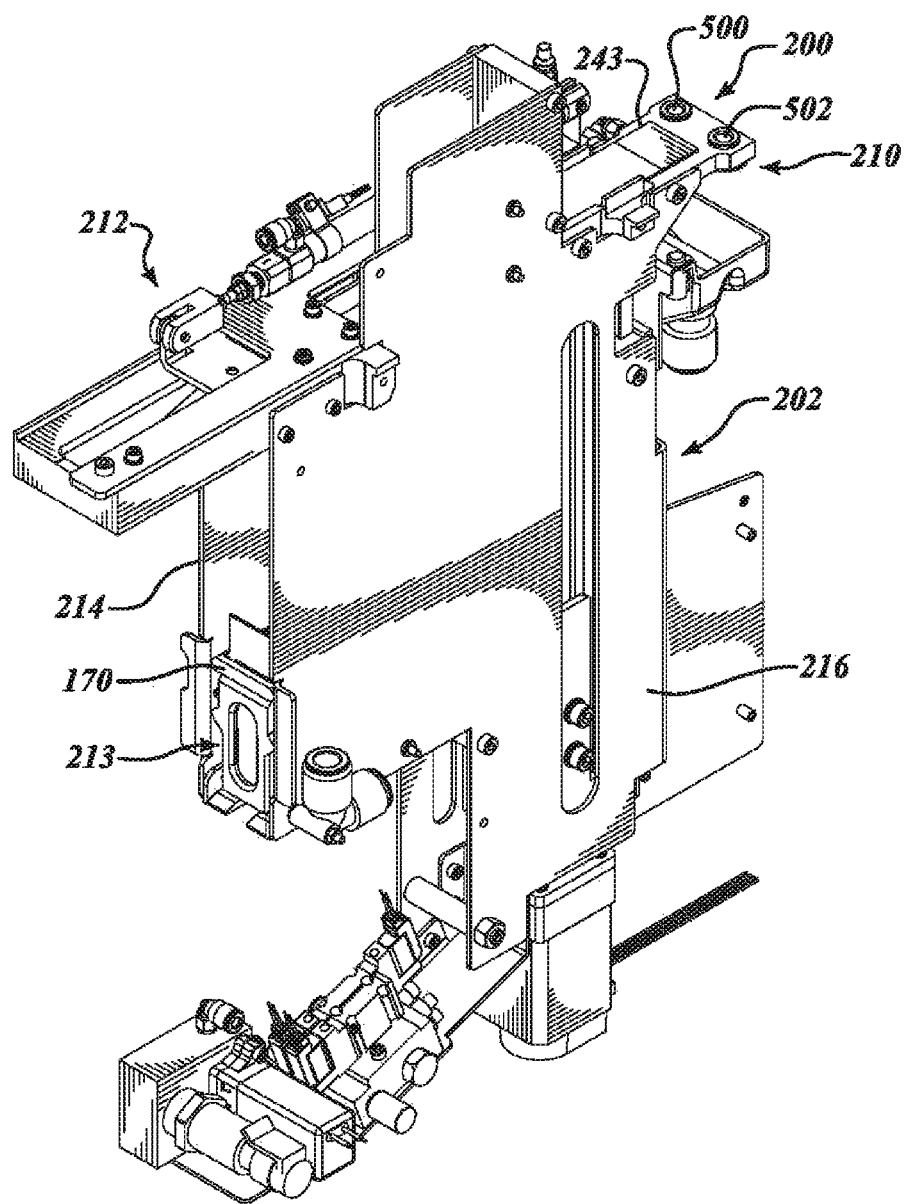
FIG. 11 is an isometric view of a slide ejector assembly in accordance with an embodiment of the disclosed technology.
Figure 12:
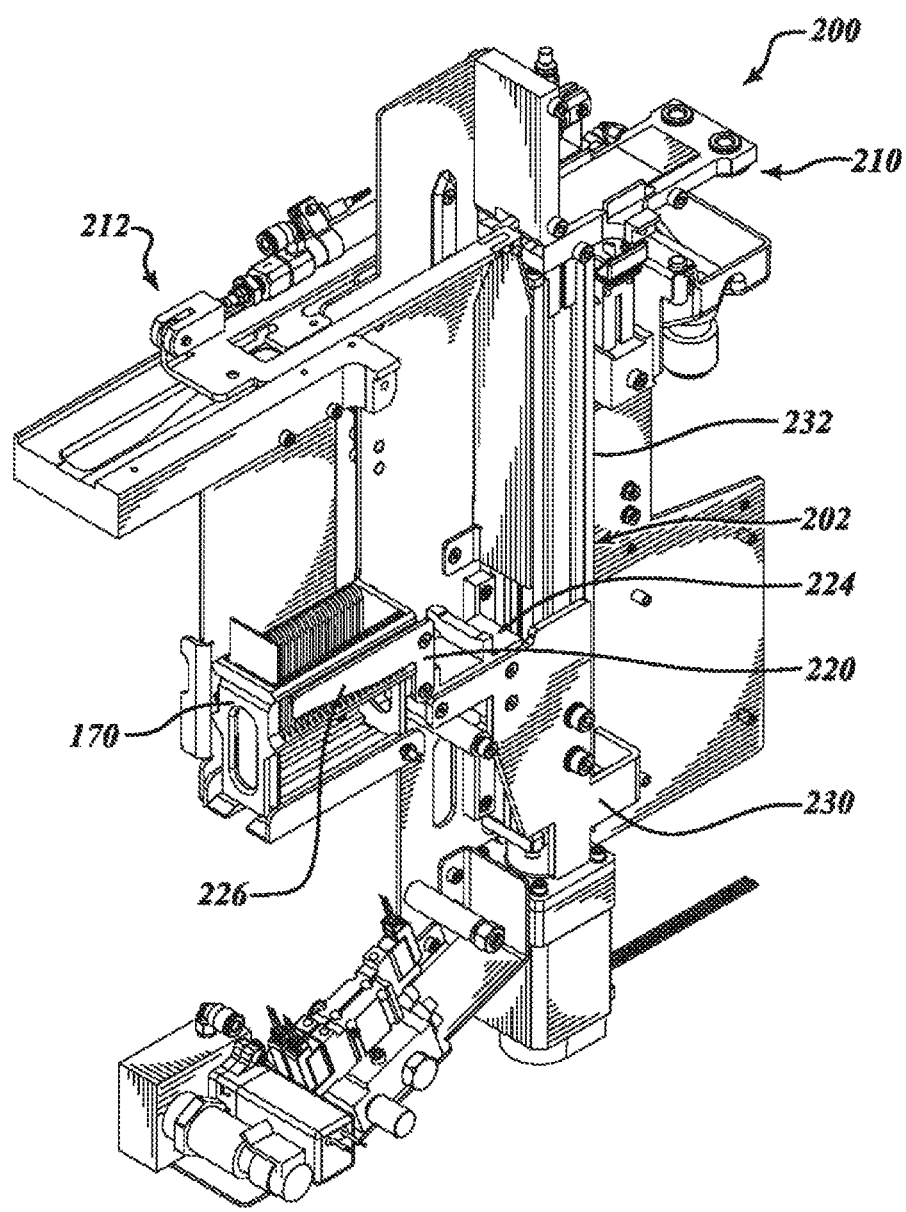
FIG. 12 is an isometric view of the slide ejector assembly of FIG. 11 with protective plates shown removed.

FIGS. 11 and 12 show a slide carrier 170 loaded into a slide ejector assembly 200 ("ejector assembly 200"). A plate 216 of FIG. 11 is shown removed in FIG. 12. The ejector assembly 200 includes a slide carrier handler 202 ("carrier handler 202"), a slide staging device 210 ("staging device 210"), and an ejector 212. The carrier handler 202 can include a carrier receiver 220 (FIG. 12) and a receiver rotator device 224 (FIG. 12). The carrier receiver 220 includes a pair of spaced apart arms 226 (e.g., elongate members, cantilevered members, etc.) upon which the slide carrier 170 can rest. The illustrated slide carrier 170 is a slide rack capable of holding microscope slides in a spaced-apart arrangement. One slide is shown in the carrier 170 of FIGS. 11 and 12. In some embodiments, the slide carrier 170 can be a basket, such as a SAKURA® basket or similar basket with shelves or dividers.

The carrier receiver 220 of FIG. 12 can include one or more grippers, clamps, retainers, or other components that releasably hold slide carriers. The receiver rotator device 224 can include, without limitation, one or more motors, actuation devices, or other components capable of rotating the arms 226. The arms 226 can move along an arcuate track, a pivoting mechanism, or the like to rotate the slide carrier 170. The carrier handler 202 can further include a carriage 230 and a rail 232. The carriage 230 can travel along the rail 232 to move the slide carrier 170 vertically.

Figure 13:
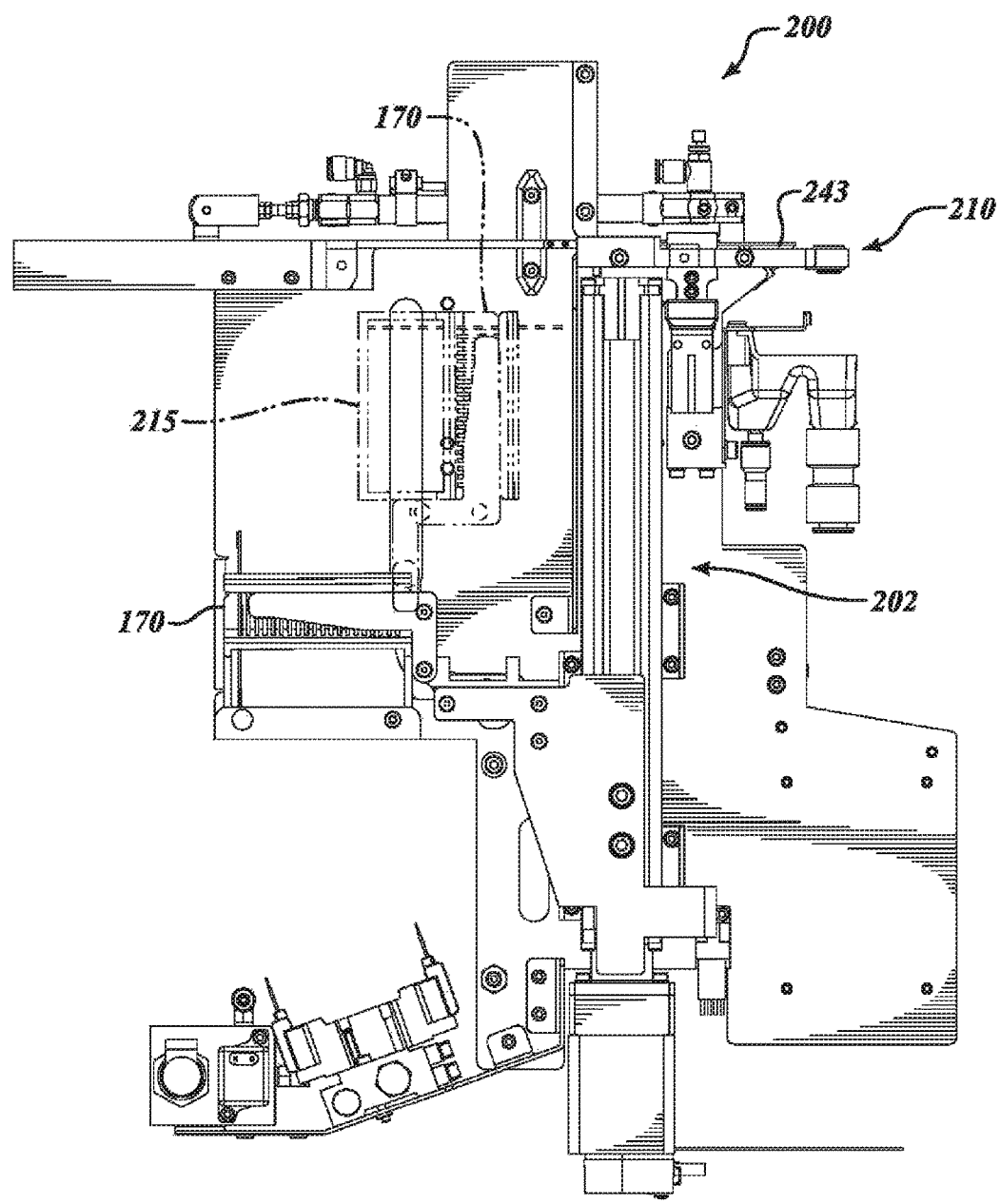
FIGS. 13 and 14 are side views of the slide ejector assembly of FIG. 11 with a slide carrier shown in different positions.
Figure 14:
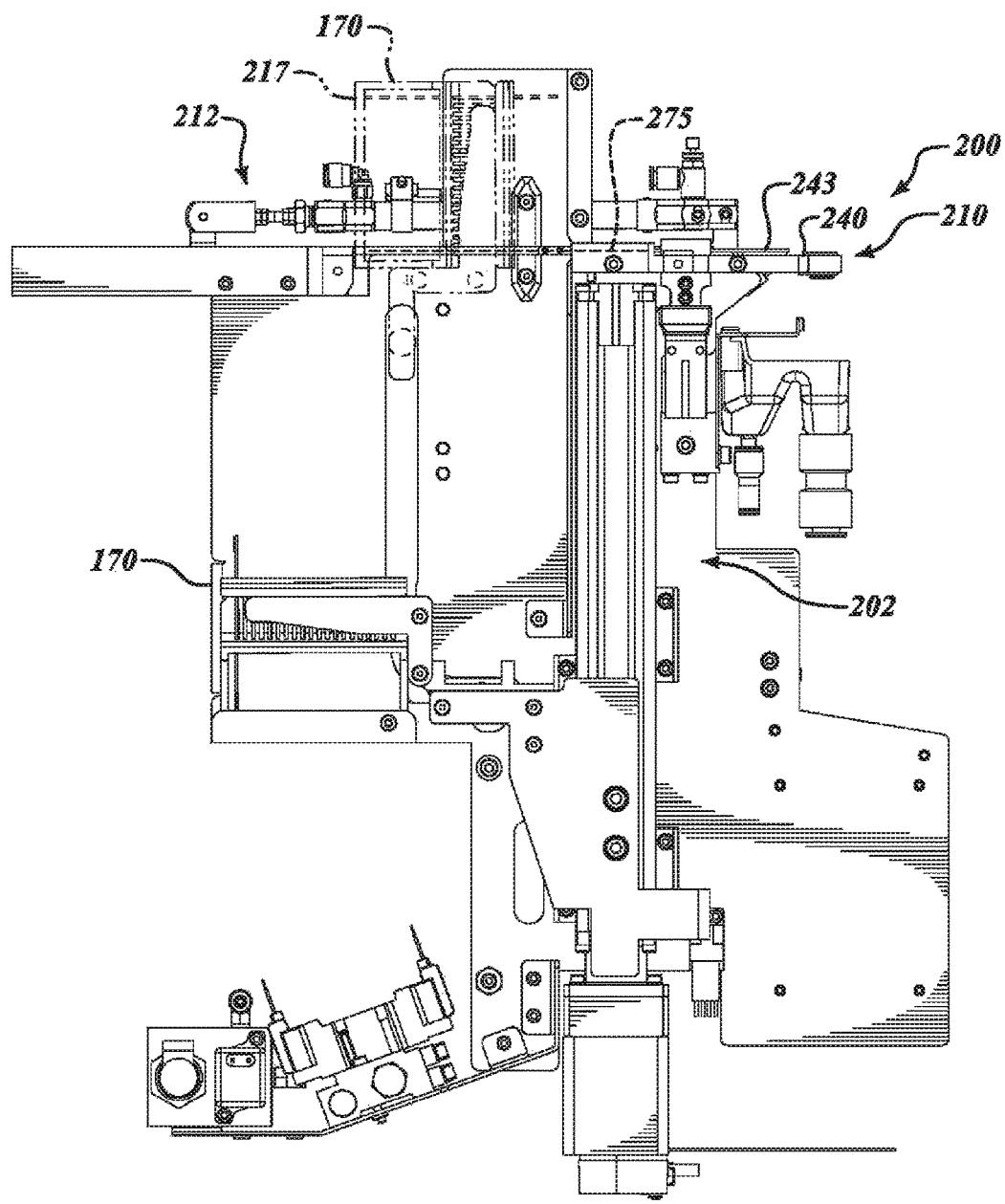

Referring again to FIG. 11, a fully or partially loaded slide carrier can be inserted between the plates 214, 216. The receiver rotator device 224 (FIG. 12) can rotate the carrier receiver 220 from a loading position 213 (FIG. 11) in which slides are held in a substantially vertical orientation to an intermediate position 215 (FIG. 13) in which slides are held in a substantially horizontal orientation. The term "substantially horizontal" generally refers to an angle within about +/−3 degrees of horizontal, for example, within about +/−1 degree of horizontal, such as within about +/−0.8 degrees of horizontal. The slide carrier 170 can be moved vertically to an unloading position 217 (FIG. 14). The ejector 212 can sequentially move the specimen-bearing slides to the staging device 210. The staging device 210 can position the specimen-bearing slide for subsequent transport, as discussed in connection with FIGS. 15-18.

Figure 15:
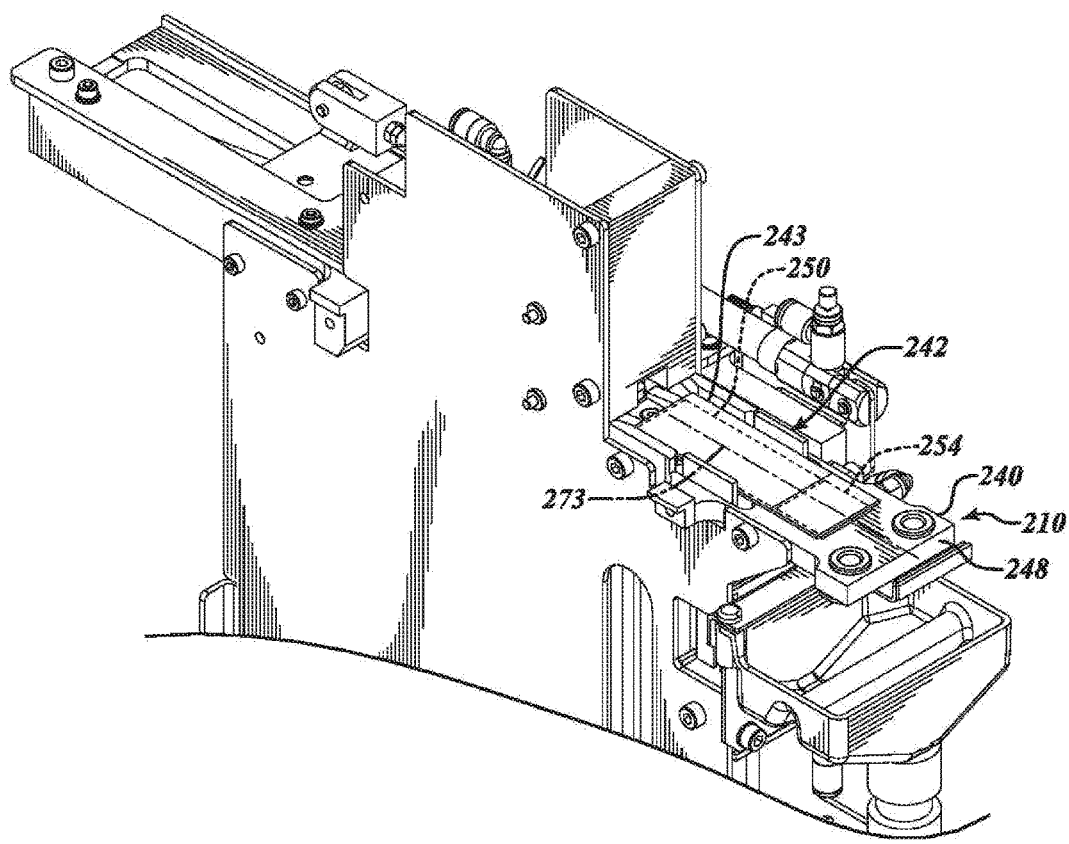
FIG. 15 is an isometric view of a slide staging device of a slide ejector assembly with a slide ready to be removed in accordance with an embodiment of the disclosed technology.
Figure 16:
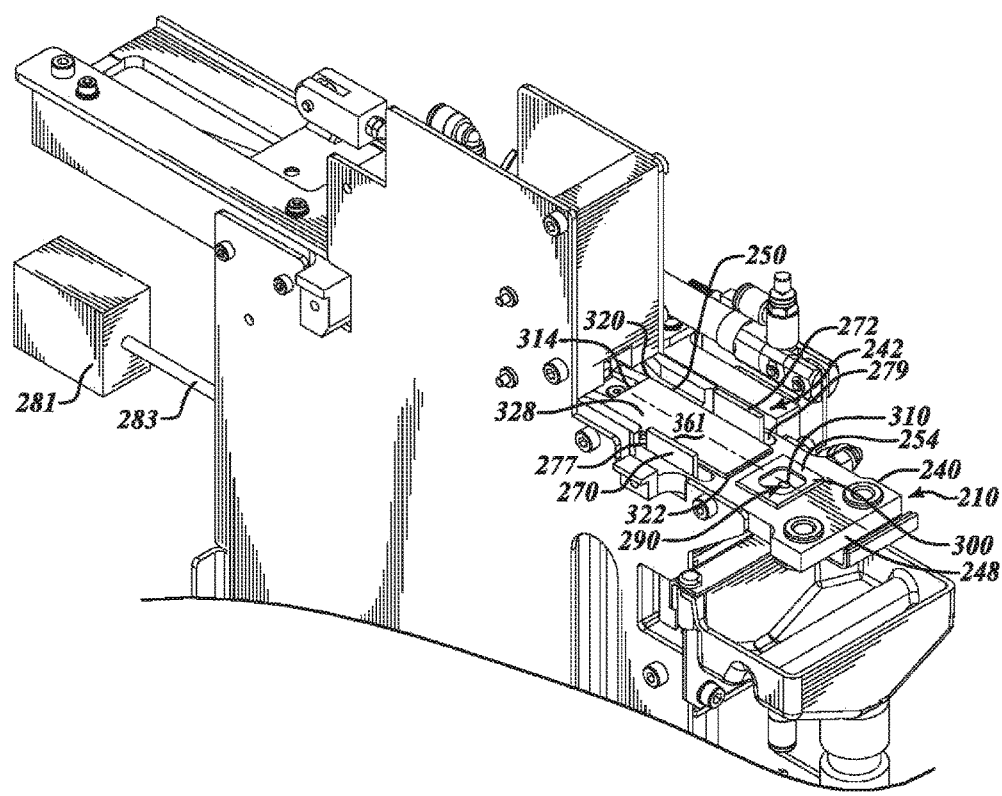
FIG. 16 is an isometric view of an empty slide staging device in accordance with an embodiment of the disclosed technology.

FIGS. 15 and 16 are isometric views of the staging device 210 including a standby platform 240 and an alignment device 242. The standby platform 240 can include a cantilevered plate 248, a slide holding region 250 ("holding region 250"), and an over-travel inhibitor 254. In FIG. 15, a slide 243 is resting on the holding region 250, which can be a raised region that is smaller than the slide 243. The slide 243 can protrude outwardly from the holding region 250 such that excess fluid, if any, can drain from the slide 243 onto the plate 248 without wicking underneath the slide 243 (e.g., between the slide 243 and a surface 361 of FIG. 16). In some embodiments, the standby platform 240 can include, without limitation, one or more sensors, readers, heaters, dryers, or other components that facilitate processing of the slides.

Referring to FIG. 16, the over-travel inhibitor 254 can accurately position a slide without physically contacting specimens on the slide, label edges, and/or other areas of the slide that may affect positioning accuracy. In some embodiments, the over-travel inhibitor 254 can position a slide without contacting the top of the slide at locations, for example, near overhanging labels, which can effect positioning accuracy. The over-travel inhibitor 254 includes a vacuum port 290 and a vacuum source 281 fluidically coupled to the vacuum port 290 via one or more fluid lines 283 (e.g., internal fluid lines, external fluid lines, etc.). The vacuum source 281 can include, without limitation, one or more pressurization devices, pumps, or other types of devices capable of drawing a vacuum via an opening 310. A bottom surface of the slide 243 (FIG. 15) and a contact surface 300 of the vacuum port 290 can form a seal to maintain the vacuum. In some embodiments, the contact surface 300 can comprise one or more compressible materials (e.g., rubber, silicon, or the like) capable of maintaining an airtight seal. In other embodiments, the contact surface 300 can comprise one or more non-compressible materials (e.g., aluminum, stainless steel, etc.) and, in some embodiments, may include one or more sealing members (e.g., O-rings, gaskets, sealing cups, etc.) used to form a seal with the slide 243. In further embodiments, the contact surface 300 and/or the vacuum port 290 can include a pressure sensor or other sensor for detecting the presence of a slide 243 on the standby platform 240.

The holding region 250 includes ends 320, 322 and a main body 328 extending between the ends 320, 322. An ejector stop 314 is defined by the end 320 and can be used to reference the position of an end of the slide 243. The ejector stop 314 can be a sidewall or edge of the end 320. In other embodiments, the ejector stop can be one or more protrusions.

Figure 17:
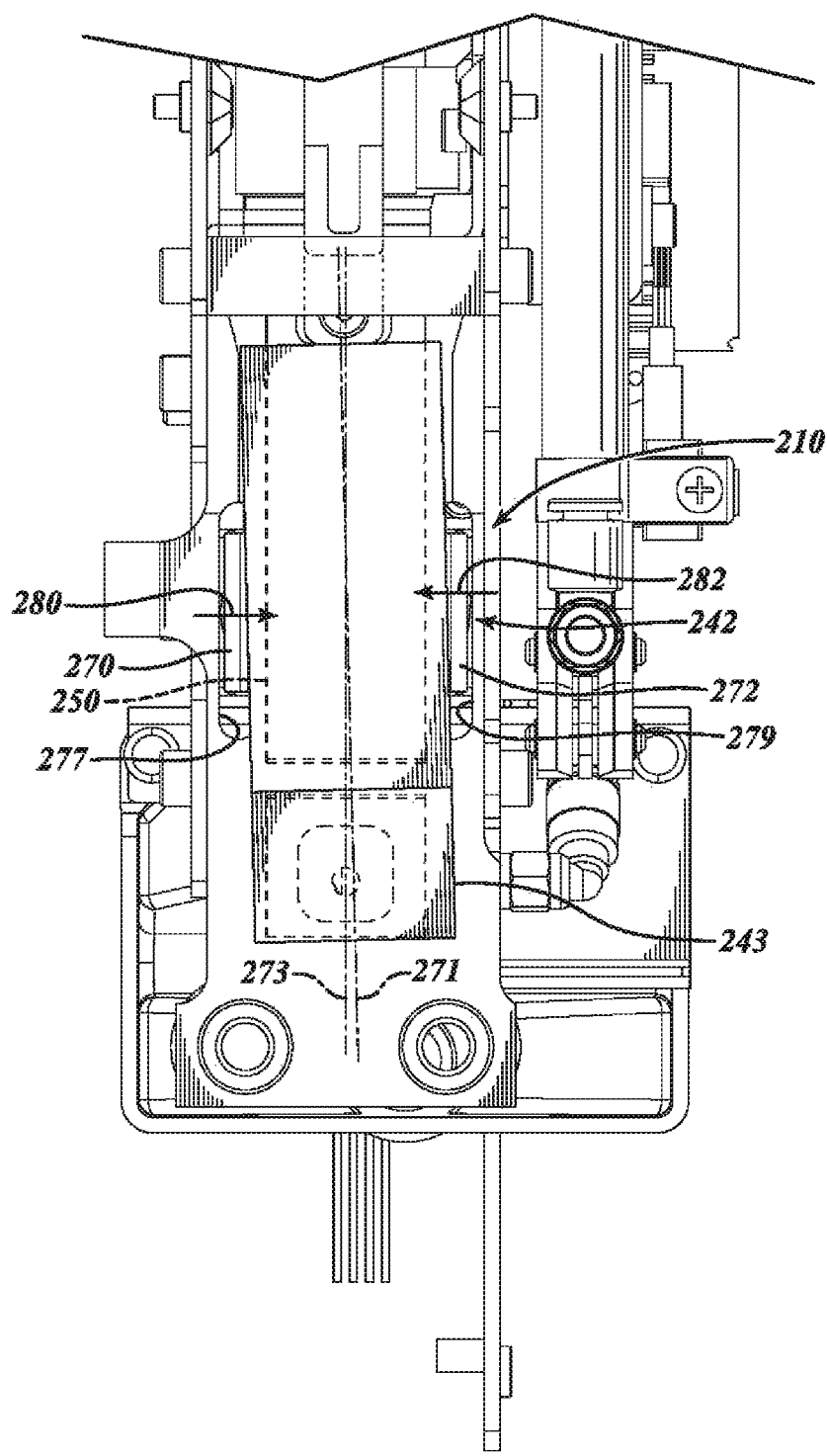
FIGS. 17 and 18 are top plan views of a slide staging device with an alignment device in accordance with an embodiment of the disclosed technology.
Figure 18:
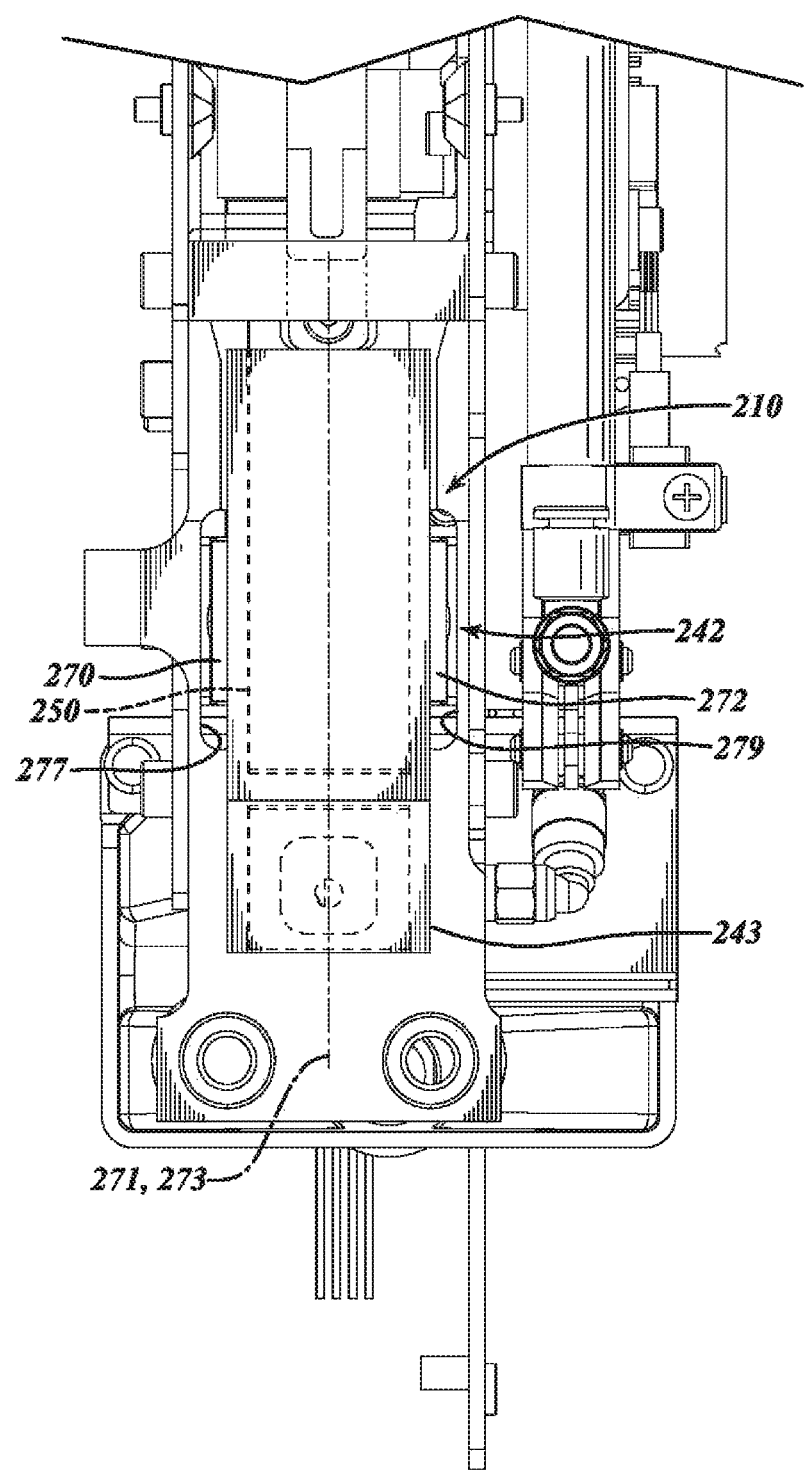

As shown in the embodiment illustrated in FIGS. 16-18, the staging device 210 includes the alignment device 242. In one embodiment, the alignment device 242 includes a pair of generally parallel jaws 270, 272 that protrude upwardly through openings 277, 279, respectively, and vertically past the holding region 250. The alignment device 242 can include, without limitation, one or more actuators (e.g., pneumatic actuators, electromechanical actuators, etc.) capable of moving the jaws 270, 272. The alignment device 242 can align the slide to facilitate slide pickup and handling because a transfer head may be unable to properly pick up and handle a misaligned slide. In some embodiments, a label of the slide can be spaced apart from the jaws 270, 272 to prevent unwanted adherence of the slide to the jaws 270, 272.

FIG. 17 shows a longitudinal axis 271 of the slide 243 in a misaligned position. The longitudinal axis 271 is not parallel to a longitudinal axis 273 of the holding region 250. The jaws 270, 272 can move from an open position (FIG. 17) toward one another (indicated by arrows 280, 282) to a closed position (FIG. 18) so as to reposition the slide 243. In some embodiments, the longitudinal axis 271 of the slide 243 in an aligned position can be substantially aligned (e.g., parallel) with the longitudinal axis 273 of the holding region 250. After aligning the slide 243, the jaws 270, 272 can be returned to the open position and the slide 243, now aligned, can be picked up. The configuration and operation of the alignment device 242 can be selected based on the desired position of the aligned slide. Additionally, the alignment device 242 can be used to align slides having different dimensions because the jaws 270, 272 apply the same force to opposing sides of the slide.

Figure 19:
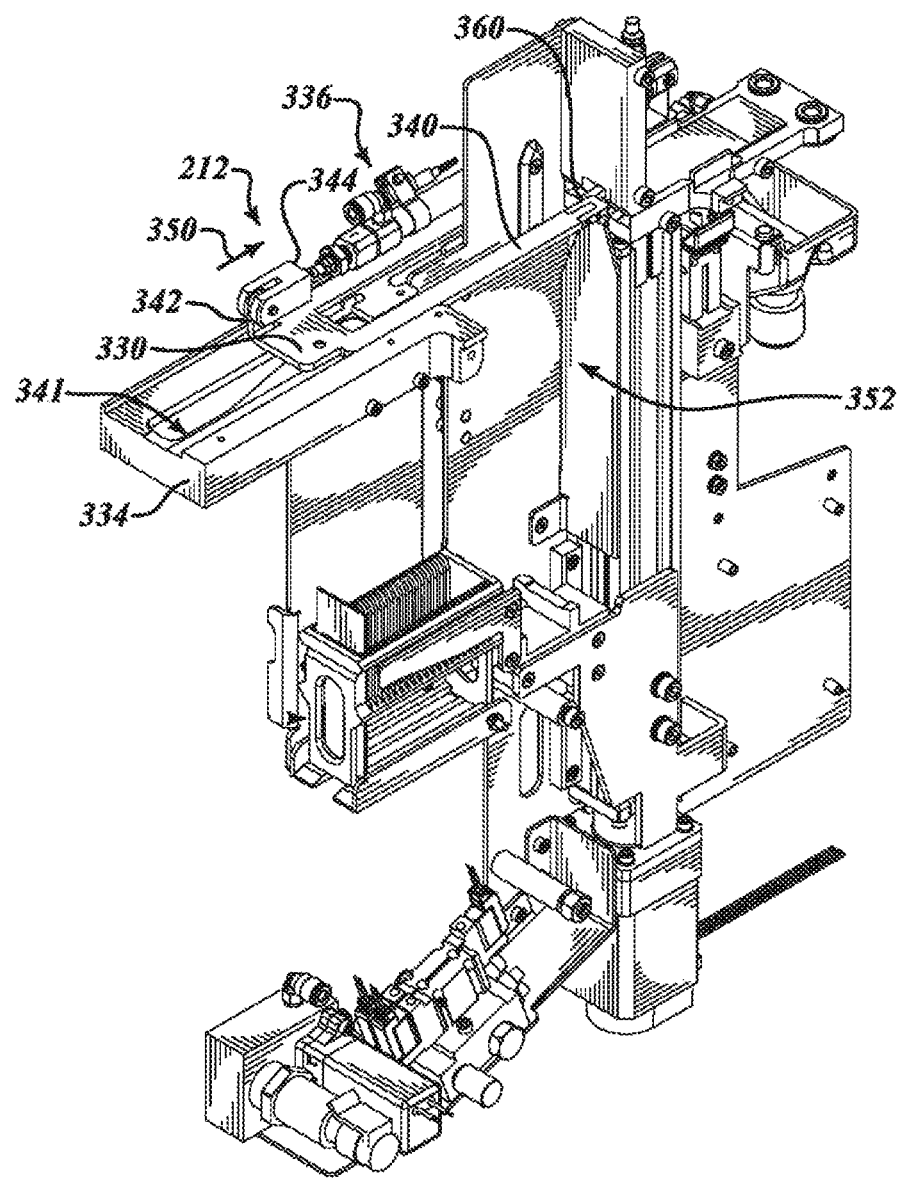
FIGS. 19 and 20 are isometric views of a slide ejector assembly with a protective plate shown removed.
Figure 20:
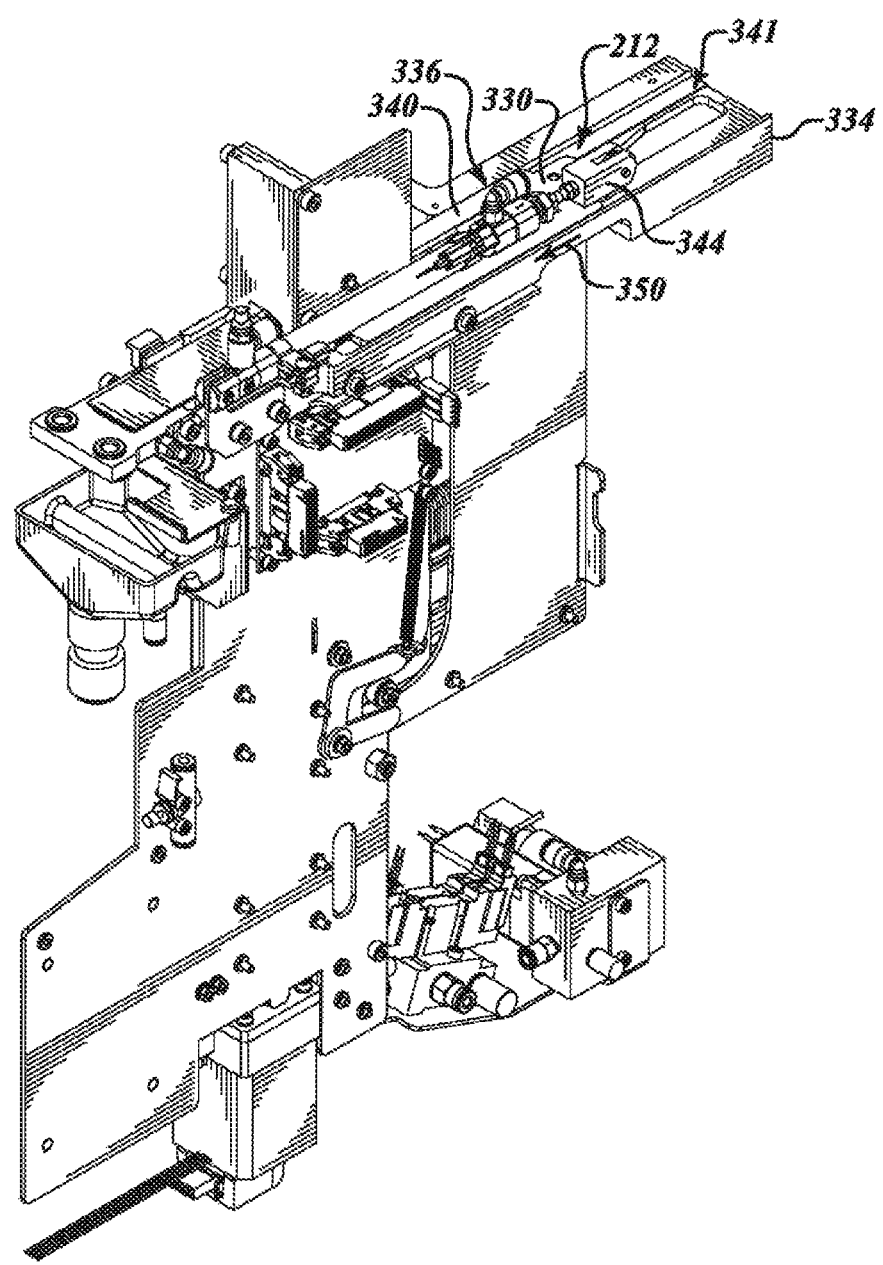
Figure 21:
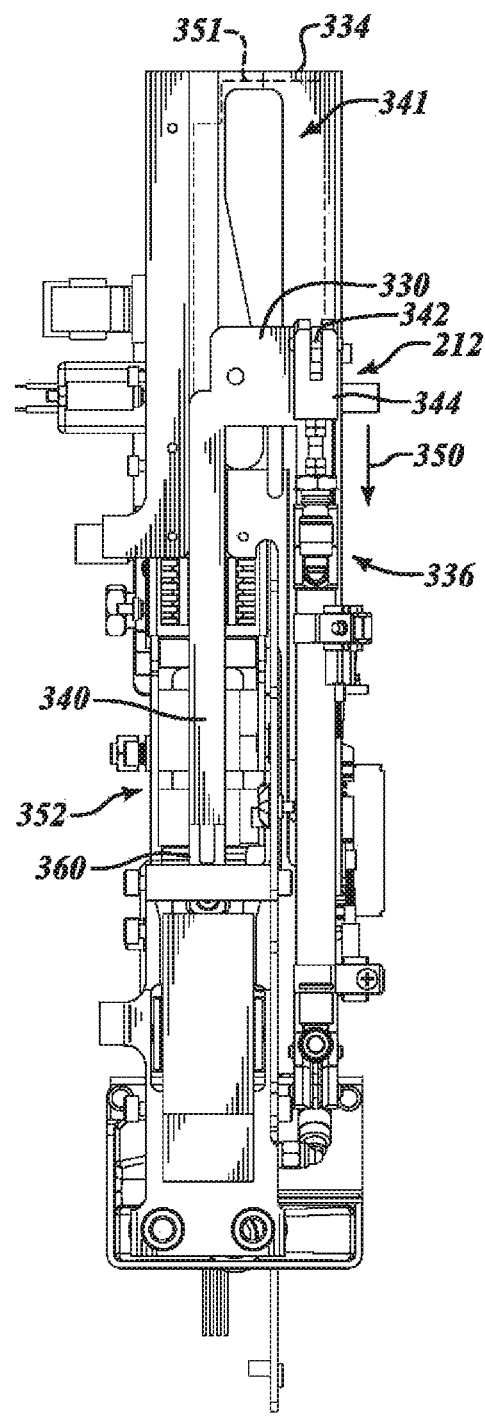
FIG. 21 is a top plan view of the slide ejector assembly of FIGS. 19 and 20.

FIGS. 19-21 show the ejector 212, which includes an ejector element 330, a base 334, and a drive mechanism 336. The ejector element 330 includes an elongate portion 340 positioned in a recess 341 in the base 334 and a mounting portion 342 coupled to a rod 344 of the drive mechanism 336. The drive mechanism 336 can provide reciprocating linear motion and can comprise, without limitation, one or more stopper motors, pistons (e.g., pneumatic pistons, hydraulic pistons, etc.), pressurization devices (e.g., pumps, air compressors, etc.), sensors, or the like. The illustrated rod 344 has been moved in the direction indicated by arrow 350 to move the ejector element 330 from a first or initial position 351 (illustrated in phantom line in FIG. 21) across a slide carrier receiving gap 352 ("gap 352") such that a head 360 of the elongate portion 340 pushes a slide onto the standby platform 240. The head 360 can comprise a compliant material (e.g., rubber, plastic, etc.) to avoid damaging the slides. In some embodiments, the head 360 can push the slide along the surface 361 (FIG. 16) of the holding region 250 until the slide is at the desired location. Slides can be removed from the slide carrier 170 one at a time until the slide carrier 170 is empty.

Referring again to FIGS. 1 and 2, a user can load a slide carrier holding specimen-bearing slides into the parking station 124. A transfer mechanism can transport the slide carrier to the ejector assembly 200. The transfer mechanism can include, without limitation, one or more robotic handlers or arms, X-Y-Z transport systems, conveyors, or other automated mechanisms capable of carrying items between locations. In some embodiments, the transfer mechanism includes one or more end effectors, grippers, suction devices, holders, clamps, or other components suitable for gripping the slide carrier.

The ejector assembly 200 moves the slide carrier 170 to the unloading position 217 (FIG. 14). The slide carrier 170 is moved vertically to index slides relative to a reference position. The reference position can be a plane (e.g., a fixed slide removal plane 275 shown in FIG. 14) defining a slide removal position. A bottom of the slide to be removed can be generally coplanar or slightly above the surface 361 (FIG. 16). The drive mechanism 336 can move the ejector element 330 horizontally to move the elongate portion 340 (FIG. 19) through the carrier 170 to push the slide onto the surface 361 (FIG. 15). A vacuum can be drawn by the slide over-travel inhibitor 254 to inhibit movement of the slide 243 as the head 360 contacts the ejector stop 314 (FIG. 16). The head 360 can then be moved away from the slide 243. The jaws 270, 272 can be moved from the open position to the closed position to align the slide 243. The aligned slide 243 can be retrieved and transported to a specimen processing station. The drive mechanism 336 can move the ejector element 330 back and forth and the slides can be indexed to sequentially deliver all of the slides to the staging device 210.

To protect the specimens, the lowermost slide in the slide carrier 170 can be ejected first. By starting with the lowermost slide, the specimen(s) on the vertically adjacent slide can be facing away from the head 360 and therefore protected. If the head 360 is vertically misaligned with the slide to be removed, the head 360 may strike the bottom of the vertically adjacent slide without dislodging the specimen(s) on the upper surface of the vertically adjacent slide. After removing the lowermost slide, the lowermost slide left in the slide carrier 170 can be removed. This process can be repeated until the slide carrier 170 is empty. Other indexing sequences can be used to remove the slides.

The empty slide carrier 170 can be returned to the loading position (FIG. 11) and then transported to one of the bays of the parking station 124. The empty slide carrier 170 can be removed from the parking station 124 and filled with specimen-bearing slides and returned to the parking station 124. Alternatively, the empty slide carrier 170 can be filled with processed specimen-bearing slides using the ejector assembly 200. A pusher assembly can be used to push processed specimen-bearing slides on the staging device 210 into a slide carrier. Thus, the ejector assembly 200 can be used to both unload and load slide carriers.

Figure 22:
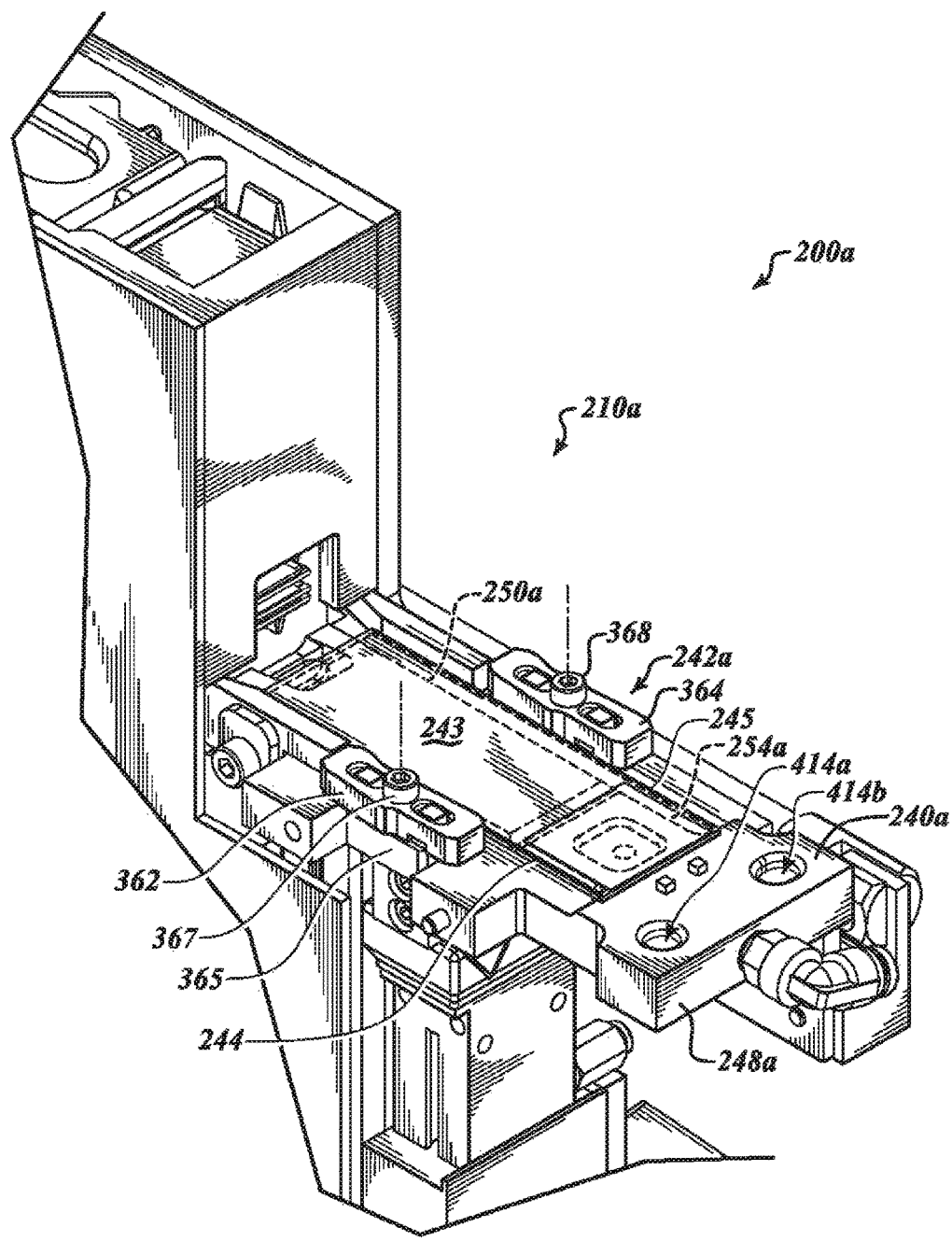
FIG. 22 is an isometric view of a slide staging device of a slide ejector assembly with a slide ready to be removed in accordance with another embodiment of the disclosed technology.
Figure 23:
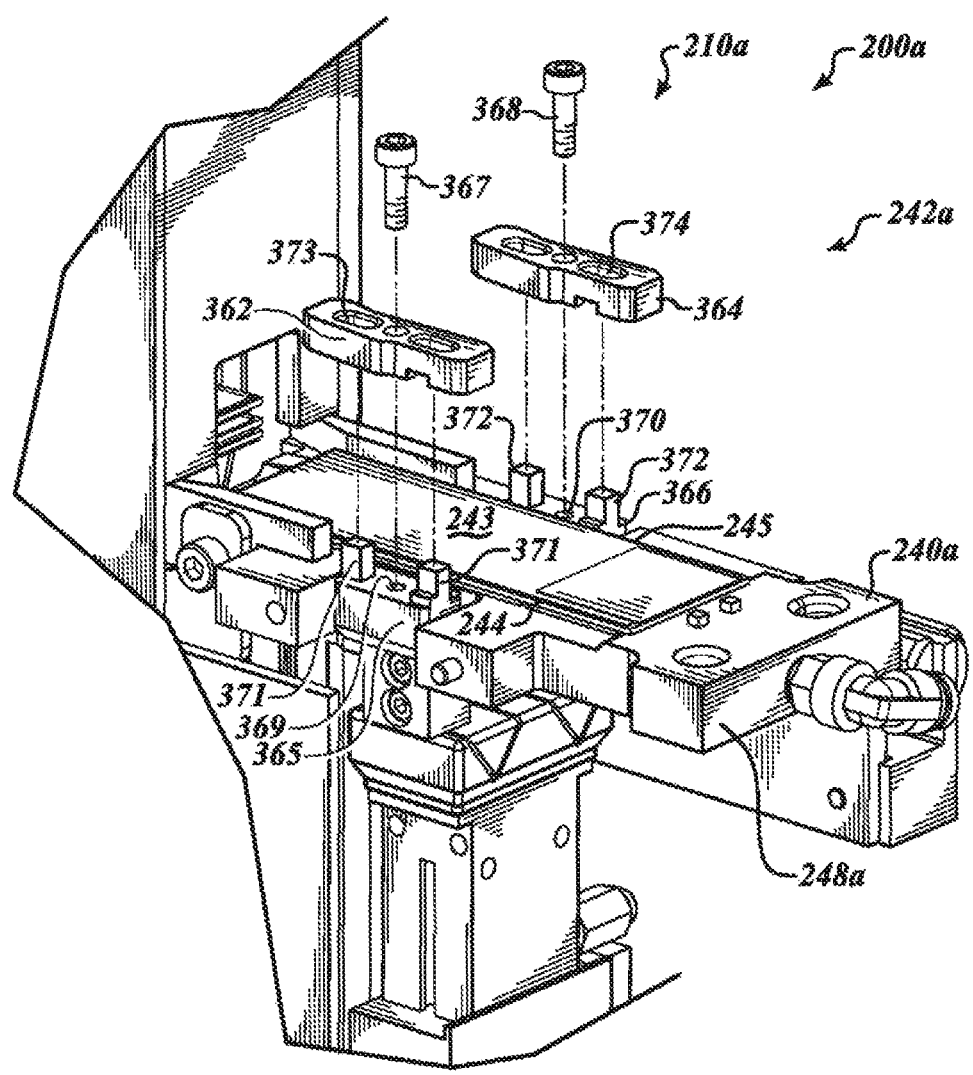
FIG. 23 is an isometric view of the slide staging device of FIG. 22 illustrating components of an alignment device in accordance with an embodiment of the disclosed technology.

FIGS. 22-26 illustrate a staging device 210a of a slide ejector assembly 200a configured in accordance with an additional embodiment of the present technology. FIGS. 22 and 23 are isometric views of the staging device 210a that includes features generally similar to the features of the staging device 210 described above with reference to FIGS. 16-18. For example, the staging device 210a includes a standby platform 240a (similar to standby platform 240 shown in FIG. 16) having a cantilevered plate 248a, a slide holding region 250a ("holding region 250a"), and an over-travel inhibitor 254a (similar to over-travel inhibitor 254 shown in FIG. 16). The staging device 210a also includes an alignment device 242a configured to move the slide 243 from a misaligned position on the standby platform 240a to an aligned position. However, in the embodiment shown in FIGS. 22 and 23, the alignment device 242a does not include a pair of generally parallel jaws 270, 272 (FIG. 16) that protrude upwardly through openings 277, 279 (FIG. 16) in the standby platform 240a.

In the embodiment illustrated in FIG. 22, the alignment device 242a includes a first aligning member 362 for engaging a first edge 244 of the slide 243 and a second aligning member 364 positioned opposite the first aligning member 362 for engaging a second edge 245 of the slide 243. Engagement of the first and second sides 244, 245 of the slide 243 can pivot or otherwise move the slide 243 from an unaligned orientation on the slide holding region 250a to an aligned orientation on the holding region 250a to facilitate slide pickup and handling by a transfer apparatus (not shown).

Referring to FIG. 23, the first and second aligning members 362, 364 are secured to blocks 365, 366 by first and second fasteners 367, 368 (e.g., pins, bolts, screws or other mechanical fasteners known to those in the art). For example, the blocks 365, 366 can include holes 369, 370 for receiving the fasteners 367, 368, respectively. The blocks 365, 366 can further include one or more protrusions 371, 372 for allowing rotation or pivoting of the aligning members 362, 364 and for engaging the first and second aligning members 362, 364, respectively, to limit rotation or pivoting of the aligning members 362, 364 with respect to the blocks 365, 366 and/or during engagement with the slide 243 (described below). Openings 373, 374 (one identified) can be disposed in the aligning members 362, 364 for receiving the protrusions 371, 372. In other embodiments, protrusions may be provided on the aligning members 362, 364 that are receivable in openings provided in the blocks 365, 366. In some embodiments, the protrusions 371, 372 may be non-circular having a rectangular or other geometrical shape. The openings 373, 374 can be shaped to accommodate the corresponding geometrical shape of the protrusions 371, 372, or as illustrated in FIG. 23, the openings 373, 374 can be through-holes that receive the protrusions 371, 372.

Figure 24A:
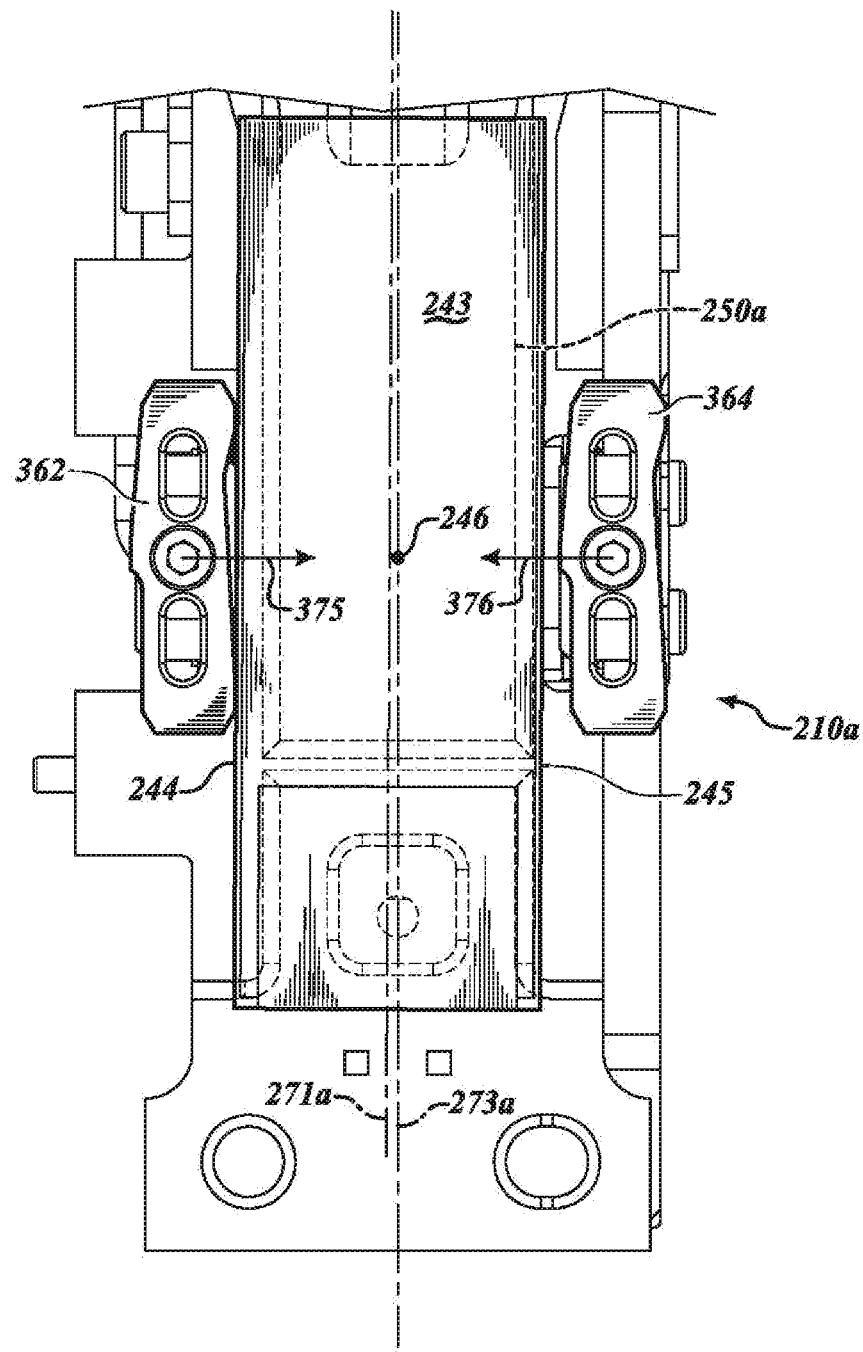
FIGS. 24A and 24B are top plan views of a slide staging device with an alignment device in accordance with an embodiment of the disclosed technology.
Figure 24B:
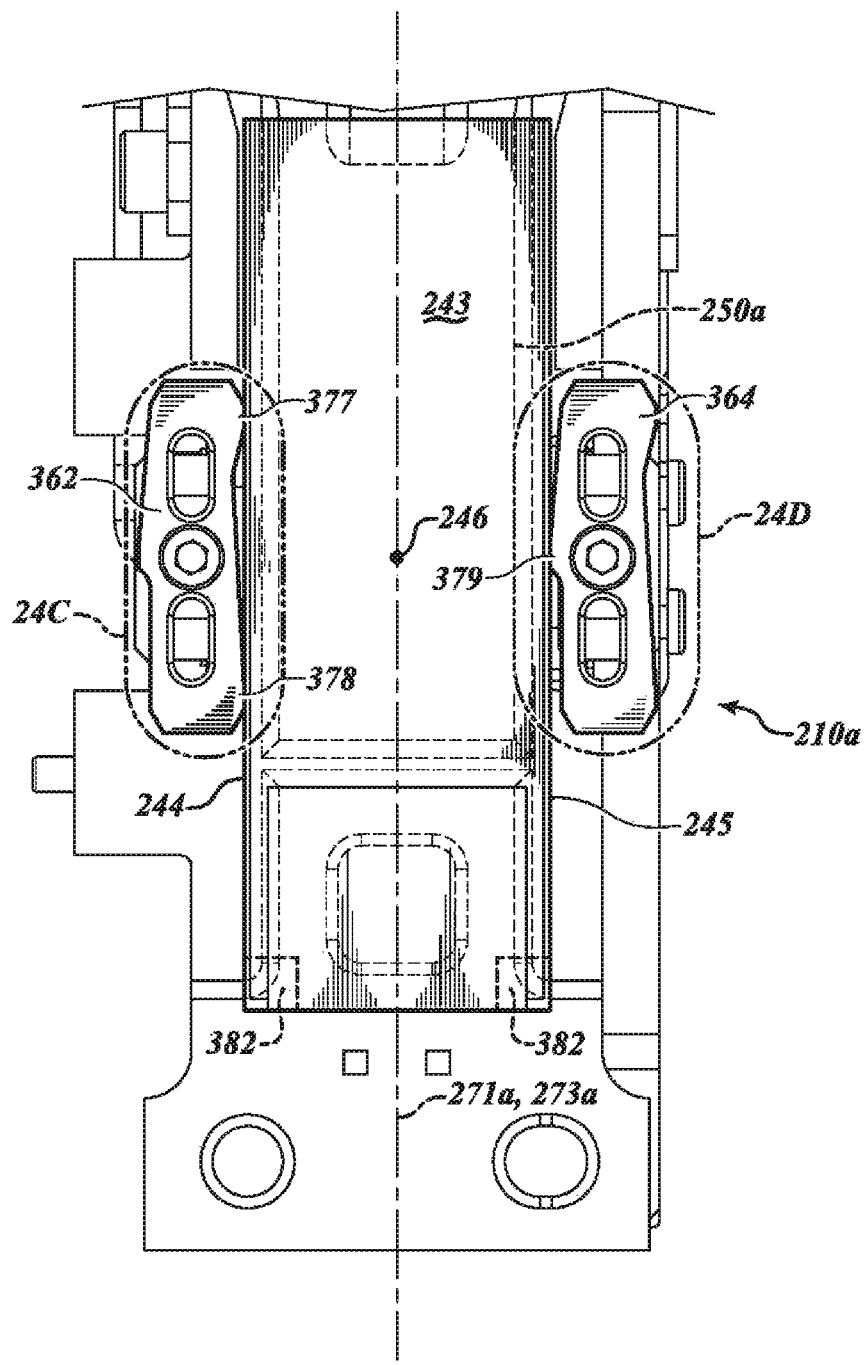
Figure 24C:
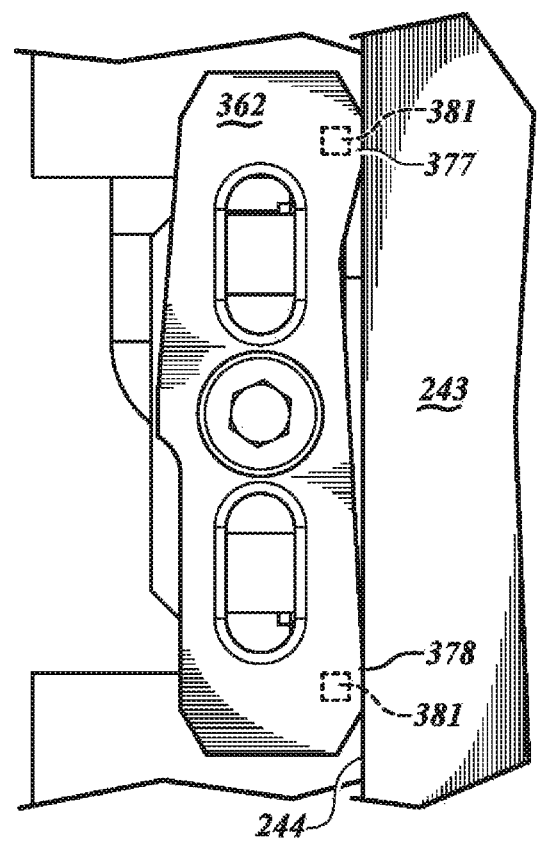
FIGS. 24C and 24D are enlarged views of the alignment device of FIG. 24B.

The alignment device 242a can include, without limitation, one or more actuators (e.g., pneumatic actuators, electromechanical actuators, etc.) capable of moving the blocks 365, 366 having the aligning members 362, 364 secured thereto toward and away from a longitudinal axis 273a of the holding region 250a (shown in FIGS. 24A and 24B). For example, FIGS. 24A and 24B are enlarged top views of the staging device 210a illustrating stages in a process for aligning a longitudinal axis 271a of the slide 243 with the longitudinal axis of 273a of the holding region 250a. FIG. 24A shows the longitudinal axis 271a of the slide 243 in a misaligned position. The longitudinal axis 271a is not parallel to the longitudinal axis 273a of the holding region 250a. The first and second aligning members 362, 364 can move from an open position (FIG. 24A) toward one another (indicated by arrows 375, 376) to a closed position (FIG. 24B) where the aligning members 362, 364 engage or come in contact with the first and second sides 244, 245 of the slide 243 to reposition the slide.

Figure 24D:
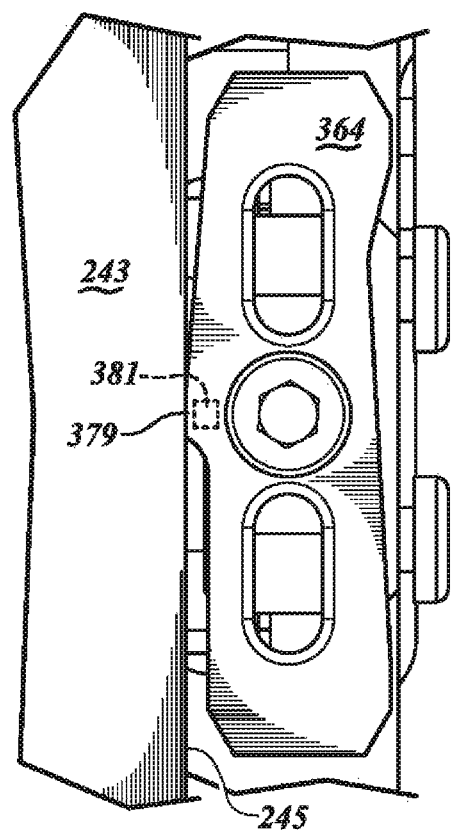

In one embodiment, the first and second aligning members 362, 364 together contact the slide 243 at three separate points of contact. In the embodiment illustrated in FIGS. 24B and 24C, the first aligning member 362 has a first contact region 377 and a second contact region 378 configured to engage the first edge 244 of the slide 243. As illustrated in FIGS. 24B and 24D, the second aligning member 364 has a third contact region 379 configured to engage the second edge 245 of the slide 243. In one embodiment, the area of the point of contact is the portion of the slide 243 engaged by the first, second and third contact regions 377, 378, 379. In some arrangements, the points of contact are relatively small, discrete portions of the slide 243 (e.g., along the first and second edges 244, 245). In some embodiments, the surface areas defined by the three points of contact and engaged by the first, second and third contact regions 377, 378, 379 are approximately the same; however, in other embodiments, the surface areas can vary. In one embodiment, the third contact region 379 is configured to contact the second edge 245 of the slide 243 in a lateral position along the slide 243 that is between the lateral positions contacted by the first contact region 377 and second contact region 378 on the first edge 244 of the slide 243.

Referring to FIG. 24B, when the first and second contact regions 377, 378 of the first aligning member 362 and the third contact region 379 of the second aligning member 364 engage the first and second sides 244, 245 of the slide 243, respectively, the slide 243 can move (e.g., pivot about a midpoint or axis of rotation 246 created or defined by the three separate contact points) to an aligned position. Movement of the first and second alignment members 362, 364 via blocks 365, 366 can continue until the slide 243 is engaged by the first, second and third contact regions 377, 378 and 379 and the slide 243 no longer moves (e.g., comes to rest on the holding region 250a in an aligned position). In some embodiments, the first and second aligning members 362, 364 may include one or more pressure sensors 381 (FIGS. 24C and 24D) on or adjacent to one or more contact regions 377, 378, 379 to ensure that the aligning members 362, 364 are applying a sufficient amount of force to move the slide 243 and/or are not compressing the slide 243 in a manner that could break or compromise the slide. In some embodiments, the contact regions 377, 378, 379 may include a coating and/or a compliant material (e.g., rubber, plastic, etc.) to avoid damaging the slides.

While FIGS. 24A-24D show the first aligning member 362 having the first contact region 377 and the second contact region 378 and the second aligning member 364 having the third contact region 379, or other arrangements can be used. For example, the second aligning member 364 can include two contact regions and the first aligning member 362 may include one contact region. Further, while the aligning members 362, 364 are illustrated as having an irregular shaped geometry for providing first, second and third contact regions 377, 378, 379. other geometries may be suitable for providing first, second and third contact regions. In other embodiments, the aligning members 362, 364 may provide more than three separate (e.g., discrete) contact regions for engaging the slide 243.

Referring back to FIG. 24B, the longitudinal axis 271a of the slide 243 in an aligned position can be substantially aligned (e.g., parallel) with the longitudinal axis 273a of the holding region 250a. After aligning the slide 243, the aligning members 362, 364 can disengage the slide 243 and be returned to the open position by moving the blocks 365, 366 in a direction opposite to the direction of the arrows 375, 376 (FIG. 24A). Optionally, the staging device 210a may include sensors 382 or other signaling device for determining the presence of the slide 243 on the standby platform 240a and/or determining when the longitudinal axis 271a is substantially aligned with the longitudinal axis 273a (FIG. 24B). For example, the standby platform 240a and/or the holding region 250a may include position sensors, pressure sensors, light sensors and the like for determining the relative position of the slide 243 with respect to the holding region 250a. Similar to the configuration and operation of the alignment device 242 (FIGS. 16-18), the alignment device 242a can be configured to align slides having different dimensions and align them to a desired position on the standby platform 240a.

Figure 25:
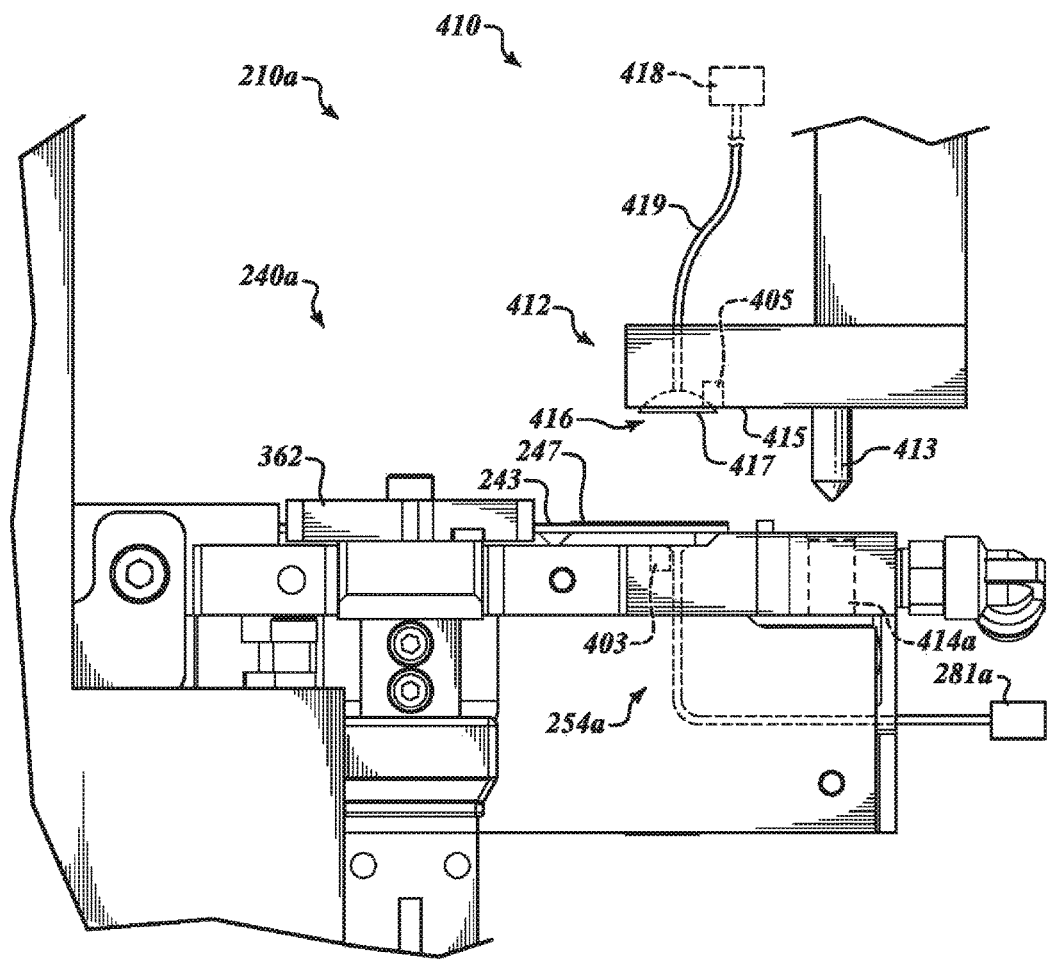
FIGS. 25 and 26 are side views of a slide staging device and a transfer assembly in accordance with an embodiment of the disclosed technology.
Figure 26:
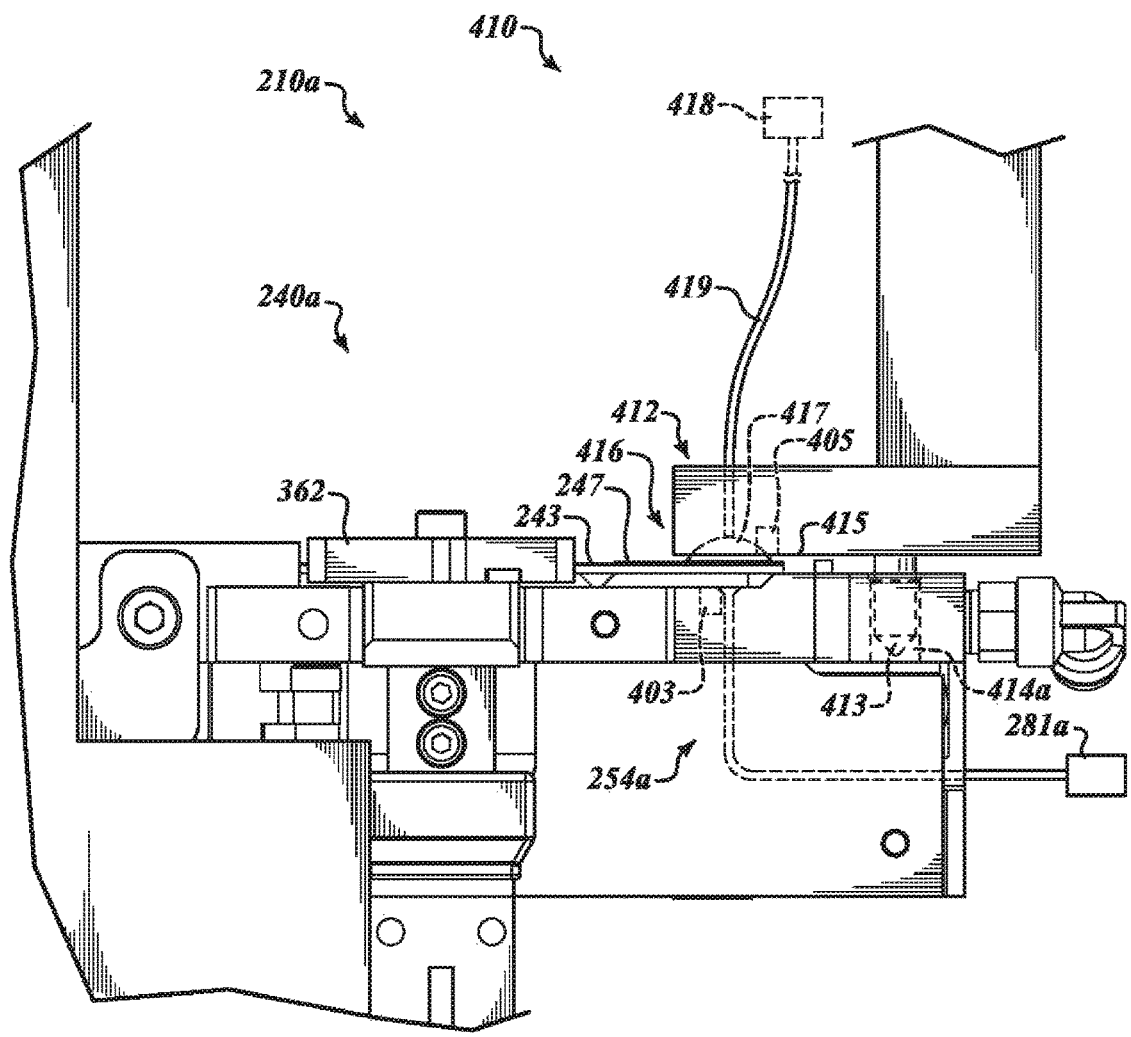

After aligning the slide 243, the slide can be retrieved and transported to a specimen processing station (not shown). FIGS. 25 and 26 illustrate a portion of a transport assembly 410 having a slide transfer head 412 ("transfer head 412") configured to pick up the aligned slide 243 from the standby platform 240a while maintaining the proper alignment. Referring to FIG. 25, the transfer head 412 includes a plurality of head alignment features 413 (e.g., 2 head alignment features) on a lower surface 415 of the transfer head 412. Head alignment features 413 can include, without limitation, pins (e.g., elongate rods), protrusions, openings (e.g., openings defined by bushings, openings in plates, etc.), or the like. In some embodiments, the head alignment features 413 can be in the form of alignment pins (e.g., first and second alignment pins) that can be inserted into corresponding alignment features 414 (shown individually as 414a and 414b) on the staging device 210a (e.g., on cantilevered plate 248a), illustrated in FIGS. 22 and 25. In other embodiments, the head alignment features 413 are openings and the corresponding alignment features 414 are upwardly protruding pins. In some embodiments, the transfer head 412 can be a floating head (e.g., a floating head that does not contact the staging device 210a) to limit or prevent binding between the head alignment features 413 and the corresponding alignment features 414. In some embodiments, the transfer head 412 and/or the staging device 210a can include position sensors (not shown) to ensure proper alignment of the head alignment features 413 with respect to the corresponding alignment features 414.

The transfer head 412 can also include one or more capture features 416. The capture feature 416 can include, without limitation, one or more suction devices (e.g., suction cups, pumps, vacuum pumps, etc.), mechanical grippers (e.g., jaws, clamps, pinchers, magnets, etc.), or other retention features that, for example, prevent dropping and/or transferring the slide 243 in a misaligned state. For example, the transfer head 412 can include a vacuum port 417 on the lower surface 415. A vacuum source 418 can provide suction at the vacuum port 417 via supply line 419 that is capable of picking up the slide 243 from the staging device 210a and holding the slide during further transport. The vacuum can be reduced and/or eliminated to release the slide 243 following transfer. Sensors 405 (e.g., pressure sensors, air pressure sensors, light sensors, etc.) can be provided on the lower surface 415 and/or within the vacuum port 417, the vacuum source 418 and/or the supply line 419 that detect the presence of a slide 243 retained by the transfer head 412.

FIG. 25 shows the transfer head 412 in a non-engaged position above the staging device 210a during an alignment phase of the slide transfer. The head alignment feature 413 is shown aligned with the corresponding alignment feature 414a. FIG. 26 shows the transfer head 412 lowered (e.g., via a drive mechanism, not shown) in an engaged position above the staging device 210a. The head alignment feature 413 (e.g., pin) is shown received within the opening of the corresponding alignment feature 414a. The vacuum port 417 is shown engaged with an upper surface 247 of the slide 243 (e.g., a label of the slide 243) such that when the vacuum source 418 is activated (e.g., by controller 144 of FIGS. 1 and 2) and the over-travel inhibitor 254a associated with standby platform 240a is disengaged (e.g., vacuum provided by stage vacuum source 281a is reduced and/or eliminated), the slide 243 can be picked up by the transfer head 412. The slide 243 can be removed from the staging device 210a as the transfer head 412 is lifted to the non-engaged position above the staging device 210a. As illustrated in FIG. 26, the head alignment features 413 align with the corresponding alignment features 414 such that the slide 243 can be maintained in the aligned position during slide pickup. After removing the slide 243 from the staging device 210a, the transfer head 414 can transport the slide 243 to the specimen processing station (not shown).

Figure 27:
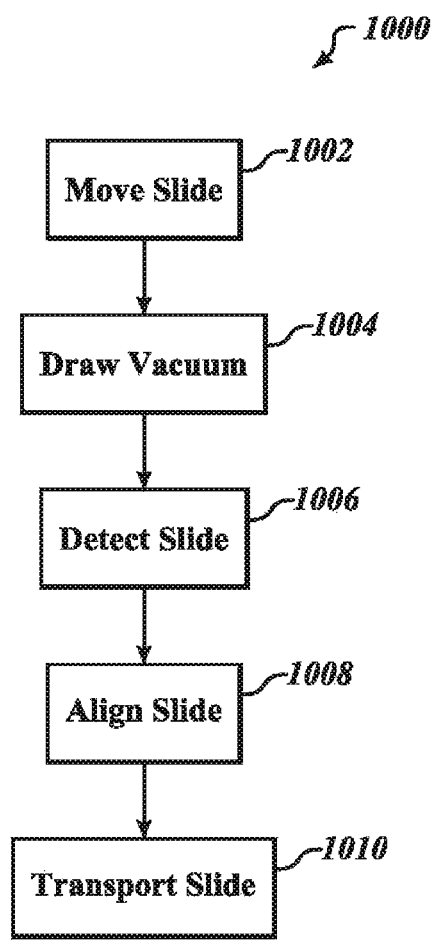
FIG. 27 is a block diagram illustrating a method for transferring a specimen slide using the specimen processing system in accordance with an embodiment of the disclosed technology.

FIG. 27 is a block diagram illustrating a method 1000 for transferring a specimen slide using the specimen processing system 100 described above and with reference to FIGS. 19-26. With reference to FIGS. 19-27 together, the method 1000 can include moving a specimen slide 243 from a slide carrier 170 (FIG. 14) to the standby platform 240a of the staging device 210a (block 1002). The slide 243 can be moved using the ejector 212 by engaging the ejector element with the slide 243 to push the slide onto the slide holding region 250a of the standby platform 240a. The method 1000 can also include drawing a vacuum through the over-travel inhibitor 254a to stop forward movement of the slide 243 on the slide holding region 250a (block 1004). The method 1000 can further include detecting the presence of the slide 243 on the holding region 250a (block 1006). In some embodiments, the presence of the slide 243 can be detected by the controller 144 by changes in the vacuum suction of the over-travel inhibitor 254a. For example, sensors 403 (FIGS. 25 and 26) can be provided to detect the change in pressure within the vacuum port 290, fluid lines 283 and/or vacuum source 281 (see FIG. 16). In other embodiments, the presence of the slide on the standby platform 240a can be detected using other sensors 382 (e.g., pressure sensors, light sensors, motion sensors, etc.). For example, the standby platform 240a can include one more sensors 382 (e.g., position sensors, pressure sensors, light sensors) for detecting the presence of the slide 243. The method 1000 can also include aligning the slide 243 from an misaligned position to an aligned position (block 1008). For example, an actuator can move aligning members 362, 364 toward the slide 243 such that first, second and third contact regions 377, 378, 379 engage the slide to move the slide to the aligned position. Following alignment of the slide 243, the actuator can move the aligning members 362, 364 back to a starting position and away from the aligned slide. The method 1000 can further include transporting the slide 243 from the standby platform 240a to, for example, a specimen processing station while maintaining alignment of the slide (block 1010). For example, a transport assembly 410 having a transfer head 412 can be aligned with the standby platform 240a via alignment of the head alignment features 413 on the transfer head 412 with corresponding alignment features 414 on the standby platform 240a. The transfer head 412 can be configured to engage, pick up and transport the slide 243 with the capture feature 416. In one embodiment, the capture feature 416 can use a vacuum provided by the vacuum source 418 via the vacuum port 417.

Figure 28:
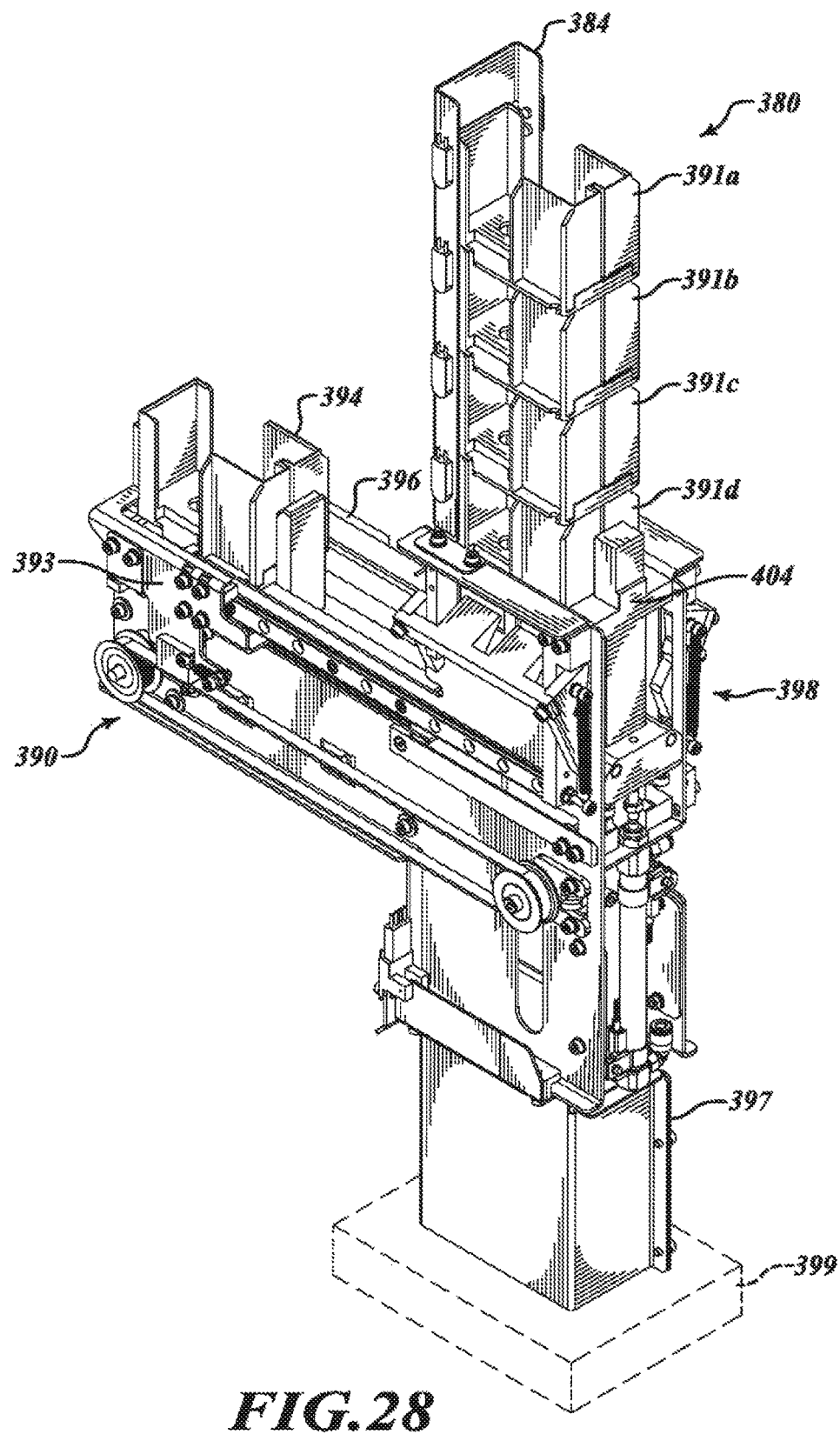
FIG. 28 is an isometric view of an opposable dispenser in accordance with an embodiment of the disclosed technology.
Figure 29:
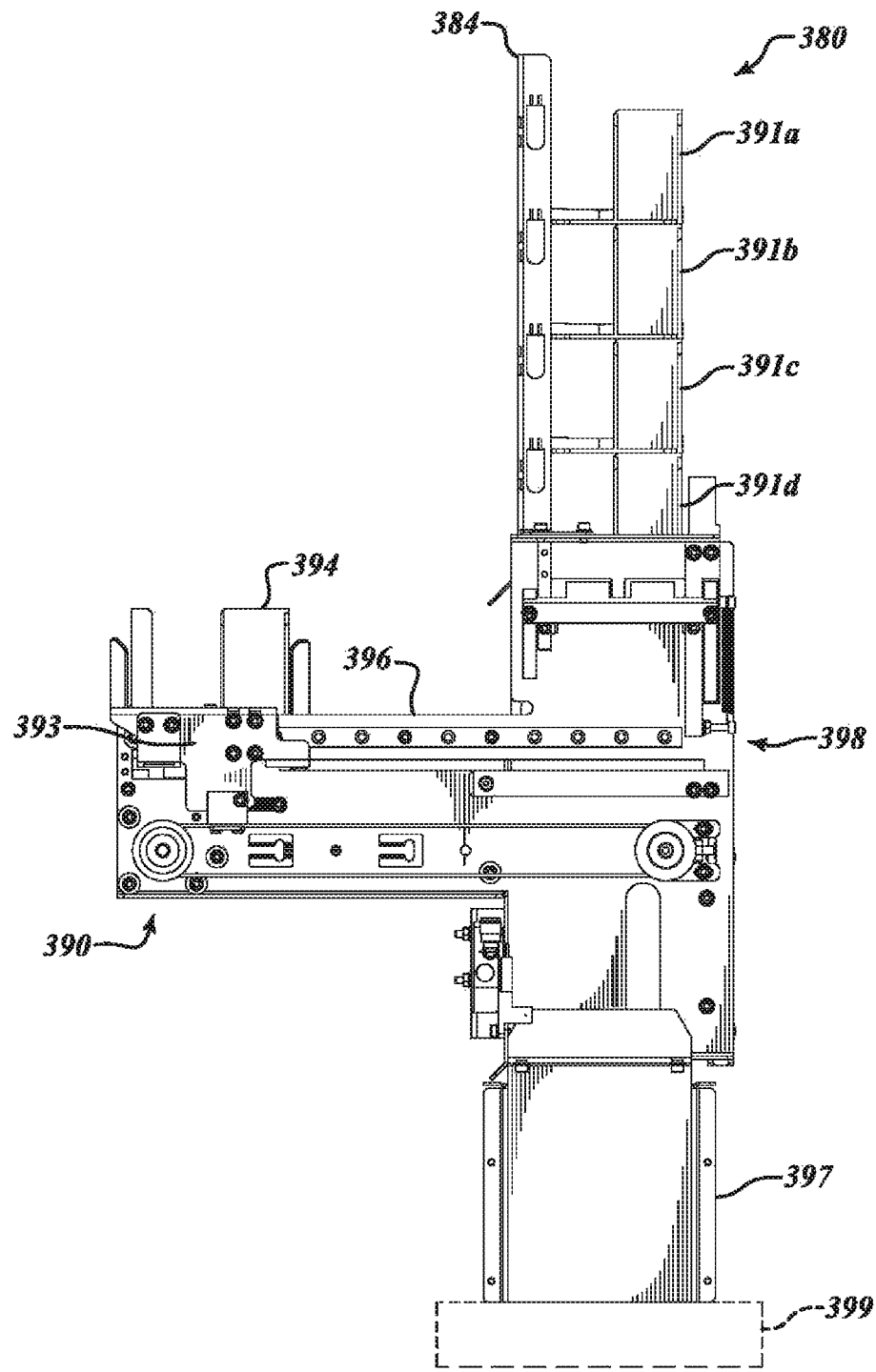
FIG. 29 is a side view of the opposable dispenser of FIG. 28.

FIGS. 28 and 29 show an opposable dispenser 380 that includes an opposable carrier holder 384 ("holder 384") and a conveyor system 390. A transfer mechanism can transport opposable carriers from the loading station 130 (FIG. 1) to the holder 384. In some embodiments, including the illustrated embodiment, the holder 384 is configured to hold four magazines 391a, 391b, 391c, 391d (collectively "391"), each holding 30 opposables, to provide an on-board capacity of 120 opposables. In other embodiments, the dispenser 380 can hold a higher or lower number of magazines or other type of opposable carriers.

The conveyor system 390 includes a carriage 393, a rail 396, and an actuation mechanism 398. The actuation mechanism 398 can include an actuator (e.g., a piston assembly, a pneumatic cylinder, etc.) that moves a vertical lift 404 to raise and/or lower the magazines 391. The carriage 393 can carry a lowered opposable magazine to an unload position at the end of the rail 396. FIGS. 28 and 29 show an empty magazine 394 at the unload position. The vertical lift 404 moves up to retrieve the next magazine 391 and the carriage 393 moves the empty magazine 394 underneath the stack of magazines 391. The carriage 393 can release the empty magazine 394 such that the magazine 394 falls down a chute 397 to a storage bin 399 (illustrated in phantom line).

Figure 30:
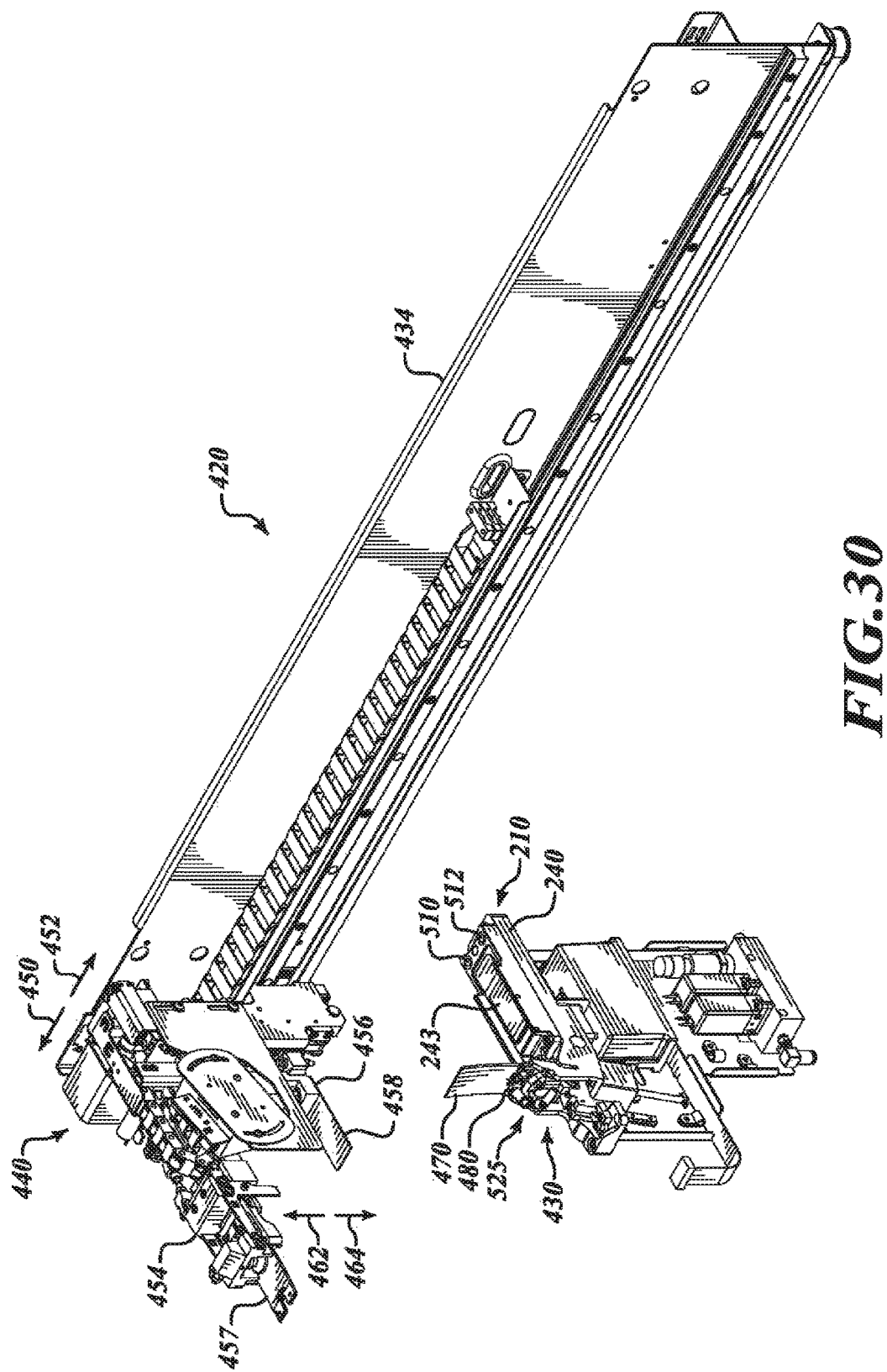
FIG. 30 is an isometric view of a transport assembly and a specimen processing station in accordance with an embodiment of the disclosed technology.

FIG. 30 shows a transport assembly 420 and a specimen processing station in the form of a slide processing station in the form of a wetting module 430. Slides can be individually processed at the wetting module 430 to avoid carryover of liquids, excessive waste (e.g., reagent waste), and/or reagent degradation to provide consistent processing. The wetting module 430 can use an opposable element 470 to motivate liquids to enhance processing consistency, reduce processing times, and allow processing with low concentration reagents. Relatively low volumes of reagents can be used to uniformly stain specimens. Relatively low volumes of washing solutions can be used to thoroughly wash specimens in a relatively short period of time. Washing cycles can be performed before, between, and after staining cycles. After processing of the specimen, the transport assembly 420 can replace the used opposable 470 with a new opposable 457 and replace the used slide 243 with a new slide 458.

The transport assembly 420 can include, without limitation, a drive mechanism 434 (e.g., a rack drive mechanism, a belt drive mechanism, etc.) and a lift mechanism 440. The drive mechanism 434 can move the lift mechanism 440 horizontally, as indicated by arrows 450, 452. The lift mechanism 440 can move end effectors in the form of transfer heads 454, 456 vertically, as indicated by arrows 462, 464. The transfer heads can include, without limitation, one or more suction devices (e.g., suction cups, pumps, vacuum pumps, etc.), mechanical grippers (e.g., jaws, clamps, etc.), retention features (e.g., features that prevent dropping of slides/opposables), or the like. For example, the transfer head 454 can be a pickup head (e.g., a rotatable or floating pickup head) capable of picking up and holding an opposable 457 via a vacuum. The vacuum can be reduced (e.g., eliminated) to release the opposable 457. Additionally or alternatively, a mechanical gripper can hold the opposable 457.

Figure 31:
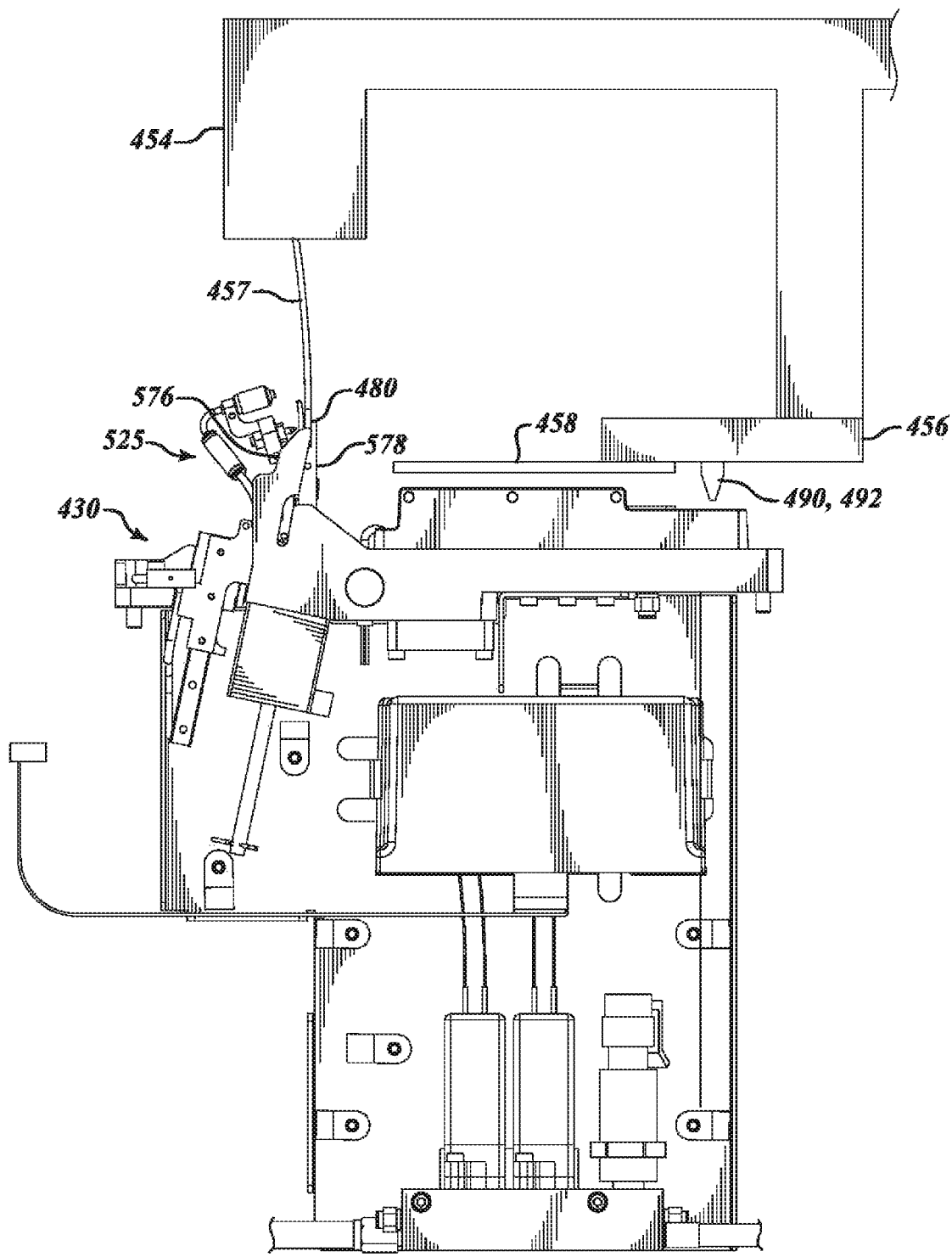
FIG. 31 is a side view of a transport assembly ready to deliver an opposable and a slide to a specimen processing station in accordance with an embodiment of the disclosed technology.

FIG. 31 shows the transfer heads 454, 456 delivering the opposable 457 and slide 458, respectively, to the wetting module 430. The transfer head 456 includes head alignment features 490, 492 receivable by complementary alignment features 500, 502 (FIG. 30) of the standby platform 240 and/or alignment features 510, 512 (FIG. 30) of the wetting module 430. Alignment features can include, without limitation, pins (e.g., elongate rods), protrusions, openings (e.g., openings defined by bushings, openings in plates, etc.), or the like. In some embodiments, the alignment features 490, 492 are in the form of pins that can be inserted into corresponding alignment features 510, 512 in the form of openings to align the slide 243 with the wetting module 430. The transfer head 456 can be a floating head to limit or prevent binding between the alignment features 490, 492 and the alignment features 510, 512, respectively. In other embodiments, the alignment features 490, 492 are openings and the alignment features 510, 512 are upwardly protruding pins.

After removing the processed slide 243, the transfer head 456 can transport an unprocessed slide 458 from a staging device to the wetting module 430. The alignment features 490, 492 can be positioned above the alignment features 510, 512, and the transfer head 456 can be lowered to insert the alignment features 490, 492 into the alignment features 510, 512, respectively, until the slide 458 rests on the wetting module 430. The transfer head 456 can release the slide 458. After processing the specimen, the transfer head 456 can retrieve and load another slide into the wetting module 430. The slides can be retained at the wetting module 430 to prevent damage to the slide in the event of a power outage or other event that may affect system performance.

After removing the used opposable 470, the transfer head 454 can deliver the opposable 457 to an opposable receiver 480. Once the opposable 457 is positioned above the wetting module 430, the transfer head 454 can rotate the opposable 457 from a substantially horizontal orientation (FIG. 30) to a substantially vertical orientation (FIG. 31). In some embodiments, the opposable 457 in the substantially horizontal orientation defines an angle less than 5 degrees with an imaginary horizontal plane, and an opposable in the substantially vertical orientation defines an angle less than 5 degrees with an imaginary vertical plane. The vertically oriented opposable 457 can be loaded into the opposable receiver 480. The transfer head 454 can remove used opposables and retrieve unused opposables from an opposable carrier (e.g., the opposable carrier holder 384 of FIGS. 28 and 29) and can load the unused opposables into the opposable receiver 480.

Figure 32:
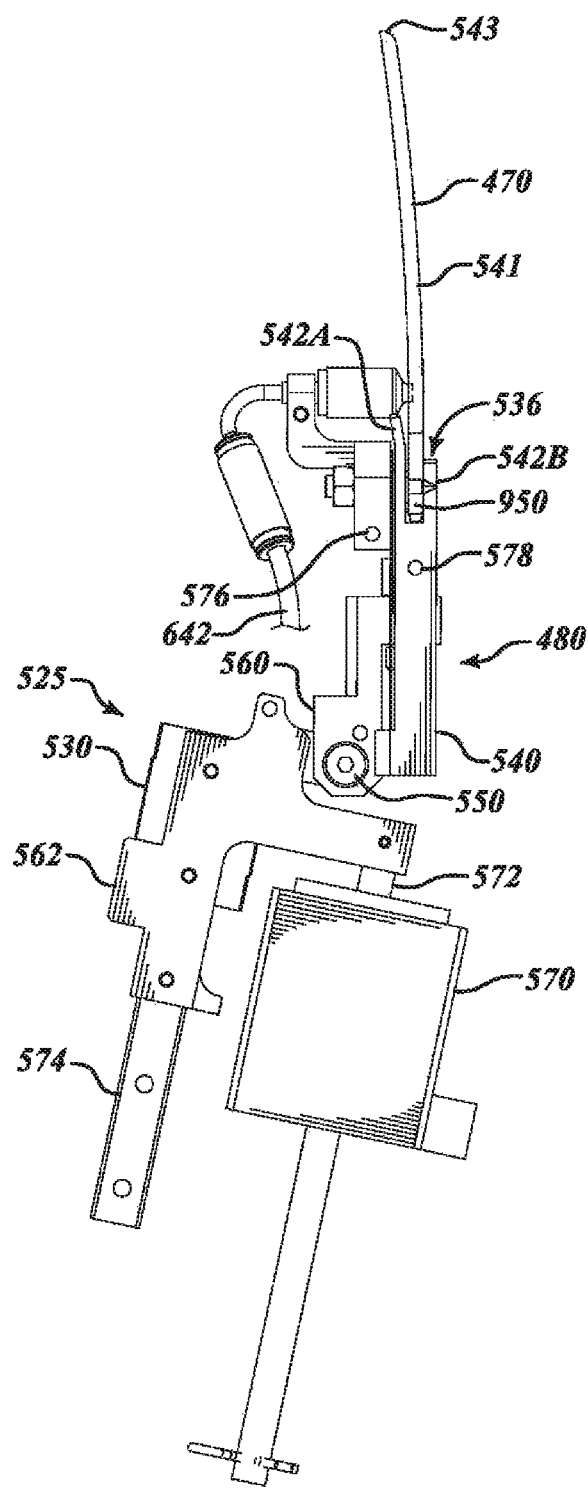
FIG. 32 is a side view of an opposable actuator holding an opposable in accordance with an embodiment of the disclosed technology.

FIG. 32 shows an opposable actuator 525 that includes the opposable receiver 480 and a drive mechanism 530. The opposable receiver 480 can include a clamp 536 and a main body 540. The clamp 536 includes a pair of jaws 542A, 542B that cooperate to hold a mounting end 950 of the opposable 470. The opposable 470 includes a main body 541 extending to a captivating end 543. The main body 541 is pivotally coupled to the drive mechanism 530 by a pivot 550. The drive mechanism 530 can include a linkage assembly 560 and a linear actuator assembly 562. The linkage assembly 560 includes the pivot 550, which allows rotation about one or more axes of rotation (e.g., two axes of rotation) and can include one or more roller ball bearings, pivots, hinges, or other features that provide desired motion. The linear actuator assembly 562 can include an energizable drive device 570 (e.g., a stepper motor, a drive motor, a solenoid, etc.), a moveable element 572 (e.g., a lead screw, a drive rod, etc.), and a rail assembly 574 (e.g., a carriage/rail assembly, a caged ball bearing linear rail assembly, etc.).

The opposable receiver 480 can be actuated by the linear actuator assembly 562 via the linkage assembly 560. The linear actuator assembly 562 can retract, and stationary cam(s) (e.g., cam 575 of FIG. 33) can engage, pins 576, 578 and drive the opposable receiver 480 to an open configuration. In some embodiments, including the illustrated embodiment of FIG. 32, the opposable receiver 480 in the open configuration can loosely hold the opposable 470. The opposable receiver 480 can be moved to a closed configuration by one or more biasing members (e.g., springs, pneumatic actuators, etc.). As the linear actuator assembly 562 extends, the pins 576, 578 can move upwardly and toward one another such that the biasing members close the opposable receiver 480.

The opposable actuator 525 can also include, without limitation, one or more sensors to detect the presence of the opposable 470, the position of the opposable 470, one or more characteristics of a processing liquid engaged by the opposable 470, or the like. The sensors can include, without limitation, contact sensors, electromechanical sensors, optical sensors, or chemical sensors that can be coupled to or incorporated into the opposable receiver 480 or other suitable component. The number, positions, and configurations of the sensors can be selected to achieve the desired monitoring functionality.

Figure 33:
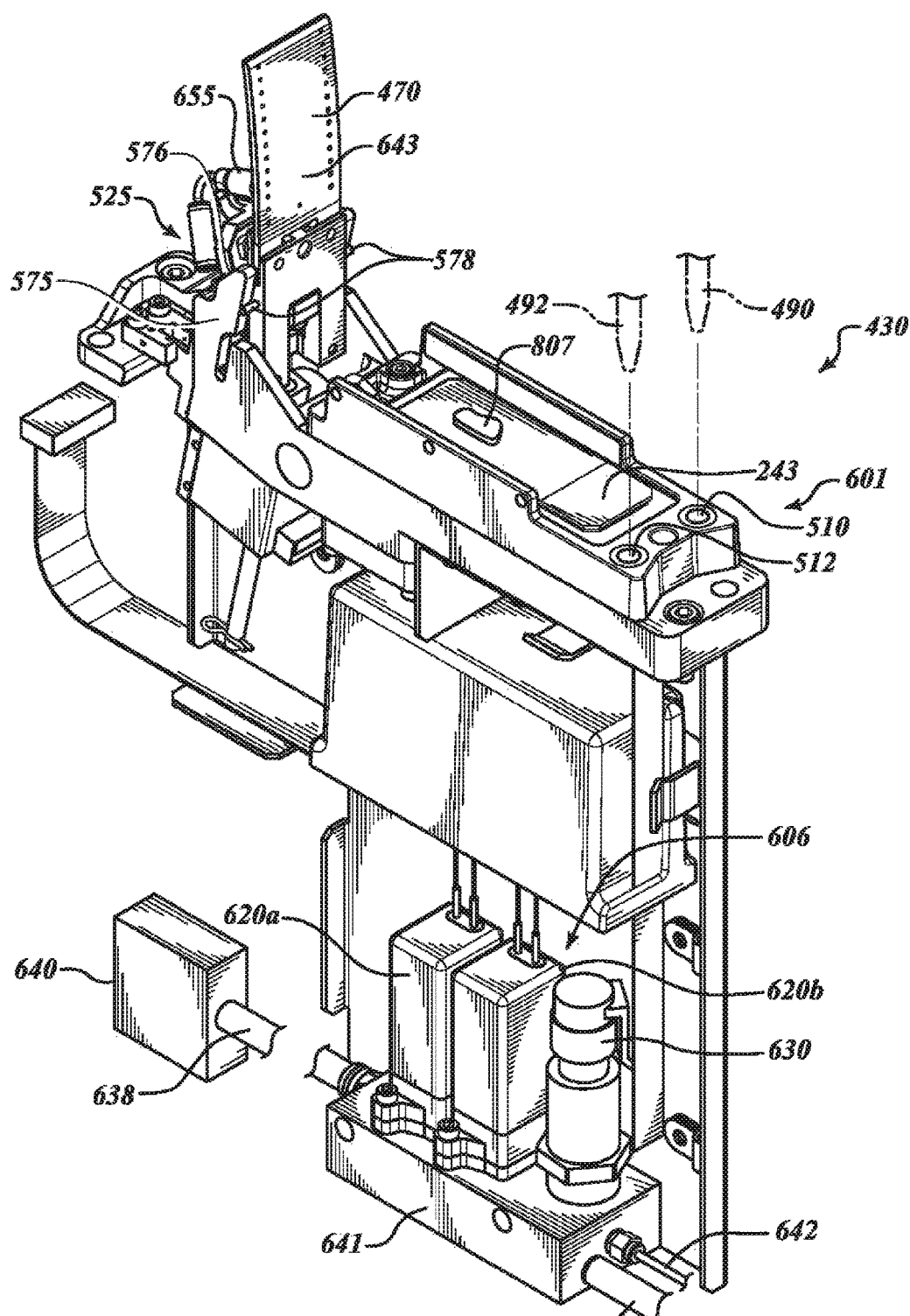
FIG. 33 is an isometric view of a specimen processing station ready to process a specimen on a slide in accordance with an embodiment of the disclosed technology.

FIG. 33 is an isometric view of the wetting module 430 holding the slide 243 in accordance with an embodiment of the present technology. The wetting module 430 includes the opposable actuator 525, a slide holder platen 601, and a manifold assembly 606. The opposable actuator 525 in a rolling state of operation can be extended or retracted to roll the opposable 470 back and forth along the slide 243. The motion of the rotary joints of the linkage assembly 560 (FIG. 32), gravity, and/or liquid capillary forces can help maintain the desired motion of the opposable 470. In some embodiments, the opposable actuator 525 can continuously or periodically roll (e.g., longitudinally roll, laterally roll, or both) the opposable 470 to agitate the volume of liquid, move (e.g., translate, spread, narrow, etc.) a band of liquid (e.g., a meniscus layer of liquid), control evaporation (e.g., to moderate evaporation), and/or otherwise manage the processing liquid.

The manifold assembly 606 includes a pair of sensors 620a, 620b (collectively "620") and a one or more valves 630. The sensors 620 can detect the pressures of working fluids and can send one or more signals indicative of detected pressures. A fluid line 638 can fluidically couple a pressurization source 640 to a manifold 641. Fluid lines 642, 644 fluidically couple the manifold 641 to a liquid removal device 655 and the slide holder platen 601. The liquid removal device 655 can remove liquid between the opposable 470 and the slide 243 via a waste port 643. The line 644 can be used to draw a vacuum to hold the slide 243 on the slide holder platen 601.

FIGS. 34A and 34B are isometric views of the slide holder platen 601 in accordance with an embodiment of the present technology. The slide holder platen 601 of FIG. 34A supports the slide 243. The slide holder platen 601 of FIG. 34B is empty. The slide holder platen 601 can include a support element 650 and a mounting base 651. The support element 650 includes a raised slide receiving region 680 having a contact or contact surface 679 (FIG. 34B). A port 683 (FIG. 34B) is positioned to draw a vacuum to hold the slide 243 against the contact surface 679. The port 683 can be a suction cup or other feature configured to facilitate drawing a strong vacuum between the slide 243 against the contact surface 679.

The support element 650 includes inner walls 681 positioned in outer walls 652 of the mounting base 651. The inner and outer walls 681, 652 form heatable sidewalls 682. In some embodiments, the sidewalls 682 can be positioned on both sides of the contact surface 679 and can output heat energy to the surrounding air to control the temperature of the slide 243, processing fluid, and/or specimen(s). In some embodiments, the sidewalls 682 can also be positioned to laterally surround the entire slide 243. The mounting base 651 can be made of an insulating material (e.g., plastic, rubber, polymers, or the like) that can insulate the support element 650 from other components. In some embodiments, the mounting base 651 is made of a material with a thermal conductivity that is substantially less than the thermal conductivity of the material of the support element 650. The mounting base 651 can surround and protect the support element 650 and includes a coupling region 657 to which the opposable actuator 525 can be coupled.

The support element 650 can be an uncoated element comprising one or more low heat transfer material(s) with a low thermal conductivity. Low heat transfer materials can include, without limitation, steel, stainless steel, or other materials with a thermal conductivity in a range of about 10 W/(m*K) at 25° C. to about 25 W/(m*K) at 25° C. In one embodiment, the low heat transfer material comprises stainless steel with a thermal conductivity of 16 W/(m*K) at 25° C. In some embodiments, the support element 650 comprises mostly stainless steel by weight. In certain embodiments, at least most of the material of the support element 650 directly between a heating element 653 (FIG. 35) and the slide 243 comprises stainless steel by weight. The stainless steel support element 650 can be corrosion-resistant to the liquids used to process the specimens to provide a relatively long working life. In some embodiments, support element 650 comprises antimony (k=18.5 W/(m*K) at 25° C.) or chrome nickel steel (e.g., 18% Cr and 8% Ni by weight and with a thermal conductivity of about 16.3 W/(m*K) at 25° C.). In other embodiments, the support element 650 can comprise lead with a thermal conductivity of about 35 W/(m*K) at 25° C.) or other metal with a similar thermal conductivity. In some embodiments, the support element 650 can be made of a material with thermal conductivity less than copper or brass. The mounting base 651 can be made of an insulating material with a thermal conductivity that is less than the thermal conductivity of the support element 650. As such, the mounting base 651 can thermally insulate the support element 650.

Figure 35:
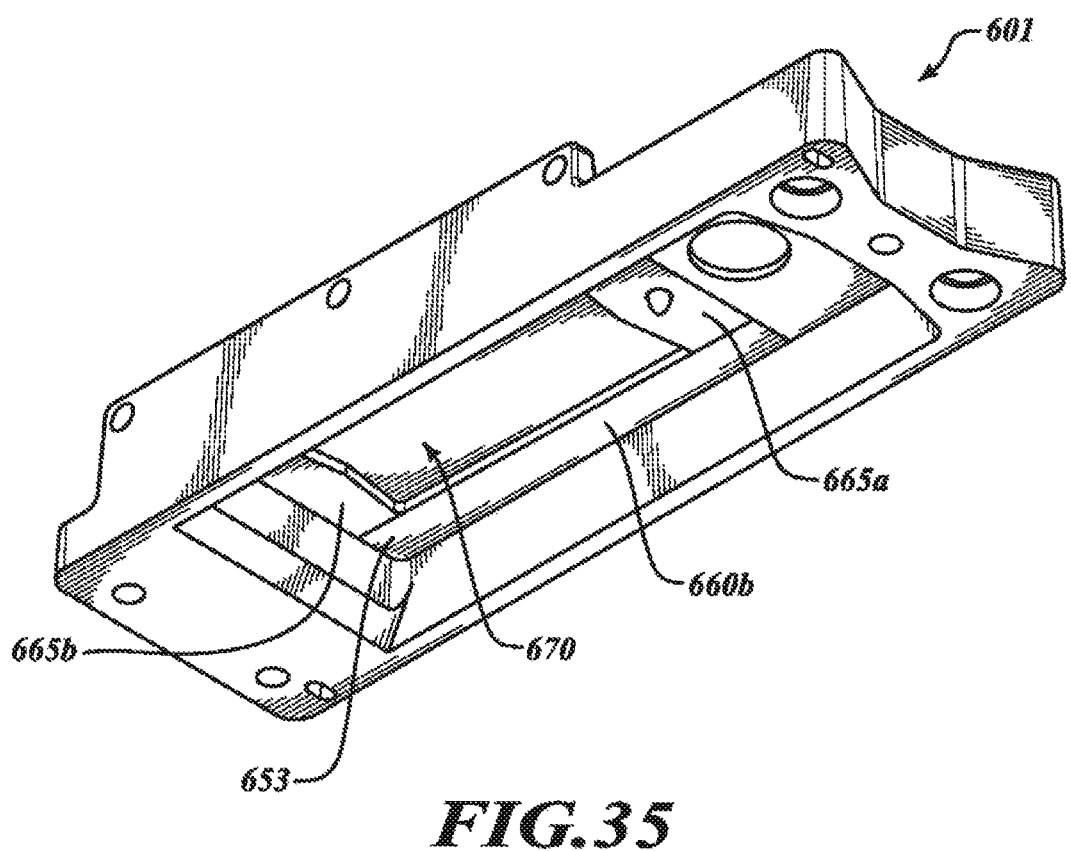
FIG. 35 is a front, bottom, left side isometric view of the slide holder platen of FIG. 34A.
Figure 36:
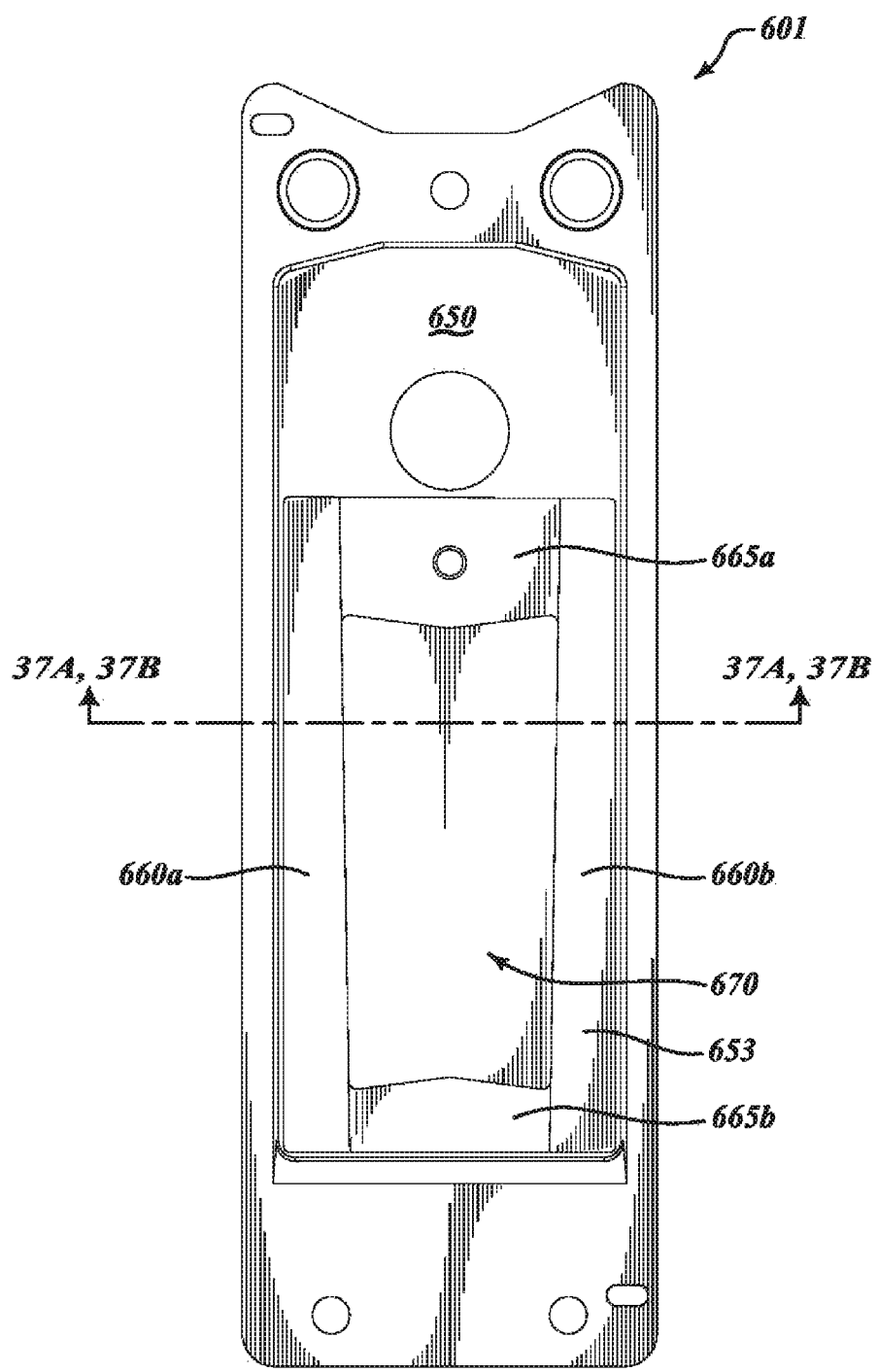
FIG. 36 is a bottom view of the slide holder platen of FIG. 34A.

FIG. 35 is a front, bottom, left side view of the slide holder platen 601. FIG. 36 is a bottom view of the slide holder platen 601. The slide holder platen 601 can include the heating element 653, which can convert electrical energy to thermal energy and can include, without limitation, one or more traces, leads, resistive elements (e.g., active elements that produce thermal energy), fuses, or the like. In some embodiments, the heating element 653 can be a resistive heater. Other types of heaters can also be used, if needed or desired. In some embodiments, the heating element 653 can output thermal energy to the support element 650 to achieve a desired heat transfer pattern. Heat can be transferred non-uniformly to the slide 243 via the support element 650 to compensate for evaporative heat losses. Non-uniform heat transfer along the contact surface 679 may produce a non-uniform temperature profile along the contact surface 679. A generally uniform temperature profile can be produced across a processing zone 671 (FIG. 34A) of slide 243. The processing zone 671 can be a staining region, a mounting region, or area of an upper or specimen-bearing surface 687 (FIG. 34A) of the slide 243 suitable for carrying one or more specimen(s).

The heating element 653 of FIG. 36 can include two elongate slide heating portions 660a, 660b (collectively 660) and two end heating portions 665a, 665b (collectively "665"). The elongate portions 660 deliver thermal energy to the longitudinally extending edge portions of the slide 243. The end heating portions 665 deliver thermal energy to the ends of the processing zone 671. The elongate portions 660 and the end heating portions 665 can be coupled together to form a multi-piece heating element 653. The elongate portions 660 and the end heating portions 665 can be made of materials with the same conductivity or different thermal conductivities. Each portion 660, 665 can be independently operated to output different amounts of thermal energy. In other embodiments, the heating element 653 can have a one-piece construction with a uniform thickness or a variable thickness. The one-piece heating element 653 can be made of one material.

The elongate portions 660 and end heating portions 665 together define a convection cooling feature in the form of a pocket 670. The pocket 670 can help isolate heat in the support element 650 to help keep thermal energy at the location it is applied and can also help reduce or limit the thermal mass of the slide holder platen 601. The pocket 670 can be an opening with a substantially rectangular shape, as shown in FIG. 36. However, the pocket 670 can have other shapes based on the desired heat distribution along the contact surface 679 of the support element 650.

Figure 37A:
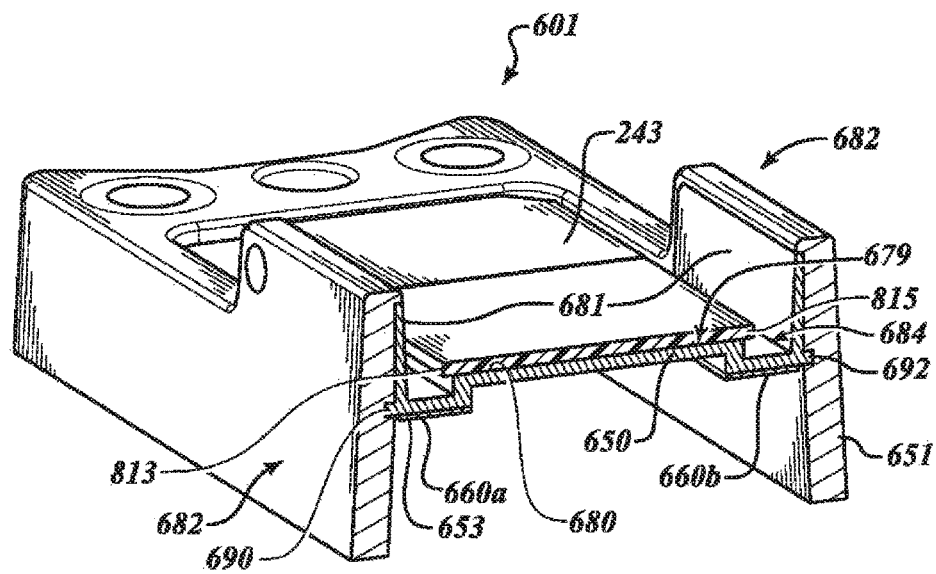
FIG. 37A is a cross-sectional isometric view of the slide holder platen taken along a line 37A-37A of FIG. 36.

FIG. 37A is a cross-sectional isometric view of the slide holder platen 601. The support element 650 includes the receiving region 680, sidewalls 682, and a channel 684. The receiving region 680 keeps the slide 243 spaced apart from fluids that can collect in the channel 684 during operation. The channel 684 can collect liquid that falls from edges 813, 815 of the slide 243. In some embodiments, the slide 243 can extend outwardly from the receiving region 680 a sufficient distance (e.g., 0.5 mm, 0.75 mm, 1 mm, 2 mm, 4 mm, or 6 mm) to prevent liquid from wicking between the slide 243 and the contact surface 679.

The slide holder platen 601 can be made in a multi-step manufacturing process. The support element 650 can be formed by a machining process, stamping process, or the like. The support element 650 can be over-molded to form the mounting base 651, which can be made of an insulating material molded using an injection molding process, compressing molding processes, or other suitable manufacturing processes. Exemplary non-limiting insulating materials include, without limitation, plastics, polymers, ceramics, or the like. The support element 650 and mounting base 651 can remain securely coupled together to inhibit or prevent liquids from traveling between the support element 650 and mounting base 651. For example, the interface between the supporting element 650 and the mounting base 651 can form a fluid-tight seal with or without utilizing any sealants. However, sealants, adhesives, and/or fasteners can be used to securely couple the support element 650 to the mounting base 651. The illustrated support element 650 includes locking features 690, 692 to help minimize, limit, or substantially prevent movement of the support element 650 relative to the mounting base 651.

Figure 37B:
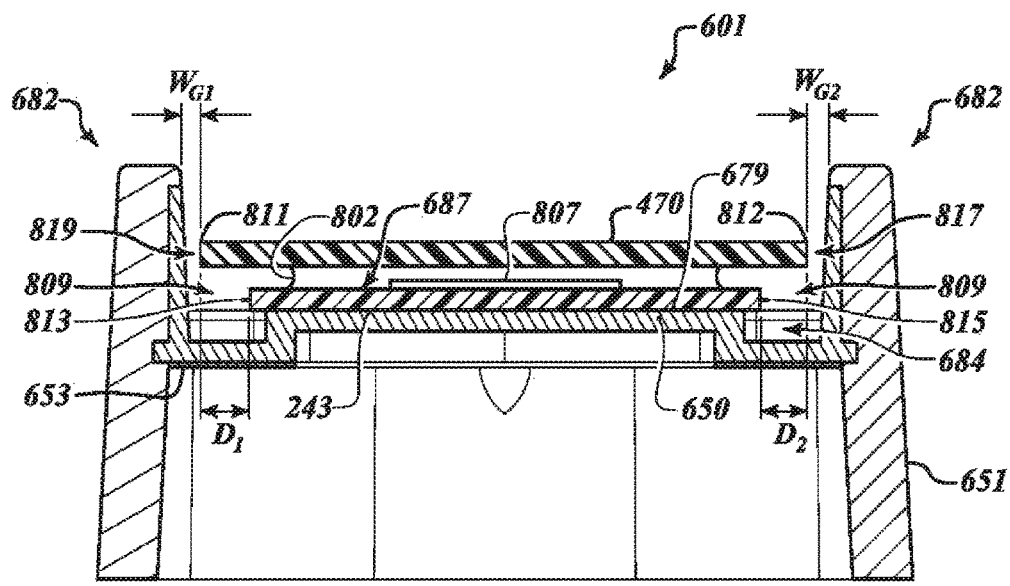
FIG. 37B is a cross-sectional view of the slide holder platen taken along a line 37B-37B of FIG. 36.

FIG. 37B is a cross-sectional view of the slide holder platen 601. The opposable 470 engages a liquid 802 which engages a specimen 807. The sidewalls 682 can extend vertically past the slide 243. The distance that the sidewalls 682 extend vertically past the slide 243 can be selected to manage (e.g., limit, minimize, substantially prevent, etc.) air currents that can cause heat losses via convection (e.g., convection via the surrounding air), evaporation, or the like. For example, the slide holder platen 601 and opposable 470 can moderate evaporation by keeping the evaporation rate of the liquid 802 at or below about 7 microliters per minute, 5 microliters per minute, 3 microliters per minute or other maximum evaporation rates. In some embodiments, the slide holder platen 601 and opposable 470 can keep the evaporation rate of the liquid 802 within a range of about 7 microliters per minute to about 1 microliters per minute.

Such embodiments can moderate evaporative losses. The sidewalls 682 and the opposable 470 help substantially thermally isolate the specimen from the surrounding environment. Additionally, the sidewalls 682 can heat the air proximate to the specimen to help prevent the liquid 802 from being cooled by surrounding air and to inhibit or help prevent condensation.

A side portion 811 of the opposable 470 extends outwardly past the edge 813 of the slide 243 such that the side portion 811 is closer to the sidewall 682 than the edge 813 of the slide 243. A width $W_{G1}$ of a gap 819 can be smaller than a distance $D_1$ from the side portion 811 to the slide edge 813. A side portion 812 of the opposable 470 extends outwardly past the edge 815. A width $W_{G2}$ of a gap 817 can be smaller than a distance $D_2$ from the side portion 812 to the slide edge 815. In some embodiments, width $W_{G1}$ can be equal to or less than about 10%, 25%, or 50% of a distance between the left sidewall 682 and the edge 813. Similarly, width $W_{G2}$ can be equal to or less than about 10%, 25%, or 50% of a distance between the right sidewall 682 and the slide edge 815. The widths $W_{G1}$, $W_{G2}$ can be sufficiently small to inhibit or limit evaporative losses while allowing slight side-to-side movement of the opposable 470 to facilitate convenient handling. In some embodiments, the widths $W_{G1}$, $W_{G2}$ are equal to or less than about 1 mm, 2 mm, 4 mm, or other suitable widths.

Figure 38:
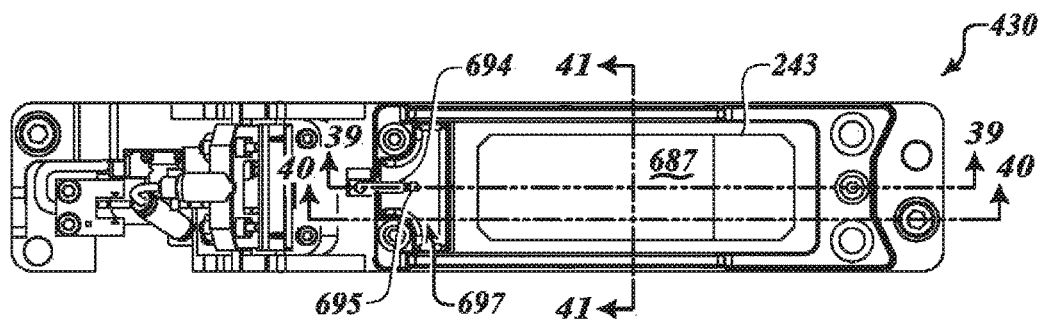
FIG. 38 is a top plan view of a specimen processing station holding a specimen-bearing slide in accordance with an embodiment of the disclosed technology.
Figure 39:
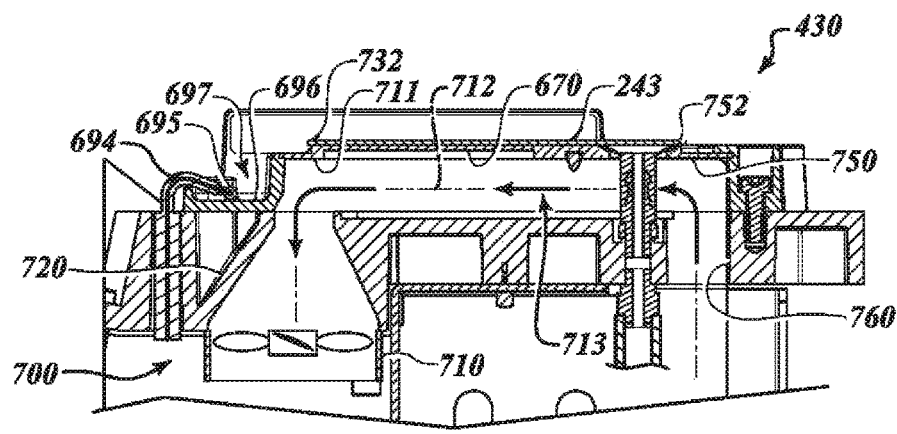
FIG. 39 is a cross-sectional view of a portion of the specimen processing station taken along a line 39-39 of FIG. 38.
Figure 40:
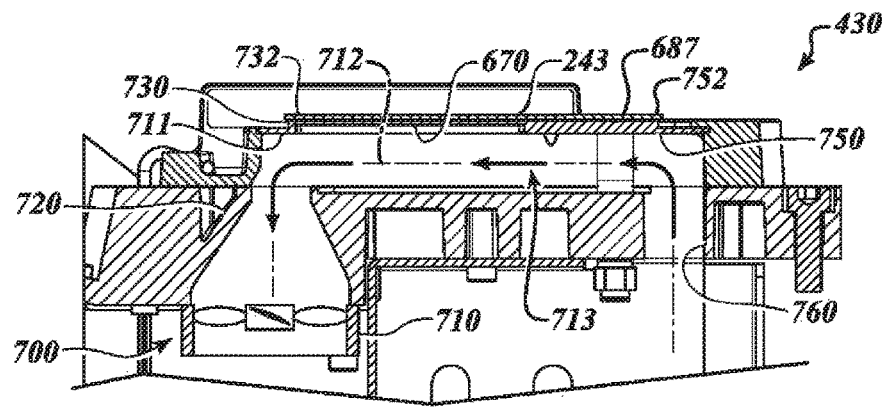
FIG. 40 is a cross-sectional view of a portion of the specimen processing station taken along a line 40-40 of FIG. 38.

FIG. 38 is a top plan view of the wetting module 430. FIG. 39 is a cross-sectional view of a portion of the wetting module 430 taken along a line 39-39 of FIG. 38. FIG. 40 is a cross-sectional view of a portion of the wetting module 430 taken along a line 40-40 of FIG. 38. Referring to FIGS. 38 and 39, a sensor 694 is positioned to detect liquid in a reservoir 697. The sensor 694 can include a thermistor element 695 positioned near a bottom 696 of the reservoir 697. When a sufficient volume of liquid is collected to contact the thermistor element 695, the sensor 694 sends a signal to the controller 144 (FIG. 2). The detection of a threshold volume of liquid in the reservoir 697 can indicate a failure in the wetting module 430. Upon detection of a failure, the wetting module 430 can be disabled until the wetting module 430 can be, for example, inspected, cleaned, or otherwise maintained.

Referring to FIGS. 39 and 40, the wetting module 430 includes a convection system 700 that includes a flow generator 710, a duct 711, and a flow path 712 (illustrated in phantom line) defined by a passageway 713 of the duct 711. The flow generator 710 can include, without limitation, one or more fans, blowers, or other suitable components capable of generating a sufficient flow of a convection fluid (e.g., air, a refrigerant, etc.) along the flow path 712 to cool the back side of the support element 650, the slide 243, and/or items (e.g., specimens, reagents, or the like) carried on the slide 243.

The flow generator 710 can deliver the convection fluid toward an end 730 of the support element 650 located under a first end 732 of the slide 243. The convection fluid can travel vertically through a tapered section 720 that can accelerate the flow of convection fluid. The accelerated flow is directed horizontally and flows under the slide platen 601. The convection fluid can directly contact the support element 650 to facilitate and expedite cooling of the slide 243. For example, the convection fluid can flow into and along the pocket 670 to absorb thermal energy from the support element 650. The support element 650 absorbs thermal energy from the slide 243 to cool the upper surface 687 and to ultimately cool a liquid, specimen(s), or any other items or substances on the upper surface 687. The warmed fluid flows past the pocket 670 and proceeds under an end 750 of the support element 650 positioned underneath a label end 752 of the slide 243. The air flows downwardly through an outlet 760 to the surrounding environment.

The convection system 700 can be used to rapidly cool the slide 243. For example, the convection system 700 can help cool the liquid and/or specimen at a rate equal to or greater than about 2.5° C./sec. In one embodiment, the temperature of a specimen can be at about 95° C. and can be cooled to a temperature equal to or less than about 30° C. in about four minutes or less. Other cooling rates can be achieved by increasing or decreasing the flow rate of the convection fluid, temperature of the convection fluid, or the like. During a heating cycle, the convention system 700 can be OFF, if desired.

Figure 41:
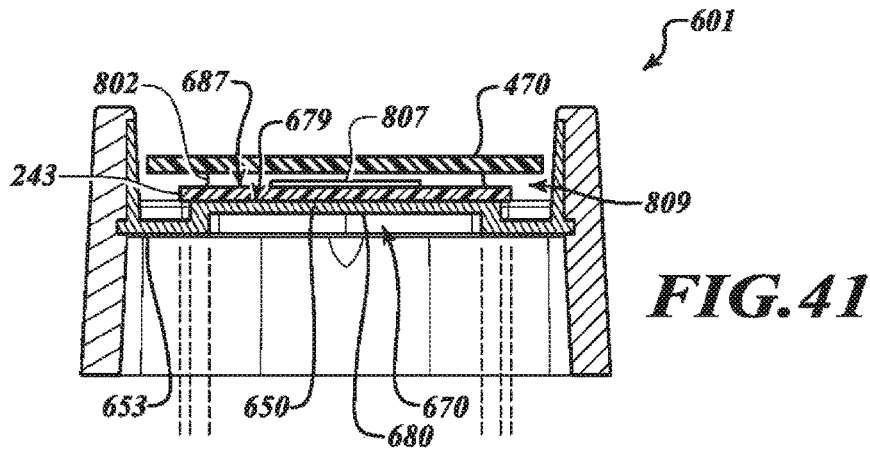
FIG. 41 is a cross-sectional view of a slide holder platen taken along a line 41-41 of FIG. 38.

FIG. 41 is a cross-sectional view of a portion of the slide holder platen 601 taken along a line 41-41 of FIG. 38. The temperature of the liquid 802 can be maintained within a target temperature range selected based on the characteristics of the liquid 802, characteristics of a specimen (e.g., a thickness of the specimen, composition of the specimen, etc.), and the process to be performed. Because the regions of the liquid 802 nearest the edges of the slide 243 evaporate more than the central region of the liquid 802, the periphery of the slide 243 and the periphery of the liquid 802 tend to be at a lower temperature without compensation. The evaporative heat losses for high temperature processes (e.g., antigen retrieval) may be greater than the evaporative losses for low temperature processes (e.g., rinsing). Because significant temperature variations along the specimen 807 and/or the liquid 802 can lead to variations in processing, the wetting module 430 can maintain a desired temperature profile of the slide 243 by compensating for evaporative heat losses, including evaporative heat losses in high temperature and low temperature processes. The wetting module 430 can produce a substantially uniform temperature profile along the surface 687 to substantially uniformly heat the band of liquid 802 and/or the specimen 807. The uniform temperature profile can be maintained independently of changes in the surrounding environment to consistently process the entire specimen 807.

Figure 41A:
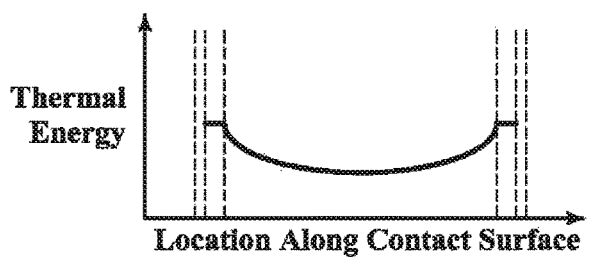
FIG. 41A is a plot of location along a contact surface of a slide support versus thermal energy conducted to a slide in accordance with an embodiment of the disclosed technology.
Figure 41B:
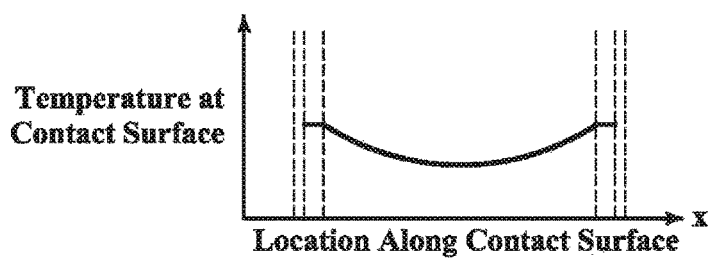
FIG. 41B is a plot of location along the contact surface of the slide support versus temperature of the contact surface in accordance with an embodiment of the disclosed technology
Figure 41C:
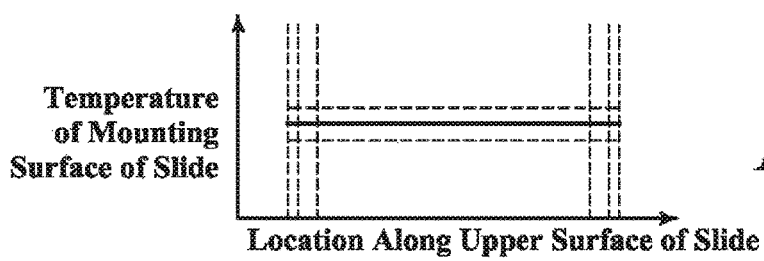
FIG. 41C is a plot of location along an upper surface of a slide versus temperature of the upper surface of the slide in accordance with an embodiment of the disclosed technology.

FIG. 41A is a plot of the location along the width of the receiving region 680 versus thermal energy conducted to the slide 243. FIG. 41B is a plot of the location along the width of the receiving region 680 versus a temperature of the contact surface 679 of the support element 650. FIG. 41C is a plot of a location along the upper surface 687 of the slide 243. A comparison of FIGS. 41B and 41C shows that the temperature profile along the contact surface 679 of the support element 650 is different from the temperature profile along the upper surface 687 of the slide 243.

Referring to FIG. 41A, the heating element 653 can non-uniformly transfer heat energy via conduction to the slide 243. The heat remains concentrated at the perimeter of the staining region where evaporative heat losses are relatively high. Because no heat energy is directly transferred via conduction to the portion of the support element 650 above the pocket 670, a non-uniform temperature profile is produced along the contact surface 679 of the support element 650 and can compensate for non-uniform heat losses associated with evaporation of the liquid 802. The compensation can produce a substantially uniform temperature profile along the upper slide surface 687. As shown in FIG. 41C, a temperature along the upper slide surface 687 can be kept within a target temperature range (represented by two horizontal dashed lines). In an embodiment for antigen retrieval, the substantially uniform temperature profile can have a temperature variation that is equal to or less than 5% of the desired temperature and can be across most of the upper slide surface 687. The upper slide surface 687 can be kept at, for example, an average temperature or target temperature of about 95° C. and within a range of about 90.25° C. and about 99.75° C. In some embodiments, the heater element 653 produces less than about a 4% temperature variation across most of the upper slide surface 687. In other embodiments, there can be less than 5% temperature variation across most of the upper slide surface 687. The upper slide surface 687 can be kept at, for example, an average temperature of about 95° C. and within a range of about 92.63° C. and about 97.38° C. In some embodiments, an allowable temperature variation can be inputted by a user.

Figure 42:
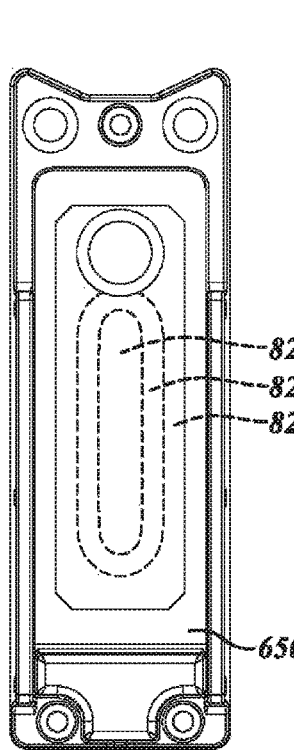
FIG. 42 is a top plan view of heating zones produced on a slide support surface of the support element in accordance with an embodiment of the disclosed technology.

FIG. 42 is a top view of heating zones in accordance with an embodiment of the present technology. A high heating zone 820 surrounds an intermediate heating zone 824. The intermediate heating zone 824 surrounds a low heating zone 822. Heat from the heating element 653 primarily travels upwardly to define the high heating zone 820. The high heating zone 820 can be located underneath a perimeter of a staining area of the slide 243. The low heating zone 822 can generally correspond to the pocket 670 and the central processing area (e.g., a staining area) where one or more specimens are typically positioned. The temperature of the heating zones 820, 822, 824 can be generally inversely proportional to the rates of evaporation along the slide directly above that heating zone. For example, the low heating zone 822 can be positioned generally below the middle of the band of liquid 802 in which there is substantially no evaporative losses. The high heating zone 820 is positioned generally below the periphery of the band of liquid 802 that experiences relatively high evaporative losses.

Figure 43:
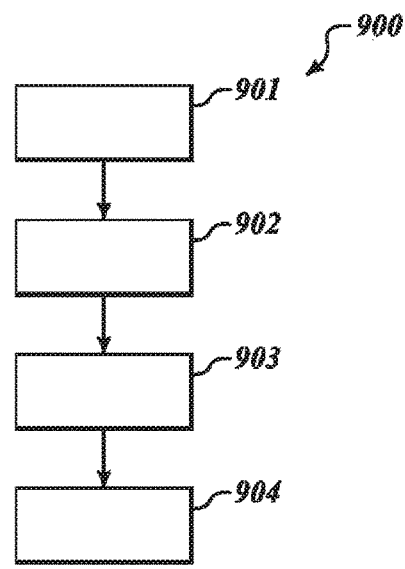
FIG. 43 is a flow chart illustrating a method for heating a slide in accordance with an embodiment of the disclosed technology.

FIG. 43 is a flow chart illustrating a method 900 for heating the slide in accordance with an embodiment of the present technology. At 901, the specimen-bearing slide 243 (FIG. 34A) can be positioned on the contact surface 679 of the support element 650 (FIG. 34B). The slide 243 can be preheated by the slide holder platen 601. A liquid can be delivered onto the heated slide 243. Alternatively, the slide holder platen 601 can heat the slide 243 after delivering the liquid.

At 902, the opposable 470 is used to manipulate the liquid and can mitigate and control evaporation, which in turn can affect temperature, concentration, and capillary volume. In some embodiments, the liquid is allowed to evaporate, resulting in heat losses and, in some embodiments, changes in concentration of the liquid 802. A dispenser can deliver supplemental liquid at desired times to keep the volume of the liquid in a desired range, maintain a desired concentration of the liquid, or the like. If the current volume of the liquid is lower than the target equilibrium volume, the controller can instruct the dispenser to deliver liquid until the current volume of the liquid reaches the equilibrium volume. If the current volume of the liquid is higher than the target equilibrium volume, the controller can instruct the dispenser to stop delivering liquid until the current volume of the liquid reaches the equilibrium volume. Once the liquid reaches the target equilibrium volume, the controller can instruct the dispenser to provide the supplemental fluid to the liquid at a desired rate (e.g., a fixed rate or a variable rate), so as to maintain the liquid at the equilibrium volume. The delivery rate can be selected based on the evaporation rate of the liquid.

At 903, the contact surface 679 can have a non-uniform temperature profile such that the upper surface 687 of the slide 243 has a temperature profile that is more uniform than the non-uniform profile of the contact surface 679. Substantially the entire mounting area of the slide 243 can have a substantially uniform profile. This ensures that any portion of a specimen contacting the mounting surface is maintained at a generally uniform temperature for consistent processing. Even if specimens move slightly along the mounting surface, the specimens can be consistently processed.

At 904, heat losses associated with evaporation of the liquid 802 can be compensated for by producing the non-uniform temperature profile along the contact surface 679. The support element 650 and the heating sidewalls 682 can be used to control the temperature of the slide 243.

Fluid manipulated repeatedly across the staining surface results in fluid mixing between different regions within the body of fluid in contact with the slide surface in the sense of both mass as well as thermal energy mixing. Temperature uniformity control across the surface of the slide, therefore, is influenced by the interaction of 1) the conducting heating element under the slide, 2) thermal mixing resulting from fluid manipulation, and 3) evaporative heat loss with respect to the ambient environment. Fluid manipulation is controlled by such factors as manipulation speed and distance with respect to specified volumes. The thermal profile of the conducting element under the slide therefore must be designed appropriately for optimal on-slide temperature uniformity with respect to fluid manipulation factors.

Figure 44:
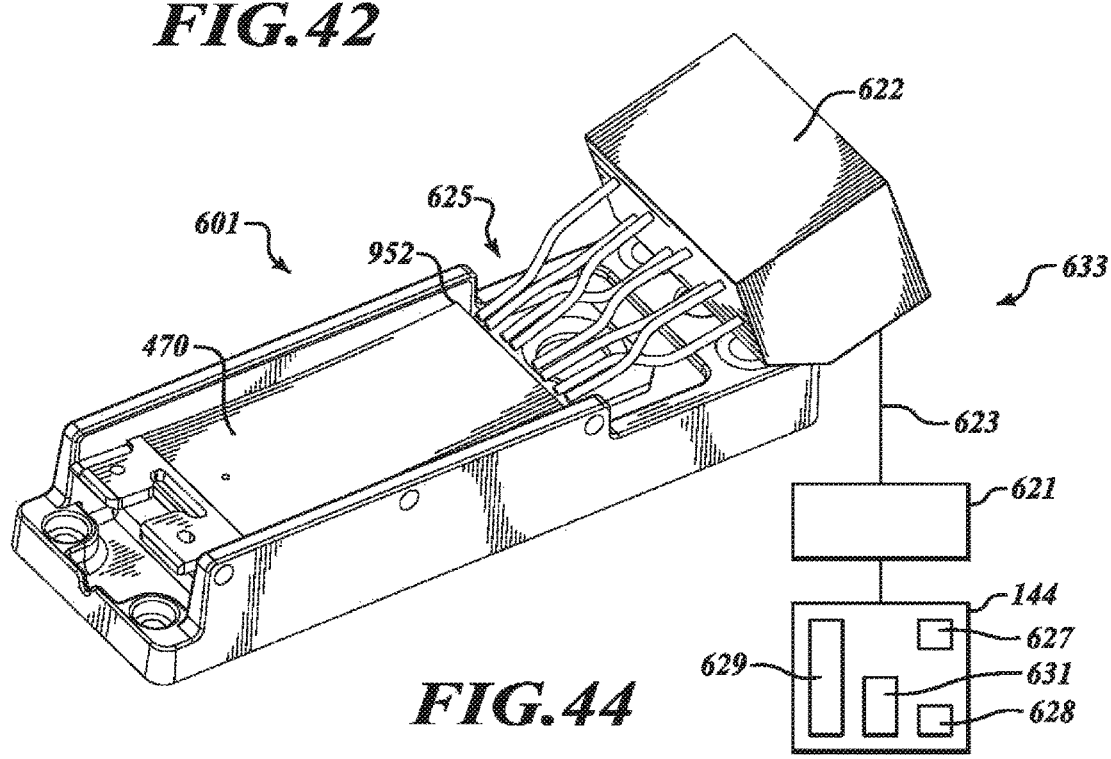
FIG. 44 illustrates a slide holder platen and a dispenser assembly in accordance with an embodiment of the disclosed technology.

FIG. 44 shows the slide holder platen 601, a dispenser assembly 633, and the controller 144 of an evaporation moderated specimen process station. The dispenser assembly 633 includes a fluid source 621 fluidically coupled to a dispenser 622 via a fluid line 623. The fluid source 621 can include, without limitation, one or more containers (e.g., a container taken from the parking station 124 of FIG. 1, a container taken from the parking station 142 of FIG. 1, etc.), reservoirs, or other suitable fluid sources (e.g., a bulk reagent reservoir) and can include one or more valves, pumps, or the like. The dispenser 622 can output liquid via an array of conduits 625. In some embodiments, including the illustrated embodiment of FIG. 44, the dispenser 622 includes eight conduits 625, but any number of conduits can be used. Additionally, the dispenser assembly 633 can include more than one dispenser depending on the design of the slide holder platen 601. Additionally or alternatively, the dispensers 160, 162 of FIG. 2 can deliver liquid onto the slides and can be fluidly coupled to the fluid source 621 or another fluid source. The opposable 470 can be positioned to allow one or both of the dispensers 160, 162 to deliver a liquid onto the slide. In some embodiments, the dispenser 622 delivers a bulk liquid from the containers at the parking station 142 and the dispensers 160, 162 deliver liquid from containers at the parking station 140.

The controller 144 is capable of controlling an array of specimen processing stations to keep a volume of a processing liquid within an equilibrium volume range. If the volume of the liquid is above the equilibrium volume range, the liquid can evaporate at a relatively high rate and may significantly change the concentration of the liquid. If the volume of the liquid is below the equilibrium volume range, there may be an insufficient volume of liquid to adequately process the specimen. Additionally, an insufficient volume of liquid can result in an undesirably low amount of liquid agitation during processing. The equilibrium volume range can be selected based on the composition of the liquid, desired processing temperature, or desired agitation of the liquid 802. An equilibrium volume of the liquid 802 can correspond to a fluid volume (at a certain temperature or range of temperatures) that provides full coverage of the specimen while keeping evaporative losses below a target level. The dispenser 622 can function as a replenishment device that periodically supplements the liquid at a fixed rate (e.g., a rate based on the evaporation rate) to keep the volume of the liquid within the equilibrium volume range, replenish depleted reagent, or the like.

With the target processing temperature or target processing temperature range and a total evaporation rate, the controller 144 can determine a target range of equilibrium volumes. In some embodiments, the controller 144 can receive the total evaporation rate information from a memory 629 and/or an input device 628. The input device 628 can include a data server or other similar device that can provide information from a database upon request or periodically. The total evaporation rate information can be obtained from an empirical study and stored in the database. In other embodiments, the input device 628 can be a reader that obtains information (e.g., a target processing temperature, a target processing temperature range, replenishing rate, etc.) from a label of a slide.

The controller 144 can receive information (e.g., look-up tables, temperature set points, duty cycles, power settings, environmental information such as ambient temperatures and/or humidity, processing protocols, etc.) from the memory 629. The input device 628 can be a manual input device (e.g., a keyboard, a touch screen, or the like) or an automated input device (e.g., a computer, a data storage device, servers, network, etc.) that can provide information automatically upon request from the controller 144. The memory 629 can store different instructions for different processes. One stored sequence of program instructions can be used to contact the specimen 807 with a wash and another sequence of program instructions can be used to apply a reagent (e.g., a stain) to the specimen. The controller 144 can include a programmable processor 631 that executes the sequence of program instructions in order to sequentially process the specimen with the wash and reagent. The slide holder platen 601 can heat the slide to a first target temperature when executing the first sequence of program instructions and can cool the slide to a second target temperature when executing the second sequence of program instructions. Any number of sequences of program instructions can be executed to perform different stages of a protocol.

The controller 144 can also be programmed to control the wetting module 430 such that the dispenser 622 delivers the supplemental liquid onto the slide. The rate of fluid delivery can be based on, for example, processing information (e.g., protocol, agitation information, processing time(s), etc.), total evaporation rate information (e.g., evaporation rates under certain conditions, the actual evaporation rate for a certain type of liquid, etc.), or the like. The current volume of the liquid can be determined based on an initial volume of liquid on the slide and stored evaporation rate(s). The stored evaporation rates can be input into the system 100 or determined by the system 100. The controller 144 can calculate the equilibrium volume in advance (e.g., a pilot run), and the system 100 can use the determined equilibrium volume as the initial volume for the same kind of liquids. Then the controller 144 can instruct the dispenser 622 to provide the supplemental liquid at a rate (e.g., a rate determined by the pilot run). In some embodiments, the roll speed can be about 100 mm/s to provide a generally uniform temperature profile. For example, a roll speed of 100 millimeters per second can provide a temperature range across the slide of about 4.2° C. whereas a roll speed of 65 millimeters per second provides a temperature range of about 6.2° C. The rolling direction, the rolling speed, and the rolling frequency can be adjusted depending on the type of liquids and the desired temperature profile. The rolling speed can have a direct impact on the total evaporation rate. A faster rolling speed can lead to higher evaporation rates. When collecting empirical total evaporation volume information to generate protocols, this can be a factor that is considered.

A power source 627 of the controller 144 can be electrically coupled to a heating element (e.g., heating element 653 of FIGS. 37A and 37B). The power source 627 can be one or more batteries, fuel cells, or the like. The power source 627 can also deliver electrical energy to other components of the system. In other embodiments, the power source 627 can be an AC power supply.

Figure 45:
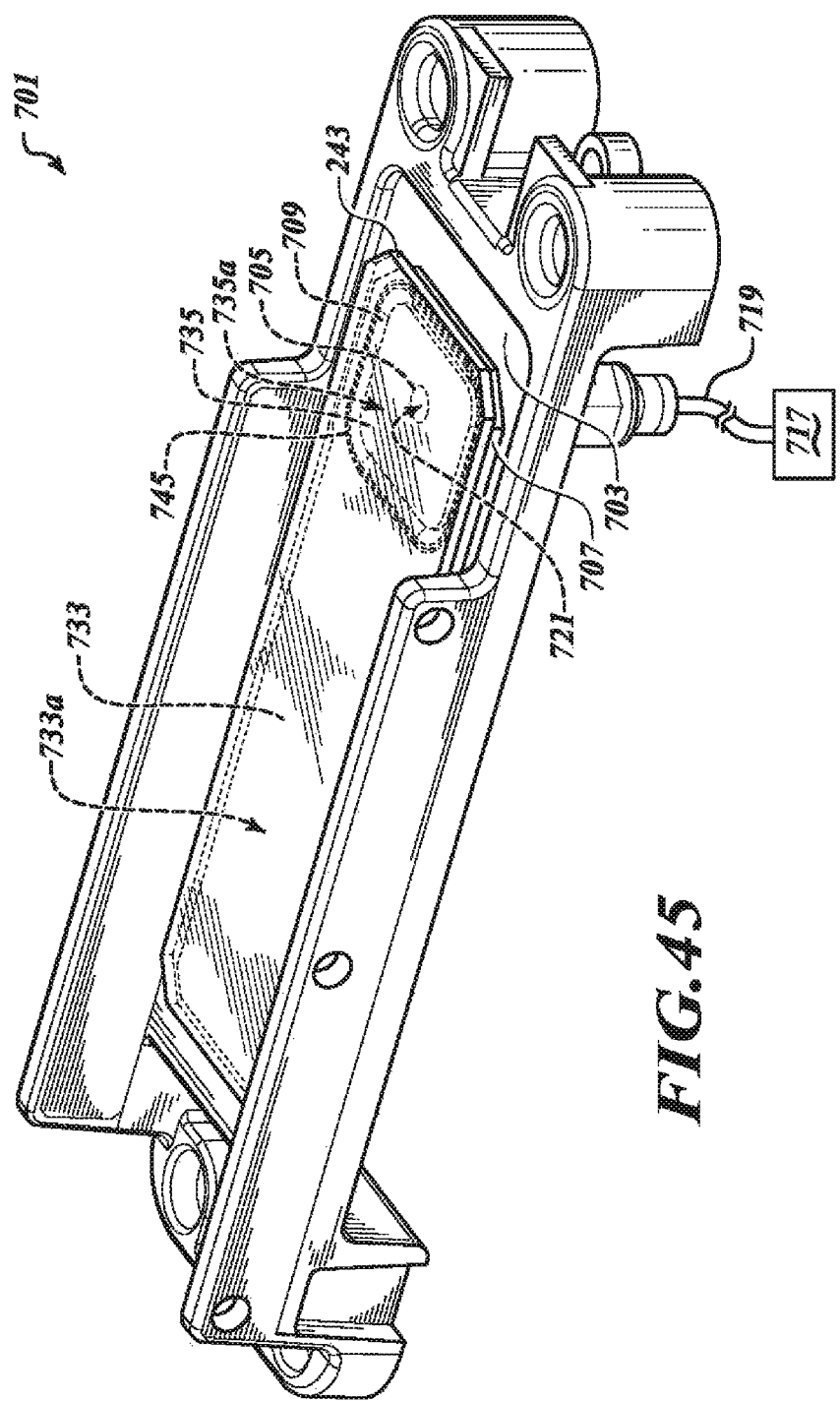
FIG. 45 is a perspective view of a slide holder platen in accordance with an embodiment of the disclosed technology, shown holding a slide.
Figure 46:
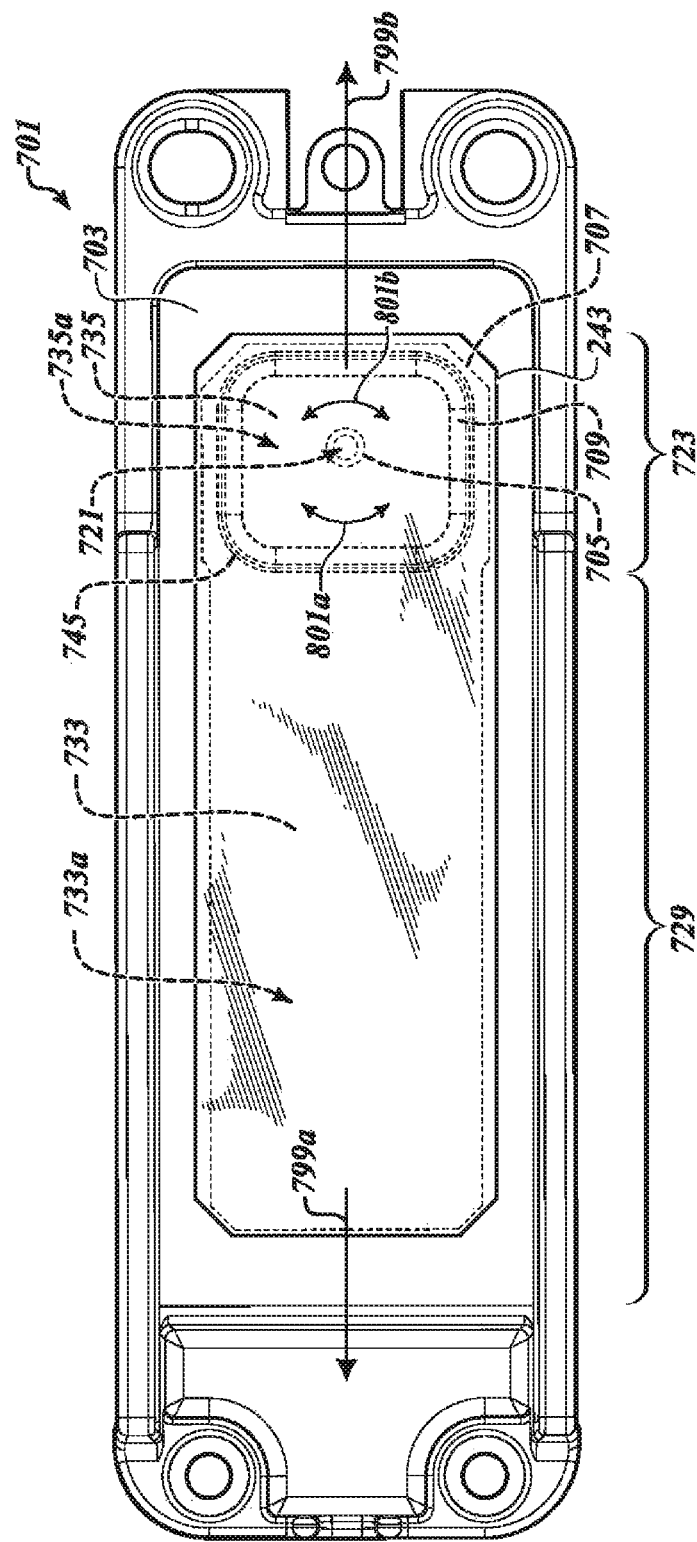
FIG. 46 is a top view of the slide holder platen shown in FIG. 45.
Figure 47:
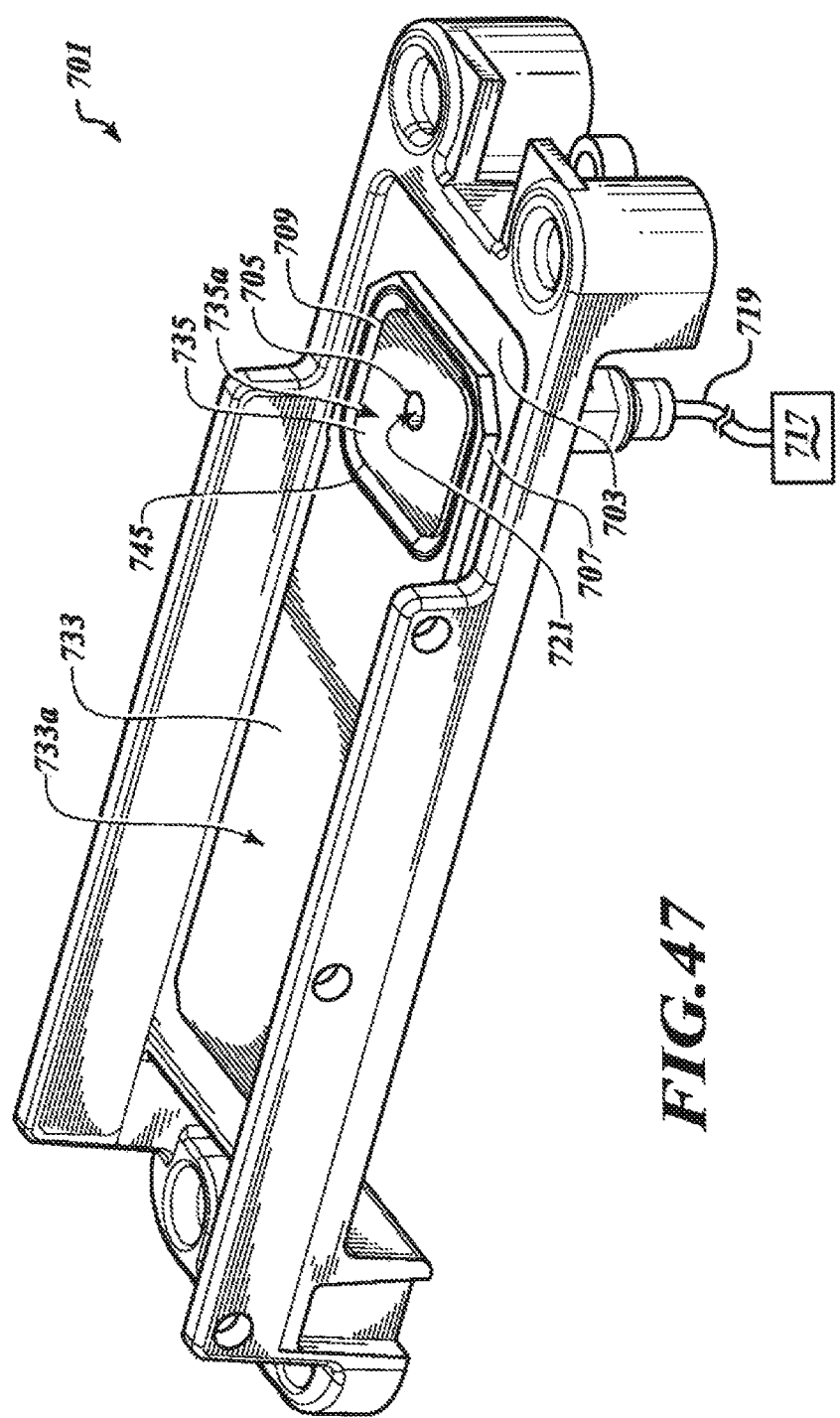
FIG. 47 is a perspective view of the slide holder platen in accordance with the disclosed technology, shown without a slide.

FIGS. 45 and 46 are perspective and top views, respectively, of another embodiment of a slide holder platen 701 shown with a slide 243 and configured in accordance with the present technology. FIG. 47 is a perspective view of the slide holder platen 701 without a slide 243. Referring to FIGS. 45-47, the slide holder platen 701 is generally identical to the slide holder platen 601 discussed above in connection with FIGS. 34A-44, except as detailed below. The slide holder platen 701 can include a support element 703, a sealing member 709, and a vacuum port 721. The support element 703 includes a raised slide-receiving region 707, and the sealing member 709 is configured to engage a bottom surface of the slide 243 as the slide is placed on the slide-receiving region 707. The sealing member 709 can be positioned around the vacuum port 721 such that, when the slide 243 engages the sealing member 709, a vacuum is drawn via the vacuum port 721 to pull the slide 243 against the sealing member 709 to maintain a seal (e.g., an airtight seal) and prevent or limit unwanted movement (e.g., rotational movement and/or translational movement as indicated by arrows 801*a-b* and 799*a-b*, respectively, in FIG. 46) of the slide 243 relative the slide-receiving region 707.

Referring now to FIG. 47, the slide-receiving region 707 can have a first portion 733 and a second portion 735 disposed within an opening 745 of the first portion 733. The vacuum port 721 can be disposed at a top surface 735*a* of the second portion 735 at a generally central location. The vacuum port 721 can be fluidically coupled to a vacuum source 717 via one or more fluid lines 719 (e.g., internal fluid lines, external fluid lines, etc.). For example, the fluid line(s) 719 can extend from an opening 705 at the top surface 735*a* through the second portion 735 to the vacuum source 717. The vacuum source 717 can include, without limitation, one or more pressurization devices, pumps, or other types of devices capable of drawing a vacuum via the opening 705. As shown in FIG. 46, when the slide 243 is positioned on the slide-receiving region 707, the specimen-bearing portion 729 of the slide 243 is generally aligned with the first portion 733, and the label-bearing portion 723 of the slide 243 is generally aligned with the second portion 735. As such, a vacuum generated by the vacuum port 721 can be localized to the label-bearing portion 723 of the slide 243 to avoid disrupting thermal processing of the specimen-bearing portion 729.

The second portion 735 and opening 745 can individually have a non-round shape (as viewed from above). As used herein, "non-round" refers to any shape other than a true circle (i.e., a shape having a substantially constant radius at every point around its perimeter). For example, in some embodiments the second portion 735 and/or opening 745 can have a rectangular shape with rounded corners. In other embodiments, the second portion 735 and/or opening 745 can have any non-round shape, size, and/or configuration, such as a rounded-corner polygonal shape, a polygonal shape, an oval, an ellipse, and the like. In some embodiments (including the illustrated embodiment), the second portion 735 and the opening 745 can have generally the same non-round shape, and in some embodiments the second portion 735 and the opening 745 can have different non-round shapes.

Figure 48:
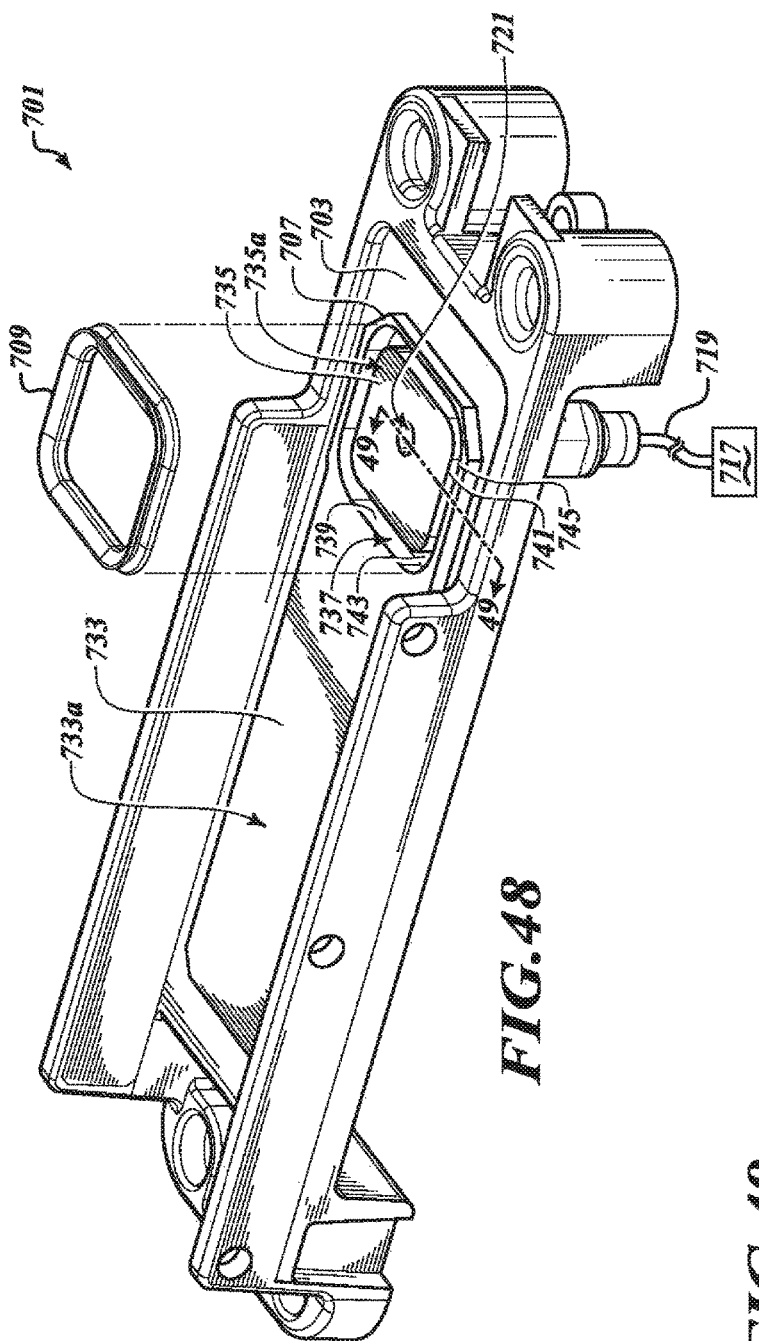
FIG. 48 is a partially exploded view of the slide holder platen.
Figure 49:
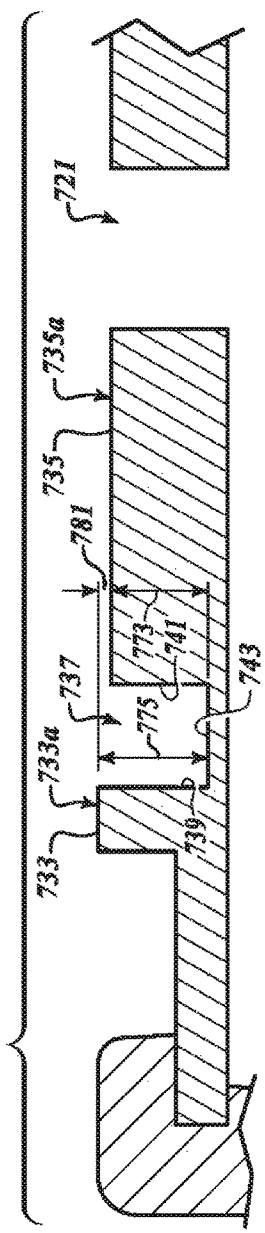
FIG. 49 is an enlarged cross-sectional view of a portion of the slide holder platen shown in FIG. 48.

FIG. 48 is a partially-exploded view of the slide holder platen 701 and FIG. 49 is a cross-sectional side view of a portion of the platen 701 in FIG. 48. Referring to FIGS. 48 and 49 together, the first and second portions 733, 735 of the slide-receiving region 707 are separated by a trench 737 that receives the sealing member 709. The trench 737 defines the opening 745 and can have an outer sidewall 739 defined by the first portion 733, an inner sidewall 741 defined by the second portion 735, and a floor portion 743 between the sidewalls 739, 741. Referring now to FIG. 49, a height 775 of the outer sidewall 739/first portion 733 can be greater than a height 773 of the inner sidewall 741/second portion 735. As described in greater detail below with reference to FIG. 54, when a slide 243 is positioned on the slide-receiving region 707, a backside surface of the slide contacts a top or contact surface 733*a* of the first portion 733 and is separated from a top surface 735*a* of the second portion 735 by a distance 781. As such, the height differential between the first and second portions creates a vacuum chamber 757 (FIG. 54) around the vacuum port 721 that is defined by, at least in part, the top surface 735*a* of the second portion 735.

Figure 50:
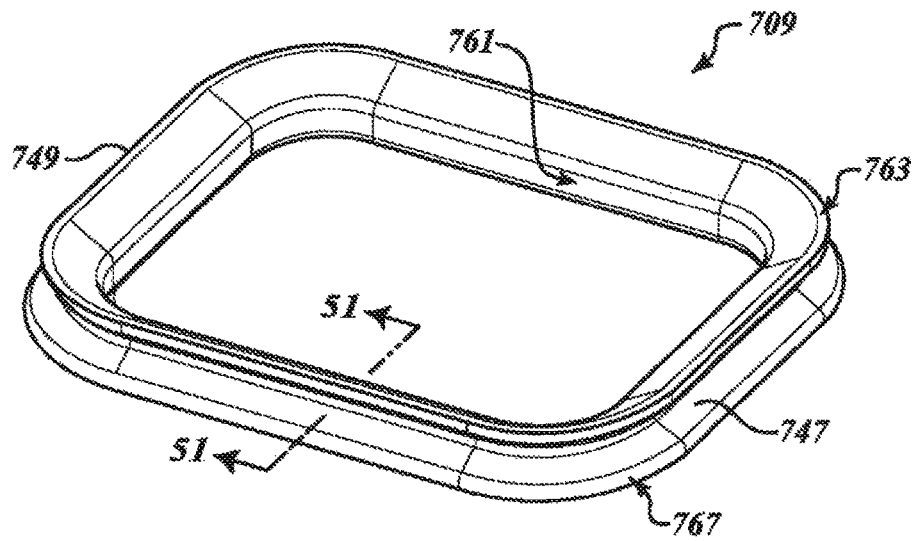
FIG. 50 is a perspective view of a sealing member in accordance with an embodiment of the disclosed technology.
Figure 51:
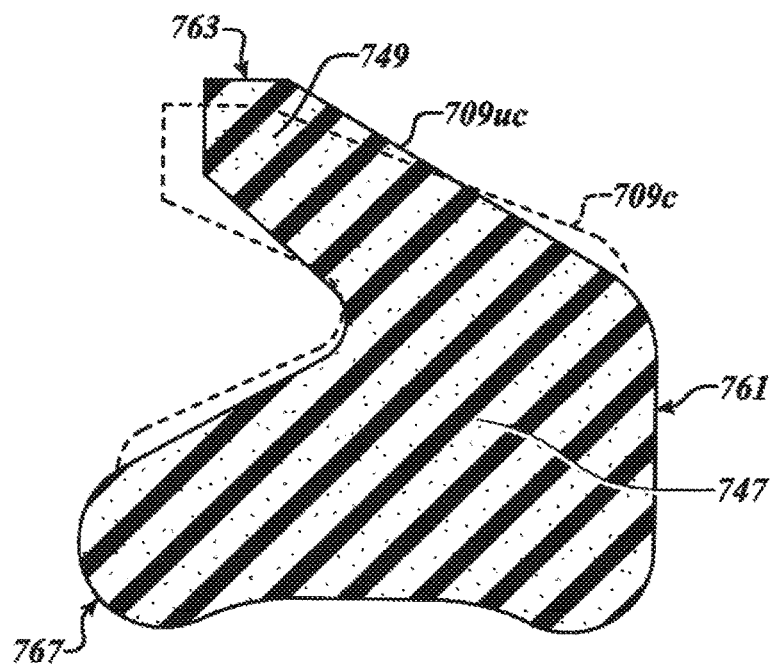
FIG. 51 is a cross-sectional end view of the sealing member of FIG. 50 shown in an uncompressed configuration and a compressed configured (shown in phantom lines).
Figure 52A:
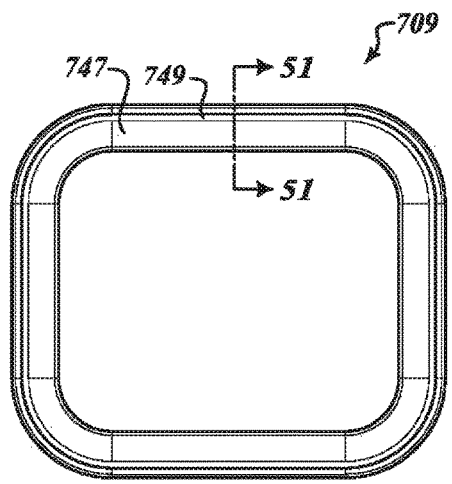
FIG. 52A is a top view of the sealing member of FIG. 50.

FIGS. 50 and 52A are perspective and top views, respectively, of the sealing member 709, and FIG. 51 is a cross-sectional end view of the sealing member 709 taken along line 51-51 of FIG. 50. The sealing member 709 can be in the form of a non-round, compliant gasket having a main body 747 and a lip 749 that extends radially outward from the main body 747. The sealing member 709 is movable between an uncompressed configuration 709$_{UC}$ for contacting the slide that is moving toward the slide-receiving region 707 and a compressed configuration 709$_C$ (shown in phantom lines) for maintaining the airtight seal. The main body 747 can have an interior surface 761 configured to contact the inner sidewall 741 of the trench, and an exterior surface 767 configured to contact the outer sidewall 739 of the trench 737. The lip 749 includes a top surface 763 configured to engage the backside of a microscope slide as the slide is being placed on the slide-receiving region 707. The lip 749 can extend radially outward from the main body 747 a distance less than an exterior surface 767 of the main body 747. As such, the lip 749 does not necessarily make contact the outer sidewall 739 when the sealing member 709 is positioned within the trench 737.

Figure 52B:
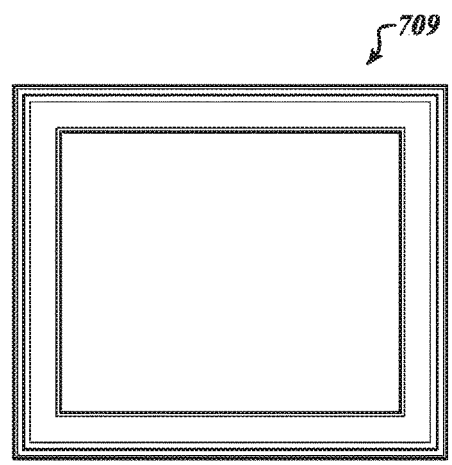
FIGS. 52B-52D are top views of sealing members in accordance with various embodiments of the disclosed technology.
Figure 52C:
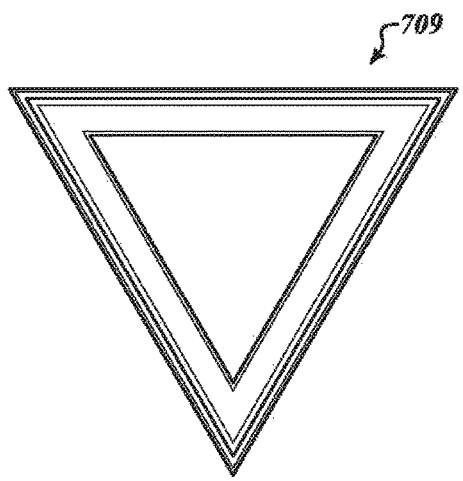
Figure 52D:
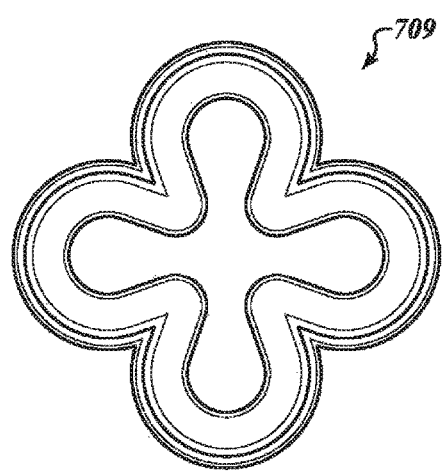

As shown in FIG. 52A, the sealing member 709 (or the main body 747) can have a non-round shape as viewed from above (or along an axis generally perpendicular to a top surface 763 of the sealing member 709). For example, in some embodiments the main body 747 can have a rectangular shape with rounded corners (e.g., FIG. 52A). In other embodiments, the main body 747 can have any non-round shape, size, and/or configuration, such as a rounded-corner polygonal shape, a polygonal shape (e.g., a square (FIG. 52B), a triangle (FIG. 52C), etc.), a "flower-petal" configuration (e.g., FIG. 52D), and/or the like. The sealing member 709 can be made, in whole or in part, of rubber, polytetrafluoroethylene (PTFE), silicone, nitrile, vinyl, neoprene, and/or other compressible or compliant materials capable of maintaining a desired seal.

Figure 53:
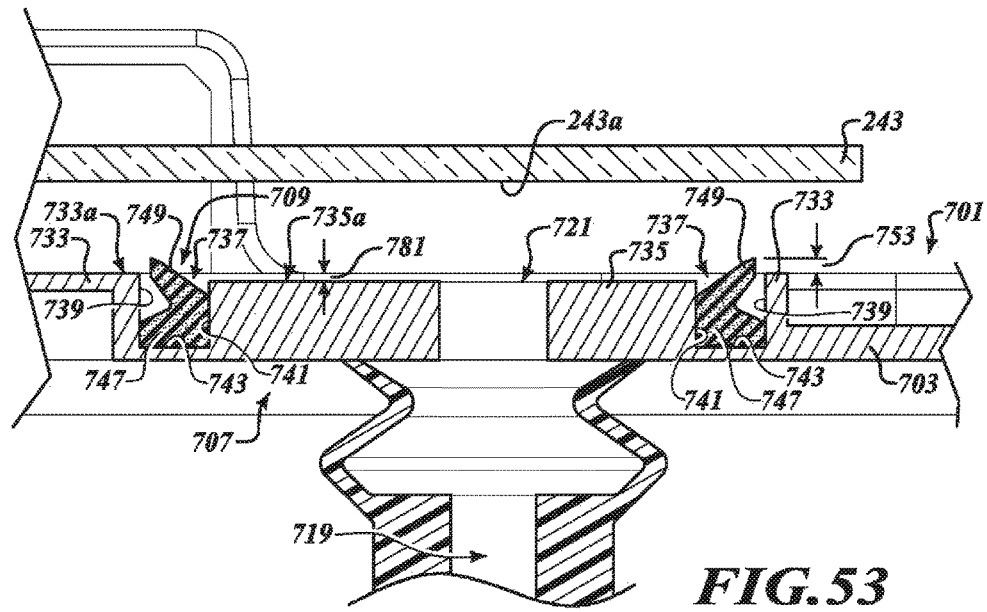
FIG. 53 is a cross-sectional side view of a portion of the slide holder platen before the slide has engaged the sealing member.

FIG. 53 is a cross-sectional side view of the platen 701 as a slide 243 is being positioned on the slide-receiving region 707 but before a backside 243a of the slide 243 has made contact with the sealing member 709 in an uncompressed state. As shown in FIG. 53, at least a portion of the main body 747 is in contact with the inner sidewall 741, outer sidewall 739, and floor portion 743 of the trench 737. The lip 749 is spaced apart from the outer sidewall 739 of the trench 737 and extends upwardly out of the trench 737 beyond the top surface 733a of the first portion 733. The lip 749 can also extends upwardly out of the trench 737 beyond the a horizontal plane (imaginary plane) defined by the top surface 733a. For example, the lip 749 can extend a distance 753 from the top surface 733a. As such, the lip 749 is configured to engage the backside surface 243a of the slide 243 before the backside surface 243a contacts the top surface 733a of the first portion 733. This way, the sealing member 709 absorbs the contact forces associated with the placement of the slide 243 on the slide-receiving region 707, thus easing the transition of the slide 243 onto the slide-receiving region 707.

Figure 54:
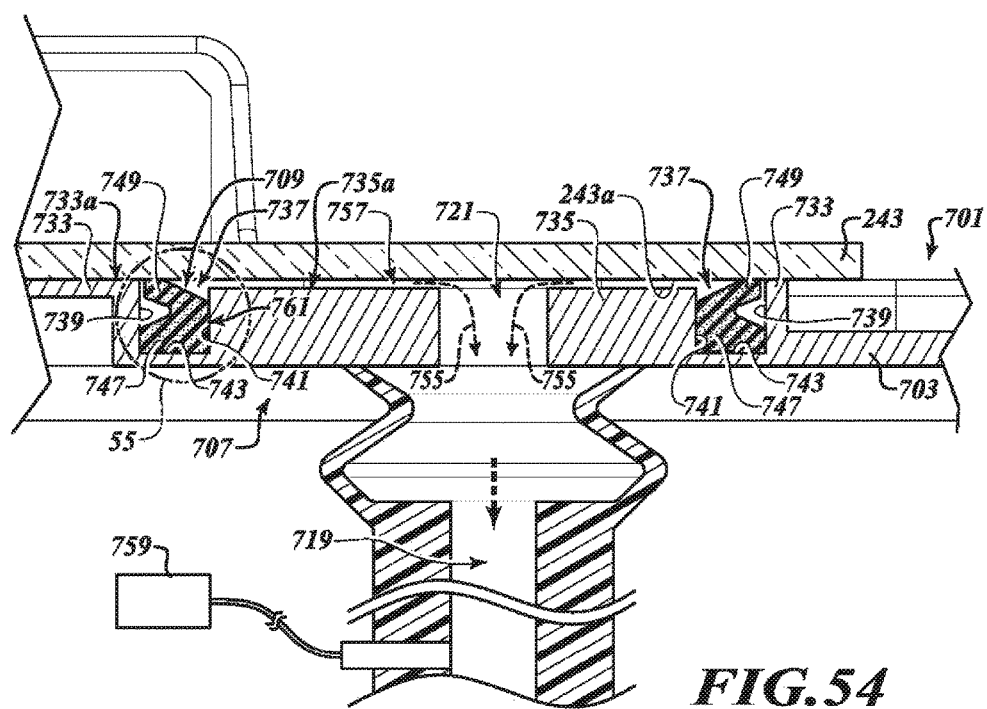
FIG. 54 is a cross-sectional side view of a portion of the slide holder platen after the slide has been positioned on the slide holder platen.
Figure 55:
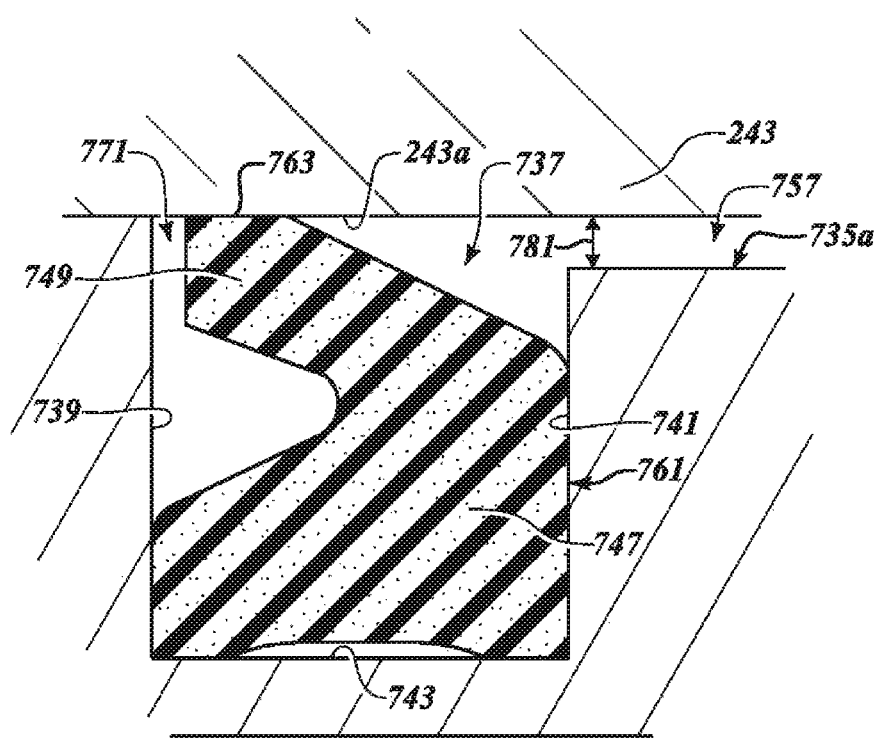
FIG. 55 is an enlarged view of a portion of the slide holder platen shown in FIG. 54.

FIG. 54 is a cross-sectional side view of the platen 701 after the slide 243 has been positioned on the slide-receiving region 707 (e.g., the sealing member 709 is in the compressed state), and FIG. 55 is an enlarged view of a portion of FIG. 54. As shown in FIG. 54, the backside surface 243a of the slide 243 contacts the lip 749 of the sealing member 709 as well as the top surface 733a of the first portion 733. Because of the height differential between the first and second portions 733, 735, the backside surface 243a of the slide 243 is separated from the top surface 735a of the second portion 735 by a distance 781 (see FIG. 55). As such, the pressurized port 721 is positioned below and spaced apart from the backside 243a of the slide 243 such that the top surface 735a of the second portion 735 and the backside surface 243a of the slide 243 at least partially define a vacuum chamber 757. For example, when the vacuum source is activated, fluid and/or air between the backside 243a of the slide 243, a portion of the sealing member 709 (e.g., lip 749 and/or exterior surface 761 of the main body 747), the inner sidewall 741, and/or the top surface 735a of the second portion 735 is drawn through the vacuum port 721 (as indicated by arrows 755). As a result, the slide 243 is pulled against the sealing member 709, thereby forming a seal. The seal secures the positioning of the slide 243 relative to the support element 703 and substantially eliminates unwanted rotation and/or translation of the slide 243.

Figure 56:
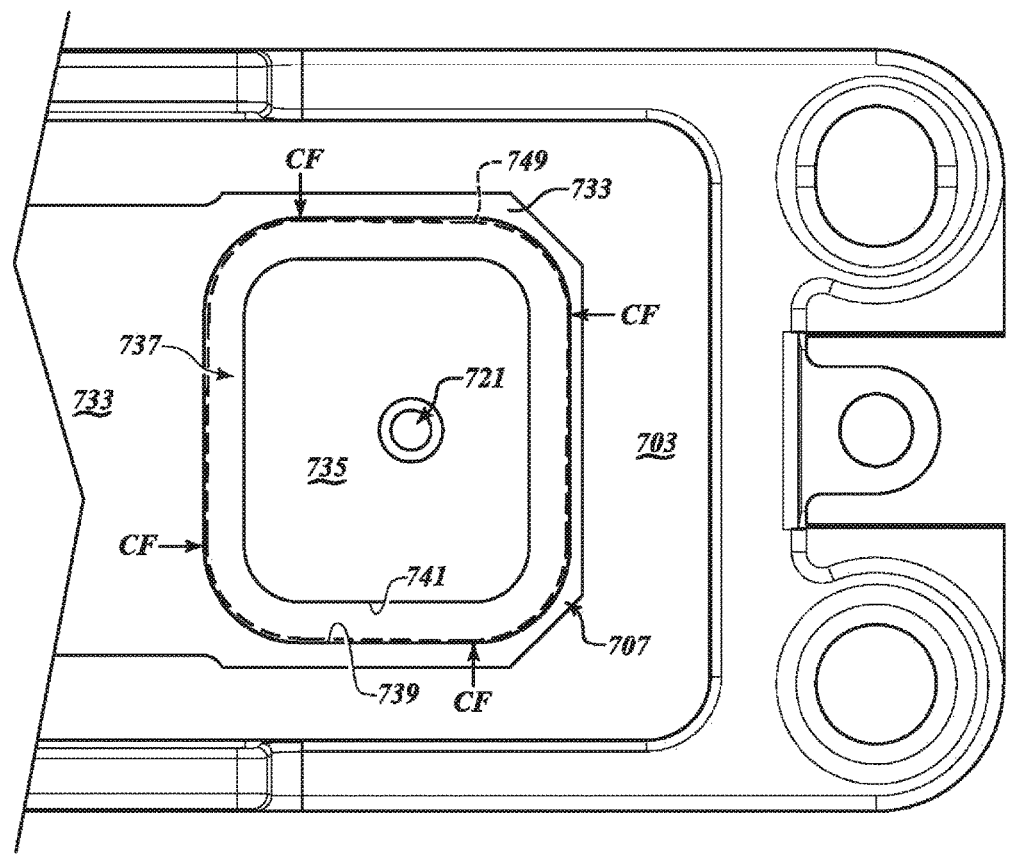
FIG. 56 is an enlarged, top view of a portion of the slide holder platen showing the sealing member in contact with trench walls.

The lip 749 can be movable between the uncompressed configuration and the compressed configuration without contacting the outer sidewall 739 of the trench 737. As best shown in FIG. 55, even in the compressed configuration, a gap 771 can remain between the sealing member lip 749 and the outer sidewall 739 of the trench 737. For example, the lip 749 can be configured to deflect primarily in a direction perpendicular to the backside surface 243a of the slide 243. The lip 749 can be sufficiently stiff to prevent any rotation of the slide 243 about a vertical axis. As such, the slide 243 can rotationally fixed relative to the support surface. Although (in the compressed state) the lip 749 can be separated from the outer sidewall 739, the lip 749 is configured to physically contact the sidewall(s) of the trench 737 to inhibit movement of the slide 243 relative to the support element 703. For example, as shown in FIG. 56, the lip 749 or other portion of the sealing member 709 can be configured to physically contact the outer sidewall 739 of the trench 737 when the slide 243 is rotated about its vertical axis (e.g., at least about 2 degrees). Because of the non-round shape of both the sealing member 709 and the opening 745 in the first portion 733, the outer sidewalls 747 of the trench 737 limit rotation of the sealing member 709 (e.g., by exerting a contact force CF) and thus the slide 743.

The slide holder platen 701 can include additional features. For example, the slide holder platen 701 can include one or more sensors 759 (FIG. 54) to detect the presence of the slide 243 and/or activate the vacuum source 717. In some embodiments, the slide holder platen 701 can include one or more sensors to monitor the pressure generated within the vacuum chamber 757. In particular embodiments, the slide holder platen 701 can be in communication with a controller that can control the timing and/or magnitude of the vacuum source 717.

Figure 57:
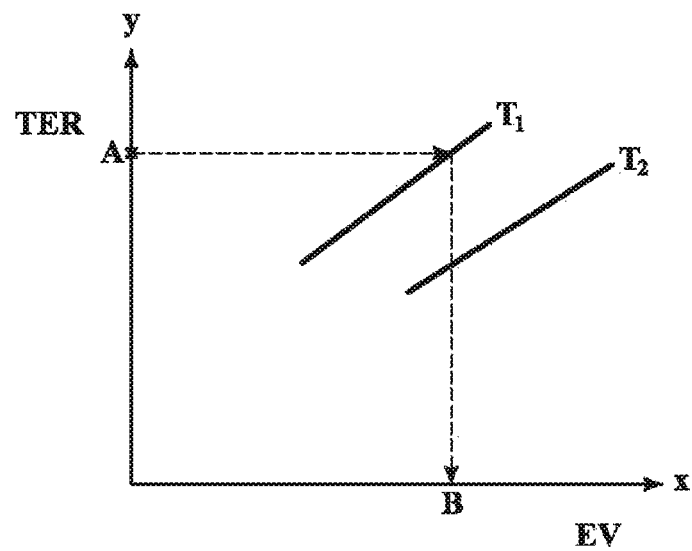
FIG. 57 is a plot of equilibrium volume of a liquid on a slide versus total evaporation rate of the liquid in accordance with an embodiment of the disclosed technology.

FIG. 57 is a plot of equilibrium volume versus total evaporation rate of a processing liquid in accordance with an embodiment of the present technology. The x-axis represents the equilibrium volume (EV, unit: μL), and the y-axis represents the total evaporation rate (TER, unit: μL/s). Lines T1 and T2 represent the relationships between the TER and the EV at temperature T1 and temperature T2, respectively. In the illustrated embodiment, T1 is higher than T2. The controller 144 can receive the total evaporation rate information from the memory 629, the input device 628, or the like. The total evaporation rate information can be measured and stored in the memory 629. The total evaporation rate information can include evaporation rates for liquids at different concentrations. After the controller 144 receives the predetermined temperature (e.g., T1) and the total evaporation rate information (e.g., "A" μL/s), the controller 144 can determine the EV value (e.g., "B" μL) of the liquid based on the graph of FIG. 57. Equation 1 corresponds to the relationships described in FIG. 57. The slope of the lines T1 and T2 represent the temperature-dependent evaporation constant (K) below.

$$TER = K \times EV \qquad \text{Equation 1}$$

Once the equilibrium volume of the liquid is determined, the controller 144 can compare it with an estimated volume of the slide and can instruct the dispenser 622 to supply supplemental fluid if needed. If the current volume of the liquid is lower than the target equilibrium volume, the controller 144 can instruct the dispenser 622 to provide more supplemental liquid.

Figure 58:
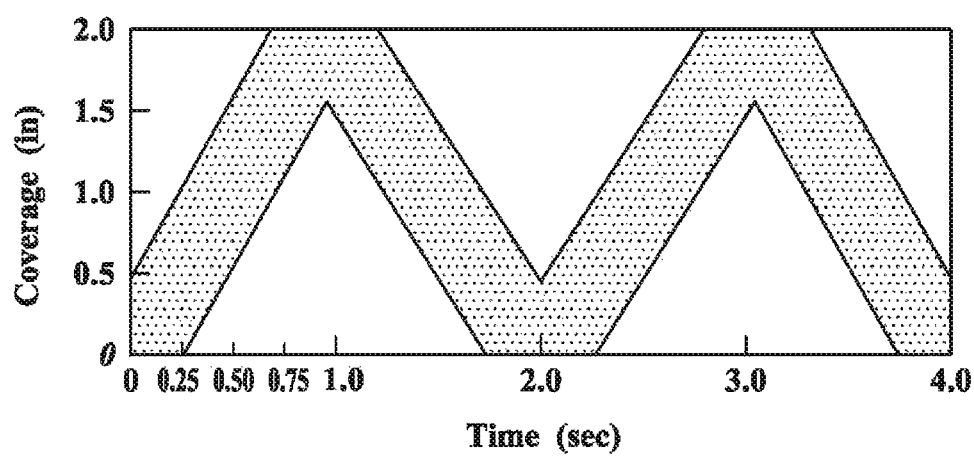
FIG. 58 is a plot of time versus liquid coverage in accordance with an embodiment of the disclosed technology.

FIG. 58 is a plot of time versus coverage of a slide in accordance with an embodiment of the disclosed technology. FIGS. 59A-63B illustrate one method of achieving the coverage depicted in FIG. 58 by moving the liquid 802 along the entire staining area 671 (excluding a label 907 and some margin, if desired) to provide full coverage by being alternatingly moved between opposing ends 732, 735 of the mounting area 671. The full coverage can help minimize, limit, or substantially prevent problems associated with under-wetting and over-wetting. In under-wetting, the liquid 802 contacts less than the entire staining area 671 such that the specimen 807 may be at risk of not being contacted and thus not being treated/stained. In over-wetting, the liquid 802 contacts more than the entire staining area 671 and may tend to drain from the slide 243. The liquid 802 may be at risk of ineffective liquid removal in subsequent processes, resulting in reagent carryover and associated stain quality degradation. If the liquid 802 is a stain, the entire specimen 807 is contacted for consistent (e.g., uniform) staining. If the liquid 802 is a wash, full coverage ensures that the entire specimen 807 is thoroughly washed, especially after a reagent treatment. Different stages of the method are discussed in detail below.

Figure 59A:
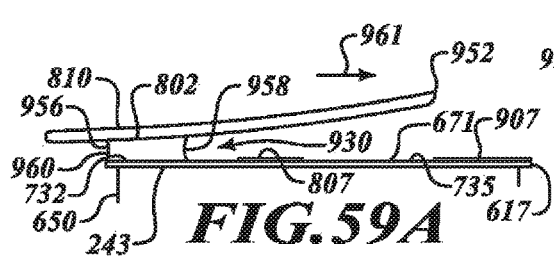
FIGS. 59A and 59B are side and top views of a narrowed band of liquid at an end of a gap between an opposable and a slide.
Figure 59B:
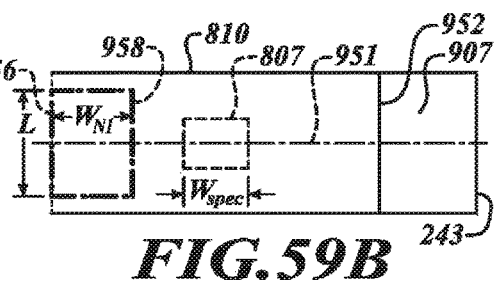

FIGS. 59A and 59B are side and top views of the band of liquid 802 between the opposable 810 held by the opposable actuator (not shown) and the mounting area end 732 at time 0 in FIG. 58. The opposable 810 and slide 243 form a band of liquid 802 (e.g., a meniscus layer, a thin film, or the like). The band of liquid 802 of FIG. 59B is shown in phantom line. A gap 930 (e.g., a capillary gap) can have a minimum holding capacity of about 125 microliters to about 200 microliters. Other minimum and maximum holding capacities are possible, if needed or desired. The minimum holding capacity can be the smallest volume of liquid that can be contained in the gap 930 and effectively applied to the specimen 807, which may be located anywhere on the staining area 671. The maximum holding capacity is the largest volume of liquid that can be contained in the gap 930 without over-filling. The varying height gap 930 can accommodate a wider range of liquid volumes than a uniform height gap because the narrowed region of the gap 930 can accommodate a small liquid volume.

Figure 60A:
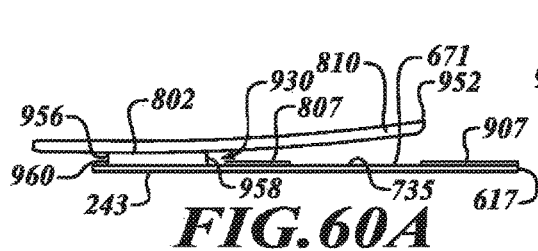
FIGS. 60A and 60B are side and top views of the spread band of liquid.
Figure 60B:
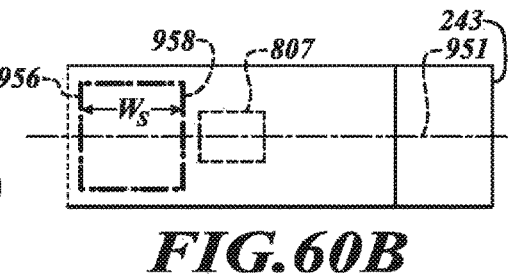

The opposable 810 is rolled along the slide 243 to displace the band of liquid 802 (indicated by an arrow 961) in the direction of a longitudinal axis 951 of the slide 243. In FIGS. 60A and 60B, the band of liquid 802 has been spread by moving a side 958 of the band of liquid 802 in the direction of the longitudinal axis 951 (corresponding to 0.25 seconds in FIG. 58). A side 956 of the band of liquid 802 can remain at an edge 960 of the slide 243. In some embodiments, the band of liquid 802 can be spread from a narrowed width $W_{N1}$ (FIG. 59B) to a spread width $W_S$. The widths $W_{N1}$, $W_S$ can be substantially parallel to the longitudinal axis 951 of the slide 243, and the length L of the band of liquid 802 can be substantially perpendicular to the longitudinal axis 951.

Figure 61A:
FIGS. 61A and 61B are side and top views of the band of liquid contacting a biological specimen.
Figure 61B:
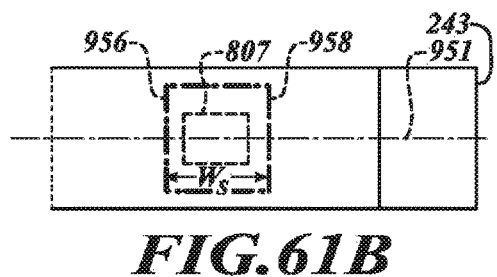

FIGS. 61A and 61B show the band of liquid 802 after it has moved along the slide 243, corresponding to 0.5 second in FIG. 58. The band of liquid 802 is displaced using capillary action. Capillary action can include, without limitation, movement of the band of liquid 802 due to the phenomenon of the liquid spontaneously creeping through the gap 930 due to adhesive forces, cohesive forces, and/or surface tension. In some embodiments, the width $W_S$ can be generally maintained while displacing the band of liquid 802. In other embodiments, the width $W_S$ may be increased or decreased less than 5% while moving the band of liquid 802. In some embodiments, the opposable 810 can have a non-uniform curvature or configuration to have a variable width $W_S$ as the band moves across the slide.

Figure 62A:
FIGS. 62A and 62B are side and top views of the band of liquid between the opposable and a region of the slide adjacent to a label.
Figure 62B:
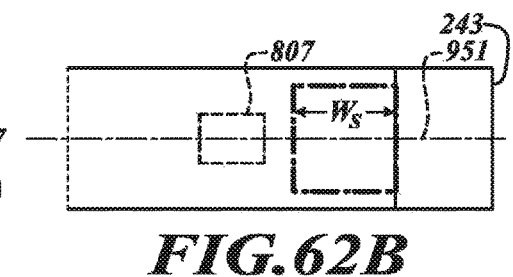

FIGS. 62A and 62B show the band of liquid 802 positioned at the end 735, corresponding to 0.75 second in FIG. 58. The side 958 of the band of liquid 802 can be captivated between an end 952 of the opposable 810 and the end 735 of the mounting area 671. The label 907 can help captivate the liquid 802. For example, the label 907 can be made, in whole or in part, of a hydrophobic material. As the opposable 810 moves to an over-rolled position of FIG. 63A, the width Ws of the band of liquid 802 can be decreased to a narrowed width $W_{N2}$, corresponding to 1 second in FIG. 58. The width of the band of liquid 802 can be reduced while captivating substantially all of the liquid 802 at an end 970 of the gap 930. For example, at least 90% by volume of the liquid 802 can remain captivated. In some embodiments, at least 95% by volume of the liquid 802 can remain captivated. In yet further embodiments, substantially all of the liquid 802 can remain captivated as the width of the band of liquid 802 is decreased.

The compressed width $W_{N2}$ can be substantially less than the width $W_S$ such that the entire narrowed band of liquid 802 is spaced apart from the specimen 807. In some embodiments, the narrowed width $W_{N2}$ can be equal to or less than about 50%, 25%, or 10% of the width $W_S$. Such embodiments may be especially well suited to process slides carrying one or more specimens. A relatively large area of the staining area 671 is uncovered by the narrowed band while preventing wicking or escape of the liquid. In some embodiments, the width $W_{N2}$ can be equal to or less than about 40%, 30%, or 20% of the width $W_S$. The width $W_{N1}$ can be generally equal to the width $W_{N2}$. Advantageously, the opposable actuator 525 can be operated to increase or decrease to provide variable narrowing of the band of liquid 802.

Figure 63A:
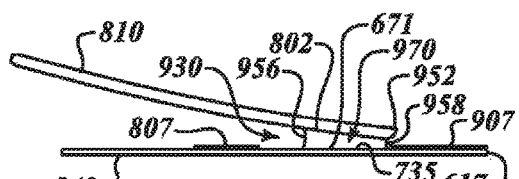
FIGS. 63A and 63B are side and top views of the narrowed band of liquid at an end of a gap adjacent to a label of the slide.
Figure 63B:
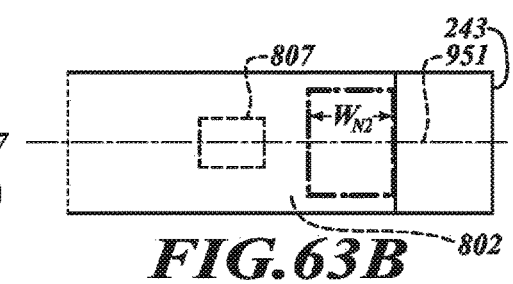

The opposable 810 of FIGS. 63A and 63B can be rolled back across the slide 243 to move the band of liquid 802 to the position shown in FIG. 59A. The opposable 810 can be rolled back and forth any number of times at a variable rate or constant rate to move the liquid 802 back and forth across the slide 243. If the liquid 802 is a washing liquid, the washing liquid can be rapidly passed back and forth across the specimen 807 to provide thorough washing. If the liquid 802 is a stain, the band of liquid 802 can be passed back and forth across the specimen 807 to provide uniform staining across an entire width $W_{spec}$ (measured in a direction parallel to the longitudinal axis 951 of the slide 243) of the specimen 807. One or more wash cycles can be performed between staining cycles. On-slide mixing can also be performed, if needed or desired.

Processing protocols may require different rolling speeds and different liquid volumes in order to meet various processing criteria (e.g., chemical requirements, uptake requirements, solubility limitations, viscosity, or the like). If the specimen 807 is a paraffin embedded specimen, a relatively small volume of de-waxing solution (e.g., 12 microliters of xylene) can be delivered into the gap 930. The opposable 810 can be rolled (e.g., rolled along an imaginary plane spaced apart from the upper surface of the slide 243, rolled along the upper surface, rolled sideways, rolled longitudinally, or the like) or otherwise manipulated (e.g., rotated, translated, or both) to apply the liquid 802. After dewaxing, a relatively large volume of reagent can be delivered into the gap 930. For example, a volume of about 125 microliters to about 180 microliters of stain can be delivered into the gap 930. The stain is delivered to the specimen 807 and then subsequently removed.

The method shown in FIGS. 59A-63B can be used to perform assay steps (e.g., antibody and chromogen assays). The assay steps can be performed at relatively low temperatures. The slide holder platen 601 can keep the specimen and/or processing liquid at a temperature in a range of about 35° C. to about 40° C. In one embodiment, the liquid and/or specimen is kept at a temperature of about 37° C. The dispenser (e.g., dispenser 622 of FIG. 44) can deliver supplemental liquid to maintain a target volume of about 30 microliters to about 350 microliters. In some protocols, the dispenser delivers supplemental liquid at a rate of about 4 to about 5.1 microliters per minute to about 5.6 microliters per minute. In such embodiments, the volume of the liquid (e.g., liquid 802 of FIG. 59A) can be kept in a range of about 90 microliters to about 175 microliters over about a 15 minute period based on a relative humidity of about 10%-90%, an ambient temperature of about 15° C. to about 32° C., with an average slide temperature tolerance of about ±1° C., and an opposable rolling speed of about 25 to 60 millimeters per second. The evaporation rate may be generally proportional to the rolling speed. If the rolling speed is about 20 millimeters per second, a replenish rate of about 3.8 microliters per minute to about 4.2 microliters per minute can maintain a volume of about 115 microliters to about 200 microliters. If the rolling speed is about 40 millimeters per second, a replenish rate of about 5.1 microliters per minute to about 5.6 microliters per minute can maintain a volume of the liquid 802 of about 115 microliters to about 200 microliters. At a high rolling speed of about 90 millimeters per second, the replenish rate can be about 7.6 microliters per minute to about 8.4 microliters per minute to maintain a volume of about 110 microliters to about 200 microliters. Higher speeds may be possible but are dependent upon the gap height, opposable radius, and fluid properties. Humidity and ambient temperatures can impact evaporation rates at low temperatures but may not have a significant impact at elevated temperatures of, for example, temperatures greater than 72° C.

For targeted retrieval, the rolling speed can be about 100 millimeters per second and the replenish rate can be 72 microliters per minute. For antigen retrieval, the rolling speed can be about 180 millimeters per second and the replenish rate can be about 105 microliters per minute. Other replenish rates can be selected based on the processing conditions.

As used herein, the term "opposable element" is a broad term and refers to, without limitation, a surface, a tile, a strip, or another structure capable of manipulating one or more substances to process a specimen on a slide as described herein. The components of the system 100 (FIG. 1) use a wide range of different types of opposable elements. In some embodiments, the opposable element can include one or more spacers, gapping elements or other features for positioning the opposable element relative to a slide. In other embodiments, the opposable element can have a smooth surface (e.g., a non-planer fluid-manipulating surface) that is substantially free of spacers, gapping elements, or the like and can have a monolayer construction or a multi-layer construction. The smooth surface can roll or otherwise travel along a slide. As discussed above, opposable elements can be moved relative to a stationary slide to manipulate a fluid. In other embodiments, a slide is moved relative to a stationary opposable element to manipulate a fluid. In yet other embodiments, both a slide and an opposable element are moved to manipulate a fluid. Additionally, two opposable elements can process specimens. For example, two opposable elements can be used to captivate and manipulate a fluid to process a specimen held between the opposable elements. The specimen can then be transferred to a slide or appropriate specimen carrier. The opposable 810 (FIGS. 59A and 59B) and opposable 2012 are a non-limiting exemplary opposable elements and are discussed in detail in connection with FIGS. 64-67.

FIGS. 64-67 shows one embodiment of the opposable 810. The opposable 810 can include a body 1459, a port 1374, and a slot 1356. The body 1459 includes a first row of gapping elements 1450, a second row of gapping elements 1452, and a specimen processing region 1453. When the specimen processing region 1453 faces a slide and interfaces with a liquid, the liquid can be removed via the port 1374. The slot 1356 can receive a feature of an opposable actuator. The body 1459 can also include keying features 1362, 1364 (e.g., holes, protrusions, etc.) used to align the opposable 810. The illustrated features 1362, 1364 are holes.

Figure 64:
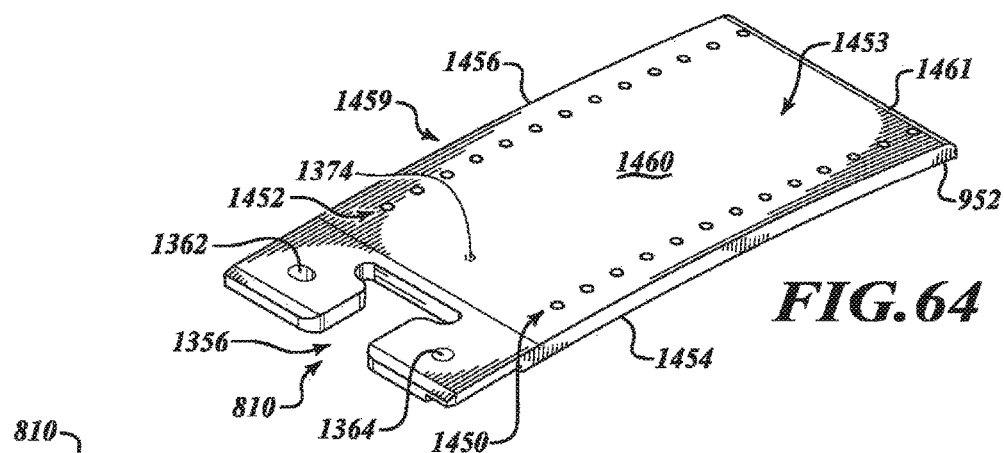
FIG. 64 is an isometric view of an opposable in accordance with one embodiment of the disclosed technology.

FIG. 64 shows the specimen processing region 1453 between the two rows of gapping elements 1450, 1452. The opposable 810 has edges 1454, 1456 that can be dimensioned with respect to the slide to provide the desired processing region 1453 (e.g., the entire surface 1460 of the opposable 810, most of the upper surface 1460 of the opposable 810, the region between the gapping elements 1450, 1452, or the like).

Figure 65:
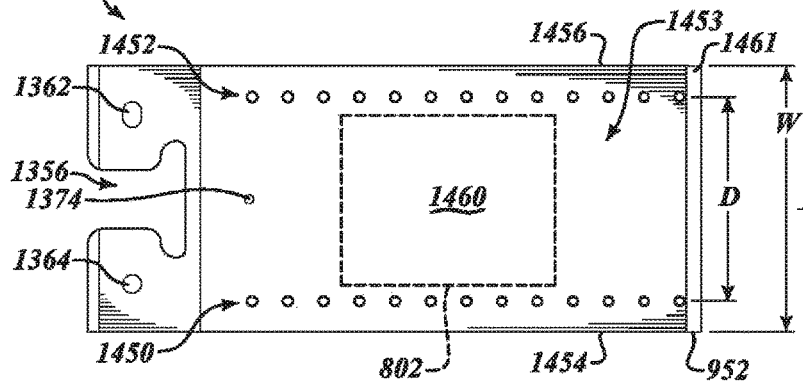
FIG. 65 is a top plan view of the opposable of FIG. 64.

FIG. 65 shows en exemplary band of liquid 802 (illustrated in phantom line) positioned between the gapping elements 1450, 1452. The band of liquid 802 can move along the length of the opposable 810 without contacting the gapping elements 1450, 1452. The band of liquid 802 can be displaced without accumulation of liquid about any of the gapping elements 1450, 1452.

The gapping elements 1450, 1452 can help process a specimen with a desired amount of fluid (e.g., a minimal amount of fluid). The gapping elements 1450, 1452 can also be spaced apart from one another to reduce, limit, or substantially prevent wicking between adjacent elements. If the liquid 802 reaches one of the gapping elements 1450, 1452, the liquid 802 can reside at the contact interface between that gapping element and the slide without flowing to an adjacent gapping element. The gapping elements 1450, 1452 are spaced apart from the edges 1454, 1456 of the opposable 810 to keep the liquid proximate to the processing region 1453. Additionally, the liquid 802 is kept far enough away from the edges 1454, 1456 to prevent wicking out from underneath the opposable 810 even if another object contacts the edges 1454, 1456.

The rows of gapping elements 1450, 1452 extend longitudinally along a length of the opposable 810. Opposing gapping elements of each row of gapping elements 1450, 1452 are generally laterally aligned such that a slide can contact laterally aligned gapping elements 1450, 1452. As the opposable 810 is moved along the slide, the slide is successively brought into contact with laterally aligned gapping elements 1450, 1452.

Each of the rows of gapping elements 1450, 1452 can be generally similar to one another. Accordingly, the description of one of the rows of gapping elements 1450, 1452 applies equally to the other, unless indicated otherwise. The row of gapping elements 1450 can include about 5 gapping elements to about 60 gapping elements with an average distance between adjacent gapping elements in a range of about 0.05 inch (1.27 mm) to about 0.6 inch (15.24 mm). In some embodiments, including the illustrated embodiment of FIGS. 64 and 65, the row of gapping elements 1450 includes 19 gapping elements that protrude outwardly from the entire surface 1460. In other embodiments, the row of gapping elements 1450 includes about 10 gapping elements to about 40 gapping elements. As viewed from above (see FIG. 65), the row of gapping elements 1450 has a generally linear configuration. In other embodiments, the row of gapping elements 1450 has a zigzag configuration, serpentine configuration, or any other configuration or pattern.

The gapping elements 1450 can be evenly or unevenly spaced from one another. The distance between adjacent gapping elements 1450 can be greater than the heights of the gapping elements 1450 and/or less than a thickness T (FIG. 67) of the body 1459 of the opposable 810. Other spacing arrangements are also possible, if needed or desired. In some embodiments, the thickness T is about 0.08 inch (2 mm) A width W between the edges 1454, 1456 can be in a range of about 0.6 inch (15.24 mm) to about 1.5 inch (38 mm). In some embodiments, the width W is about 1.2 inches (30 mm) and the edges 1454, 1456 can be substantially parallel. Other widths are also possible.

Referring to FIG. 65, a distance D between the rows 1450, 1452 can be selected based on the dimensions of the specimen and the dimensions of the slide. In some embodiments, the distance D is in a range of about 0.25 inch (6.35 mm) to about 1 inch (25 mm). If the slide is a standard microscope slide, the distance D can be less than about 0.5 inch (12.7 mm).

Figure 67:
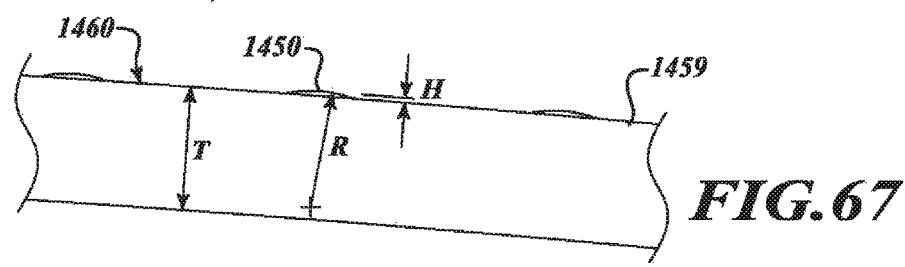
FIG. 67 is a detailed view of a portion of the opposable of FIG. 66.

FIG. 67 shows one of the gapping elements 1450. The height H of the gapping element 1450 can be selected based on the ability to manipulate fluid. The gapping element 1450 can have a height H equal to or less than about 0.0015 inch (0.038 mm) if the specimen is a tissue section with a thickness that is less than about 0.0015 inch (0.038 mm). The minimum height of the capillary gap (e.g., gap 930 of FIGS. 59A-63B) can be equal to 0.0015 inch (0.038 mm) if the gapping elements 1450 contact the slide. In some embodiments, the height H is in a range of about 0.001 inch (0.025 mm) to about 0.005 inch (0.127 mm). In certain embodiments, the height H is about 0.003 inch (0.076 mm) (e.g., 0.003 inch±0.0005 inch) to process thin tissue sections with a thickness less than about 30 microns, 20 microns, or 10 microns.

The pattern, number, dimensions, and configurations of the gapping elements 1450, 1452 can be selected based on the desired interaction between the specimen and the liquid. If the opposable 810 includes a field of gapping elements, the gapping elements can be distributed evenly or unevenly across the opposable 810 to form different patterns that may include, without limitation, one or more rows, arrays, geometric shapes, or the like.

The gapping element 1450 can be a partially spherical dimple, partially elliptical dimple, or the like. The illustrated gapping element 1450 is a substantially partially spherical dimple. If the specimen is sufficiently large or moves toward one side of the slide, the gapping element 1450 in the form of a dimple can slide over the specimen without damaging or dislodging the specimen to the slide. In other embodiments, the gapping element 1450 can be in the form of a polyhedron protrusion, a conical protrusion, a frustoconical protrusion, or another combination of polygonal and arcuate shapes.

Figure 66:
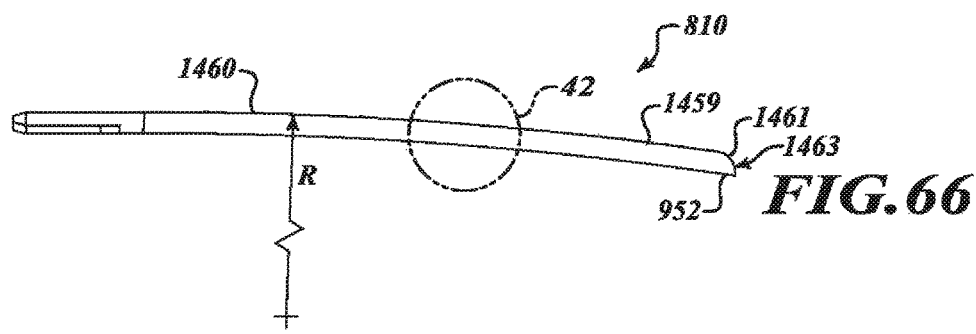
FIG. 66 is a side elevational view of the opposable of FIG. 64.

The body 1459 of FIG. 66 is in the shape of a simple arc with a radius of curvature R in a range of about 2 inches (5 cm) to about 30 inches (76 cm). In some embodiments, the radius of curvature R is about 15 inches (38 cm) or about 20 inches (74 cm). The nominal radius of the profile deviation can be equal to or less than about 0.1 inch. The actual radius of the profile can deviate less than about 0.01 inch. Such embodiments are well suited to produce a liquid band having a generally rectangular shape, as viewed from above, and also spanning the width of the slide and, for a particular volume, having a low variance in length along the slide. The radius of curvature R can be selected based on the number of specimens to be processed, the amount of fluid agitation, the properties of the processing liquids, the height of gapping elements 1450, 1452, and the like. In other embodiments, the opposable 810 is in the shape of a complex arc (e.g., an elliptical arc), a compound arc, or the like. In yet other embodiments, the opposable 810 can be substantially planar. The surface across the width W can be generally straight.

The opposable 810 can be made, in whole or in part, of polymers, plastics, elastomers, composites, ceramics, glass, or metals, as well as any other material that is chemically compatible with the processing fluids and specimen. Exemplary plastics include, without limitation, polyethylene (e.g., high density polyethylene, linear low density polyethylene, blends, or the like), polyvinylidene fluoride (PVDF), polytetrafluoroethylene (PTFE), perfluoroalkoxy (PFA), or combinations thereof. In some embodiments, the opposable 810 can be made of a single material. In other embodiments, different portions of the opposable 810 are made of different materials. If the opposable 810 is disposable, it can be made, in whole or in part, of a relatively inexpensive material. If the opposable 810 is rigid, it can be made, in whole or in part, of polycarbonate, urethane, polyester, a metal coated plate, or the like.

Referring again to FIG. 66, the end 952 includes a captivation feature in the form of a tapered region 1461. The tapered region 1461 is positioned to captivate the band of liquid. As the opposable 810 is over-rolled, the band of liquid can contact and cling to the tapered region 1461. A curved surface 1463 provides a large surface area to which the liquid can cling. The illustrated tapered region 1461 has a radius of curvature equal to or less than about 0.08 inch to cooperate with a standard microscope slide to captivate a band of liquid. Other radii of curvature can also be used, if needed or desired. In some embodiments, the curvature of the rounded edge 1461 is uniform across the width W of the opposable 810. In other embodiments, the curvature of the rounded edge varies across the width W of the opposable 810.

The opposable 810 can be disposable to prevent cross-contamination. As used herein, the term "disposable" when applied to a system or component (or combination of components), such as an opposable element, a processing liquid, or the like, is a broad term and generally means, without limitation, that the system or component in question is used a finite number of times and is then discarded. Some disposable components, such as an opposable element, are used only once and are then discarded. In some embodiments, multiple components of a processing apparatus are disposable to further prevent or limit carryover contamination. In other embodiments, the components are non-disposable and can be used any number of times. For example, opposable elements that are non-disposable may be subjected to different types of cleaning and/or sterilization processes without appreciably altering the characteristics of the opposable element.

The slides disclosed herein can be a 1 inch×3 inch microscope slide, a 25 mm×75 mm microscope slide, or another type of flat or substantially flat substrate. "Substantially flat substrate" refers, without limitation, to any object having at least one substantially flat surface, but more typically to any object having two substantially flat surfaces on opposite sides of the object, and even more typically to any object having opposed substantially flat surfaces, which opposed surfaces are generally equal in size but larger than any other surfaces on the object. In some embodiments, the substantially flat substrate can comprise any suitable material, including plastics, rubber, ceramics, glass, silicon, semiconductor materials, metals, combinations thereof, or the like. Non-limiting examples of substantially flat substrates include flat covers, SELDI and MALDI chips, silicon wafers, or other generally planar objects with at least one substantially flat surface.

From the foregoing, it will be appreciated that specific embodiments of the invention have been described herein for purposes of illustration, but well-known structures and functions have not been shown or described in detail to avoid unnecessarily obscuring the description of at least some embodiments of the invention. The systems described herein can perform a wide range of processes for preparing biological specimens for analyzing. Where the context permits, singular or plural terms may also include the plural or singular term, respectively. Unless the word "or" is associated with an express clause indicating that the word should be limited to mean only a single item exclusive from the other items in reference to a list of two or more items, then the use of "or" in such a list shall be interpreted as including (a) any single item in the list, (b) all of the items in the list, or (c) any combination of the items in the list. The singular forms "a," "an," and "the" include plural referents unless the context clearly indicates otherwise. Thus, for example, reference to "a specimen" refers to one or more specimens, such as two or more specimens, three or more specimens, or four or more specimens.

The various embodiments described above can be combined to provide further embodiments. In addition, the embodiments, features, systems, devices, materials, methods, and techniques described herein may, in certain embodiments, be applied to or used in connection with any one or more of the embodiments, features, systems, devices, materials, methods, and techniques disclosed in the above-mentioned patents and applications. Aspects of the disclosed embodiments can be modified, if necessary, to employ concepts of the various above-mentioned patents, applications, and publications to provide yet further embodiments. All applications listed above are incorporated herein by reference in their entireties.

These and other changes can be made to the embodiments in light of the above-detailed description. For example, a seal element can have a one-piece or multi-piece construction and can include any number of retention features. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An automated slide processing apparatus configured to apply at least one reagent to a specimen carried by a microscope slide, the automated slide processing apparatus comprising:
    a support element having a support surface, wherein the support element includes a trench;
    at least one vacuum port; and
    a sealing member having a non-round shape as viewed from above, wherein the sealing member includes a compliant gasket having a main body and a lip, wherein the main body is positioned in the trench, wherein in an uncompressed state the lip extends radially outward from the main body and beyond the support surface of the support element, wherein in a compressed state when the microscope slide is drawn against the support surface by a vacuum drawn via the at least one vacuum port to establish an airtight seal with the backside of the microscope slide the lip extends toward a sidewall of the trench without contacting the sidewall of the trench, and wherein the lip physically contacts the sidewall of the trench to inhibit movement of the microscope slide relative to the support element when the microscope slide is rotated at least about 2 degrees about a vertical axis perpendicular to the support surface and surrounded by the sealing member.

2. The automated slide processing apparatus of claim 1, wherein the sealing member has a rounded-corner rectangular shape or a rectangular shape as viewed from above.

3. The automated slide processing apparatus of claim 1, wherein the sealing member has a rounded-corner polygonal shape or a polygonal shape as viewed along an axis generally perpendicular to the support surface.

4. The automated slide processing apparatus of claim 1, wherein at least a portion of the support element extends between the sealing member and the at least one vacuum port, wherein the portion has a non-round shape as viewed from above.

5. The automated slide processing apparatus of claim 1, wherein the support element includes a vacuum surface surrounding the at least one vacuum port, wherein the vacuum surface is spaced apart from and positioned below the support surface such that the vacuum surface and the microscope slide in the compressed state at least partially define a vacuum chamber with a height less than a height of the sealing member in the uncompressed state.

6. The automated slide processing apparatus of claim 1, wherein the lip is configured to deflect primarily in a direction perpendicular to the backside surface of the microscope slide during use.

7. The automated slide processing apparatus of claim 1, wherein the lip is configured to be deflected as the microscope slide moves toward the support surface to form the airtight seal.

8. The automated slide processing apparatus of claim 1, wherein the sealing member is positioned to be located under a label of the microscope slide.

9. The automated slide processing apparatus of claim 1, further comprising a vacuum source in fluid communication with the at least one vacuum port and configured to draw a sufficient vacuum to maintain the airtight seal.

10. The automated slide processing apparatus of claim 1, further comprising a heater configured to heat the support element such that the support element conductively heats the microscope slide while the sealing member maintains the airtight seal.

* * * * *